(12) United States Patent
Van Schie et al.

(10) Patent No.: US 12,173,302 B2
(45) Date of Patent: Dec. 24, 2024

(54) DISEASE RESISTANT PETUNIA PLANTS

(71) Applicant: Enza Zaden Beheer B.V., Enkhuizen (NL)

(72) Inventors: Christianus Cornelis Nicolaas Van Schie, Amsterdam (NL); Tieme Zeilmaker, Enkhuizen (NL); Geert Johannes De Boer, Ijmuiden (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 361 days.

(21) Appl. No.: 17/551,119

(22) Filed: Dec. 14, 2021

(65) Prior Publication Data

US 2022/0098611 A1 Mar. 31, 2022

Related U.S. Application Data

(63) Continuation-in-part of application No. 16/361,089, filed on Mar. 21, 2019, now abandoned, which is a continuation of application No. 16/055,697, filed on Aug. 6, 2018, now abandoned, which is a continuation of application No. 15/111,285, filed as application No. PCT/EP2014/050572 on Jan. 14, 2014, now abandoned.

(51) Int. Cl.
C12N 15/82 (2006.01)
C12N 9/02 (2006.01)

(52) U.S. Cl.
CPC ....... C12N 15/8279 (2013.01); C12N 9/0071 (2013.01); C12N 15/8282 (2013.01)

(58) Field of Classification Search
CPC .................................................. C12N 15/8279
USPC ........................................................ 800/279
See application file for complete search history.

(56) References Cited

U.S. PATENT DOCUMENTS

| | | | |
|---|---|---|---|
| 5,866,776 A | 2/1999 | Marie de Wit | |
| 6,100,451 A | 8/2000 | Chappell et al. | |
| 6,271,439 B1 | 8/2001 | Gurmukh et al. | |
| 7,164,058 B2 * | 1/2007 | Hanson | C07K 14/415 |
| | | | 536/23.6 |
| 7,323,338 B2 | 1/2008 | Amir | |
| 7,777,097 B2 | 8/2010 | Glazebrook et al. | |
| 8,237,019 B2 | 8/2012 | Van Den Ackerveken et al. | |
| 8,354,570 B2 | 1/2013 | Van Den Ackerveken et al. | |
| 8,569,064 B2 | 10/2013 | Spangenberg et al. | |
| 8,575,432 B2 | 11/2013 | Van Den Ackerveken et al. | |
| 8,742,207 B2 | 6/2014 | Van Damme et al. | |
| 8,796,511 B2 | 8/2014 | Van Den Ackerveken et al. | |
| 9,121,029 B2 | 9/2015 | Van Damme et al. | |
| 9,546,373 B2 | 1/2017 | Van Damme et al. | |
| 9,932,600 B2 | 4/2018 | Van Damme et al. | |
| 9,994,861 B2 | 6/2018 | Van Damme et al. | |
| 10,501,754 B2 | 12/2019 | Van Damme et al. | |
| 10,597,675 B2 | 3/2020 | Van Schie et al. | |
| 10,787,673 B2 | 9/2020 | Van Damme et al. | |
| 2003/0172396 A1 | 9/2003 | Cohen et al. | |
| 2004/0031072 A1 | 2/2004 | La Rosa et al. | |
| 2006/0041949 A1 | 2/2006 | Xu et al. | |
| 2006/0048240 A1 | 3/2006 | Alexandrov | |
| 2006/0143729 A1 | 6/2006 | Alexandrov | |
| 2009/0210965 A1 | 8/2009 | McCarthy | |
| 2010/0115658 A1 | 5/2010 | Van Damme et al. | |
| 2012/0227134 A1 | 9/2012 | Schon et al. | |
| 2014/0289897 A1 | 9/2014 | Van Damme et al. | |
| 2015/0052634 A1 | 2/2015 | Park et al. | |
| 2015/0059017 A1 | 2/2015 | Van Damme et al. | |
| 2016/0160233 A1 | 6/2016 | Van Schie et al. | |
| 2016/0272987 A1 | 9/2016 | Gil et al. | |
| 2016/0298130 A1 | 10/2016 | Van Damme et al. | |
| 2016/0298131 A1 | 10/2016 | Van Damme et al. | |
| 2016/0312239 A1 | 10/2016 | Gan et al. | |
| 2016/0326543 A1 | 11/2016 | Van Damme et al. | |
| 2016/0326544 A1 | 11/2016 | Van Damme et al. | |
| 2016/0333370 A1 | 11/2016 | Van Schie et al. | |
| 2017/0283826 A1 | 10/2017 | Van Schie et al. | |
| 2017/0314039 A1 | 11/2017 | Van Schie et al. | |
| 2018/0135071 A9 | 5/2018 | Van Damme et al. | |
| 2018/0320191 A1 | 11/2018 | Van Damme et al. | |
| 2018/0334681 A1 | 11/2018 | Van Schie et al. | |
| 2019/0144878 A1 | 5/2019 | Van Damme et al. | |
| 2019/0203223 A1 | 7/2019 | Van Schie et al. | |
| 2019/0309319 A1 | 10/2019 | Van Schie et al. | |
| 2019/0316143 A1 | 10/2019 | Van Damme et al. | |
| 2020/0040354 A1 | 2/2020 | Van Damme et al. | |
| 2020/0157560 A1 | 5/2020 | Van Schie et al. | |
| 2020/0332313 A1 | 10/2020 | Van Schie et al. | |

(Continued)

FOREIGN PATENT DOCUMENTS

| | | | |
|---|---|---|---|
| EP | 0474857 A1 | 3/1992 | |
| EP | 1033405 A2 | 9/2000 | |
| EP | 2455473 A1 | 5/2012 | |

(Continued)

OTHER PUBLICATIONS

"Federal Register", Feb. 9, 2011, 76(27):7162-7175, 14 pages.
Alignment of cucumber DMR6-specific primers with XP_008462902. 2, filed on May 5, 2019 in Opposition proceedings against EP2455475, 1 page.
Alignment of primers with the two copies of the cabbage DMR6 Gene, filed in Opposition against EP2455477, dated Sep. 7, 2016, 4 pages.
Allowed Claims, Chinese Patent Application No. 201480045857.3, dated Jun. 8, 2020, 1 page.
Amended claims filed after receipt of (European) search report, filed Feb. 10, 2017, during prosecution of EP3094722, 1 page.

(Continued)

*Primary Examiner* — Li Zheng
(74) *Attorney, Agent, or Firm* — Foley Hoag LLP; Brendan T. Jones; David E. Shore

(57) ABSTRACT

The present invention relates to mutant *petunia* (*Petunia* spp.) plants including mutant dmr6.1 and dmr6.2 alleles. The mutant *petunia* plants are resistant to oomycete and fungal pathogens.

20 Claims, 8 Drawing Sheets
(8 of 8 Drawing Sheet(s) Filed in Color)
Specification includes a Sequence Listing.

(56) References Cited

U.S. PATENT DOCUMENTS

2021/0071195 A1 3/2021 Zeilmaker
2021/0115457 A1 4/2021 Van Damme et al.

FOREIGN PATENT DOCUMENTS

| WO | WO1991015585 A1 | 10/1991 |
|---|---|---|
| WO | WO1996036697 A1 | 11/1996 |
| WO | WO1998004586 A2 | 2/1998 |
| WO | WO1998032325 A1 | 7/1998 |
| WO | WO1999045125 A2 | 9/1999 |
| WO | WO2000070016 A2 | 11/2000 |
| WO | WO2000078981 A1 | 12/2000 |
| WO | WO2001055347 A1 | 8/2001 |
| WO | WO2001061021 A2 | 8/2001 |
| WO | WO2002061101 A2 | 8/2002 |
| WO | WO2002088301 A2 | 11/2002 |
| WO | WO2003000906 A2 | 1/2003 |
| WO | WO2004024079 A2 | 3/2004 |
| WO | WO2006032707 A2 | 3/2006 |
| WO | WO2006047358 A1 | 5/2006 |
| WO | WO2006047495 A2 | 5/2006 |
| WO | WO2007051483 A1 | 5/2007 |
| WO | WO2007051626 A2 | 5/2007 |
| WO | WO2008092505 A1 | 8/2008 |
| WO | WO2008092659 A1 | 8/2008 |
| WO | WO2008153927 A2 | 12/2008 |
| WO | WO2009009142 A2 | 1/2009 |
| WO | WO2013086499 A2 | 6/2013 |
| WO | WO2015011101 A1 | 1/2015 |
| WO | WO2015029031 A1 | 3/2015 |
| WO | WO2015106796 A1 | 7/2015 |
| WO | WO2015193418 A1 | 12/2015 |
| WO | WO2016164658 A1 | 10/2016 |
| WO | WO2019042935 A1 | 3/2019 |

OTHER PUBLICATIONS

Amended claims filed after receipt of (European) search report, filed Jan. 22, 2013, during prosecution of EP2455482, 2 pages.
Amended claims filed after receipt of (European) search report, filed Jan. 22, 2013, during prosecution of EP2455483, 2 pages.
Amended claims filed after receipt of (European) search report, filed Jul. 30, 2009, during prosecution of EP2115147, 5 pages.
Amended claims filed after receipt of (European) search report, filed Nov. 19, 2012, during prosecution of EP2455479, 2 pages.
Amended claims filed after receipt of (European) search report, filed Sep. 5, 2016, during prosecution of EP3024929, 2 pages.
Amended claims submitted by applicant on Sep. 25, 2017 for EP2681234 examination proceedings, filed Dec. 7, 2017 in Opposition against EP2455477, 1 page.
Amended claims with annotations, filed Apr. 26, 2018, during appeal of EP2455473, 2 pages.
Amended claims with annotations, filed Sep. 10, 2018, during appeal of EP2455473, 14 pages.
Amended claims, filed Apr. 17, 2018, during prosecution of EP3167051, 1 page.
Amended claims, filed Aug. 17, 2017, during prosecution of EP3167051, 2 pages.
Amended claims, filed Aug. 20, 2010, during prosecution of EP2115147, 4 pages.
Amended claims, filed Dec. 21, 2017, during prosecution of EP3024929, 2 pages.
Amended claims, filed Feb. 2, 2012, during prosecution of EP2115147, 2 pages.
Amended claims, filed Jan. 17, 2018, during prosecution of EP3094722, 1 page.
Amended claims, filed Mar. 17, 2017, during prosecution of EP2455474, 1 page.
Amended claims, filed May 26, 2011, during prosecution of EP2115147, 3 pages.
Amended claims, filed May 28, 2018, during prosecution of EP3094722, 1 page.
Amended claims, filed May 28, 2018, during prosecution of EP3167051, 1 page.
Amended claims, filed Oct. 15, 2018, during prosecution of EP3024929, 1 page.
Amended Claims, Japanese Patent Application No. 2008-538304, dated Oct. 23, 2009, 6 pages.
Amended description with annotations, filed Apr. 17, 2018, during prosecution of EP3167051, 17 pages.
Amended description with annotations, filed Aug. 30, 2016, during prosecution of EP2455475, 30 pages.
Amended description with annotations, filed Aug. 30, 2016, during prosecution of EP2455481, 29 pages.
Amended description with annotations, filed Jan. 17, 2018, during prosecution of EP3094722, 19 pages.
Amended description with annotations, filed Jul. 21, 2016, during prosecution of EP2455476, 29 pages.
Amended description with annotations, filed Jul. 21, 2016, during prosecution of EP2455480, 29 pages.
Amended description with annotations, filed Jun. 5, 2012, during prosecution of EP2115147, 7 pages.
Amended description with annotations, filed Mar. 17, 2017, during prosecution of EP2455474, 29 pages.
Amended description with annotations, filed May 28, 2018, during prosecution of EP3094722, 19 pages.
Amended description with annotations, filed May 28, 2018, during prosecution of EP3167051, 34 pages.
Amended description with annotations, filed Oct. 10, 2016, during prosecution of EP2455474, 29 pages.
Amended description with annotations, filed Oct. 10, 2016, during prosecution of EP2455478, 29 pages.
Amended description with annotations, filed Oct. 21, 2013, during prosecution of EP2455473, 11 pages.
Amended description with annotations, filed Oct. 21, 2013, during prosecution of EP2455477, 11 pages.
Amended description with annotations, filed Oct. 5, 2016, during prosecution of EP2455479, 30 pages.
Amendments received before examination, filed Aug. 17, 2017, during prosecution of EP3167051, 3 pages.
Amendments received before examination, filed Feb. 10, 2017, during prosecution of EP3094722, 2 pages.
Amendments received before examination, filed Jan. 22, 2013, during prosecution of EP2455482, 3 pages.
Amendments received before examination, filed Jan. 22, 2013, during prosecution of EP2455483, 3 pages.
Amendments received before examination, filed Nov. 19, 2012, during prosecution of EP2455479, 3 pages.
Amendments received before examination, filed Sep. 5, 2016, during prosecution of EP3024929, 2 pages.
Analysis performed by Dr. T. Zeilmaker using the protein analysis program PROVEAN, filed Sep. 15, 2017, in Opposition against EP2455473, 3 pages.
Annex B, filed by the Applicant on Aug. 30, 2016, in case EP2455475 during examination, 6 pages.
Annexes (other than cited documents) regarding appeal procedure, Sep. 10, 2018, filed during appeal of EP2455473, 6 pages.
Applicant request for correction/amendment of the text proposed for grant and amended claims, filed Jan. 15, 2019 in case EP3167051, 3 pages.
Applicant request for correction/amendment of the text proposed for grant with amended claims and description, filed Feb. 5, 2019 in case EP3094722, 22 pages.
Applicant request for correction/amendment of the text proposed for grant, filed Aug. 17, 2017 in case EP2455475, 1 page.
Ardi et al., (1998). "Involvement of Epicatechin Biosynthesis in the Activation of the Mechanism of Resistance of Avocado Fruits to Colletotrichum Gloeosporioides", Physiological and Molecular Plant Pathology, 53:269-285.
Aubert et al., (1998). "Transport, Compartmentation, and Metabolism of Homoserine in Higher Plant Cells", Plant Physiol., 116:547-557.

(56) References Cited

OTHER PUBLICATIONS

Auxiliary request containing amended claims, filed Dec. 19, 2017, in Opposition against EP2455473, 1 page.
Auxiliary request containing amended claims, filed Sep. 15, 2017, in Opposition against EP2455473, 1 page.
Auxiliary Request I, filed Apr. 26, 2018, during appeal of EP2455473, 1 page.
Badouin et al. (2017). "The sunflower genome provides insights into oil metabolism, flowering and Asterid evolution," Nature, 546(7656):148-153, 14 pages.
Balass et al., (1992). "Identification of a constitutive 45 kDa soluble protein associated with resistance to downy mildew in muskmelon (Cucumis melo L.), line PI 124111 F", Physiological and Molecular Plant Pathology, 41:387-396.
Belhaj et al., (2013). "Plant genome editing made easy: targeted mutagenesis in model and crop plants using the CRISPR/Cas system," Plant Methods, 9(39):1-10.
Bhattacharyya et al., (2005). "Identification of a Large Cluster of Coiled Coil-Nucleotide Binding Site—Leucine Rich Repeat-Type Genes from the Rps1 Region Containing Phytophthora Resistance Genes in Soybean", Theor. Appl. Genet., 111:75-86.
BLAST comparison between the amino acid sequences of Arabidopsis DMR6 (query ID Query_190785) and XP 013593012.1, dated Sep. 21, 2017, 2 pages.
BLAST comparison between the amino acid sequences of Arabidopsis DMR6 (query ID Query_236939) and XP 013620820.1, dated Sep. 21, 2017, 2 pages.
BLAST comparison results of query ID 258413, filed during prosecution of EP2455475, dated Aug. 30, 2016, 6 pages.
BLAST comparison results of query ID 3871 and subject ID 3873, filed during prosecution of EP2455474, dated Jul. 3, 2013, 2 pages.
BLAST comparison results of query ID XP_003526765.1 and subject ID OAO94377.1, filed during prosecution of EP2455481, dated Aug. 30, 2016, 2 pages.
Blast query of the sequence of Fig. 4 against Spinacia oleracea, filed in Opposition against EP2455473, dated Sep. 4, 2018, 6 pages.
BLAST strategy and results on Solanum lycopersicum nucleotide sequence, filed Jul. 18, 2018, in Opposition against EP2455479, 2 pages.
BLAST strategy and results on Solanum lycopersicum protein sequence, filed Jul. 18, 2018, in Opposition against EP2455479, 5 pages.
BLAST-P query of AtF3H against *A. thaliana* genome, filed in Opposition against EP2455477, dated Dec. 7, 2017, 3 pages.
Bouchez et al., (1998). "Functional Genomics in Plants", Plant Physiology, 118:725-732.
Brandenberger et al., (1992). "Evaluation of Spinach Germplasm for Resistance to a New Race (Race 4) of Peronospora farinosa f. sp. spinaciae," HortScience, 27(20):1118-1119.
Brandenberger et al., (1994). "Characterization of resistance of spinach to white rust (Albugo occidentalis) and downy mildew (Peronospora farinosa f. sp. spinaciae)," Phytopathology, 84(4):431-437.
Brouwer et al., (2004). "Fine mapping of three quantitative trait loci for late blight resistance in tomato using near isogenic lines (NILs) and sub-NILs", Theoretical and Applied Genetics, 108:628-638.
Brouwer et al., (2004). "QTL analysis of quantitative resistance to Phytophthora infestans (late blight) in tomato and comparisons with potato", Genome, 27(3):475-492.
Budiman et al., (2000). "A Deep-Coverage Tomato BAC Library and Prospects toward Development of an STC Framework for Genome Sequencing", Genome Research, 10:129-136.
Burnham et al., (2003). "Quantitative Trait Loci for Partial Resistance to Phytophthora sojae in Soybean", Crop Science, 43(5):1610-1617.
Chen et al., (2008). "Host specificity and tomato-related race composition of Phytophthora infestans isolates in Taiwan during 2004 and 2005," Plant Disease, 92(5):751-755.
Cho et al., (2005). "Constitutive expression of the Flavanone 3-hydroxylase gene related to pathotype-specific Ascochyta blight resistance in Cicer arietinum L.", vol. 67, Physiological and Molecular Plant Pathology, pp. 100-107.
Choi et al., (2012). "Predicting the Functional Effect of Amino Acid Substitutions and Indels", PLoS ONE, 7(10):1-13.
Clough et al., (1998). "Floral Dip: a Simplified Method for Agrobacterium-Mediated Transformation of *Arabidopsis Thaliana*", Plant Journal, 16(6):735-743.
Coelho et al., (2003). "Expression of resistance to downy mildew at cotyledon and adult plant stages in *Brassica oleracea* L.," Euphytica, 133:279-284.
Communication from the Examining Division dated Mar. 20, 2014, filed in Opposition against EP2455474, 1 page.
Communication from the Examining Division dated Mar. 20, 2014, filed in Opposition against EP2455479, 1 page.
Communication from the Examining Division for EP2455473 dated Mar. 20, 2014, filed in Appeal proceedings for EP2455473, 1 page.
Communication from the Examining Division for EP2455477 dated Nov. 14, 2013, filed in Opposition against EP2455477, 2 pages.
Communication from the Examining Division for EP2681234 dated Nov. 20, 2017, filed in Opposition against EP245577, 4 pages.
Communication from the Examining Division in case EP2455475 dated Mar. 20, 2014, concerning the staying of examination proceedings, 1 page.
Communication from the Examining Division in case EP3024929 dated Jul. 9, 2019, concerning the staying of examination proceedings, 3 pages.
Communication from the Examining Division in case EP3094722 dated Jun. 27, 2019, concerning the staying of examination proceedings, 3 pages.
Communication from the Examining Division in case EP3167051 dated Jun. 27, 2019, concerning the staying of examination proceedings, 3 pages.
Communication from the Opposition Division in case EP2455474 dated Jan. 3, 2020, concerning the staying of opposition proceedings, 5 pages.
Communication from the Opposition Division in case EP2455474 dated Jun. 27, 2019, concerning the staying of opposition proceedings, 2 pages.
Communication from the Opposition Division in case EP2455475 dated Jan. 10, 2020, concerning the staying of opposition proceedings, 5 pages.
Communication from the Opposition Division in case EP2455475 dated Jun. 27, 2019, concerning the staying of opposition proceedings, 2 pages.
Communication from the Opposition Division in case EP2455479 dated Jan. 13, 2020, concerning the staying of opposition proceedings, 5 pages.
Communication from the Opposition Division in case EP2455479 dated Jun. 28, 2019, concerning the staying of opposition proceedings, 4 pages.
Communication from the Proprietor in case EP2455474 dated Nov. 11, 2019, concerning the staying of opposition proceedings, 4 pages.
Communication from the Proprietor in case EP2455475 dated Nov. 11, 2019, concerning the staying of opposition proceedings, 4 pages.
Communication from the Proprietor in case EP2455479 dated Nov. 8, 2019, concerning the staying of opposition proceedings, 3 pages.
Communication pursuant to Art. 94(3) EPC dated Mar. 8, 2017, filed Dec. 14, 2018 in Opposition against EP2455474, 3 pages.
Conrath et al., (2003). "Enhanced Resistance to Phytophthora Infestans and Alternaria Solani in Leaves and Tubers, Respectively, of Potato Plants with Decreased Activity of the Plastidic ATP/ADP Transporter", Planta, 19:75-83.
Constantinescu et al., (2002). "Peronospora-like Fungi (Chromista, Peronosporales) Parasitic on Brassicaceae and Related Hosts", Nova-Hedwigia, 74:291-338.
Cooke et al., (2000). "A molecular phylogeny of Phytophthora and related Oomycetes," Fungal Genetics and Biology, 30:17-32.
Crowe et al., (2003). "CATMA: a complete Arabidopsis GST database", Nucleic Acids Res., 31(1):156-158.
CV of Dr. A. Verhage, dated Oct. 20, 2017, submitted in opposition proceedings for EP2455473, 3 pages.
CV of Dr. T. Zeilmaker, filed Sep. 15, 2017, in Opposition against EP2455473, 2 pages.

(56) References Cited

OTHER PUBLICATIONS

Data on sequence and resistance of spinach variants, filed Feb. 14, 2017, in Opposition against EP2455473, 3 pages.
Database EMBL, (Apr. 15, 2002). "*Arabidopsis Thaliana* Flavanone 3-Hydroxylase-like Protein (At5g24530) mRNA, complete Cds", Retrieved from EBI Accession No. EMBL: AY081455. 2 pages.
Database EMBL, (Dec. 18, 2014). "Glycine soja Flavanone 3-dioxygenase", XP002785532, Retrieved from EBI Accession No. EMBL: KHN19568, Database accession No. KHN19568, 2 pages.
Database EMBL, (Jun. 16, 2001). "*Arabidopsis Thaliana* Flavanone 3-Hydroxylase-like Protein {K 18P6.6) mRNA, Complete Cds", Retrieved from EBI Accession No. EMBL: AF386975. 2 pages.
Database EMBL, retrieved from EBI Accession No. EMBL: DQ208192, Database Accession No. DQ208192, 2 pages.
Database EMBL, XP002386701, retrieved from EBI accession no. EM_PRO:AF082525, Database Accession No. AF082525, 2 pages.
Database UniProt, (Jun. 13, 2012). "Glycine max (Soybean); belongs to the iron/ascorbate-dependent oxidoreductase family", XP002785533, Retrieved from EBI Accession No. Uniprot: 11KB21, Database accession No. 11KB21, 2 pages.
Database UniProt, (Nov. 22, 2017). "Putative Homoserine Kinase," XP002780503, Retrieved from Database Accession No. A0A251RZI8, 1 page.
De Jong et al., (2006). "Membrane-associated transcripts in Arabidopsis; their isolation and characterization by DNA microarray analysis and bioinformatics", Plant J., 46(4):708-721.
De las Mercedes Dana et al., (2006). "Transgenic Tobacco Plants Overexpressing Chitinases of Fungal Origin Show Enhanced Resistance to Biotic and Abiotic Stress Agents", Plant Physiol., vol. 142, No. 2, American Society of Plant Biologists, pp. 722-730.
De Wit, P.J.G.M. (1992). "Molecular characterization of gene-for-gene systems in plant-fungus interactions and the application of avirulence genes in control of plant pathogens", Annu. Rev. Phytopathol., 30:391-418.
Decision T 1063/18, filed on Apr. 29, 2019 in Opposition proceedings against EP2455475, 29 pages.
Declaration and CV of Dr. A. Rijpkema, dated Jul. 27, 2018, submitted in opposition proceedings for EP2455474, 4 pages.
Declaration and CV of Dr. B. D'hoop, dated Jul. 27, 2018, submitted in opposition proceedings for EP2455474, 3 pages.
Declaration and CV of Dr. P.M. Eggink, dated Jul. 14, 2018, submitted in opposition proceedings for EP2455479, 3 pages.
Declaration by Dr. A. Verhage, dated Jun. 26, 2017, submitted in opposition proceedings for EP2455474 and EP2455479, 1 page.
Declaration of Dr. A. Verhage, dated Oct. 17, 2017, submitted in opposition proceedings for EP2455473, 2 pages.
Develey-Riviere et al., (2007). "Resistance to pathogens and host developmental stage: a multifaceted relationship within the plant kingdom," New Phytologist, 175:405-416.
Disease test results DMR6 Spinach mutants, filed Jul. 17, 2017, in Opposition against EP2455473, 1 page.
Elliott, Charlotte (1992). "Relative Susceptibility to Pythium Root Rot of Twelve Dent Corn Inbreds", Journal of Agricultural Research, 64(12):711-723.
Enza lettuce catalogue, dated Jan. 17, 2014, filed in Opposition to EP2115147, p. 102-115.
Experimental data "Annex A—Overview supporting data DMR6 down regulation and disease resistance," filed Oct. 10, 2016 by the Applicant during the examination of EP2455474 (six page excerpt filed Jul. 18, 2018 in Opposition against EP2455479), 28 pages.
Experimental data on mutation in dmr6 conferring resistance to cabbage, filed during Opposition against EP2455477, dated Jan. 18, 2018, 3 pages.
Experimental data showing no Phytophthora resistance, filed during prosecution of EP3167051, dated Aug. 17, 2017, 1 page.
Experimental data showing that the claimed sunflower plants are resistant to downy mildew, filed during prosecution of EP3024929, dated Dec. 21, 2017, 2 pages.
Fall et al., (2015). "Infection Efficiency of Four Phytophthora infestans Clonal Lineages and DNA-based Quantification of Sporangia," PLoS ONE, 10(8): e0136312doi: 10.1371/journal.pone.0136312, 18 pages.
Ferreyra et al., (2015). "The Identification of Maize and Arabidopsis Type I Flavone Synthases Links Flavones with Hormones and Biotic Interactions," Plant Physiology, 169:1090-1107.
Fischer et al., (Feb. 2004). "Quantitative Trait Locus Analysis of Fungal Disease Resistance Factors on a Molecular Map of Grapevine", Theoretical and Applied Genetics, 108(3):501-515.
Flanagan et al., (2010). "Using SIFT and PolyPhen to predict loss-of-function and gain-of-function mutations", Genetic Testing and Molecular Biomarkers, 14(4):533-537.
Forkmann et al. (1980). "Anthocyanin Biosynthesis in Flowers of Matthiola incana Flavanone 3-and Flavonoid 3'-Hydroxylases," Z. Naturforsch. 35 c, 691-695. DOI: https://doi.org/10.1515/znc-1980-9-1004.
Franchel et al., (2013). "Positional cloning of a candidate gene for resistance to the sunflower downy mildew, Plasmopara halstedii race 300", Theoretical and Applied Genetics, 126(2):359-367.
Friedrich et al., (2001). "NIM1 Overexpression in Arabidopsis Potentiates Plant Disease Resistance and Results in Enhanced Effectiveness of Fungicides", MPMI, 14(9):1114-1124.
Further experimental data of pathogen resistance against Phytophthora infestans of mutated tomato plants, filed during Opposition against EP2455479, dated Jan. 4, 2019, 2 pages.
Gaspero et al., (2002). "Resistance Gene Analogs are Candidate Markers for Disease-Resistance Genes in Grape (Vitis spp.)", Theoretical and Applied Genetics, 106(1):163-172.
Geneseq Database Accession No. AAG45151, Oct. 18, 2000, 4 pages.
Giovanini et al., (2006). "Gene-for-gene defense of wheat against the Hessian fly lacks a classical oxidative burst", Molecular Plant-Microbe Interactions, 19(9):1023-1033.
Göker et al., (2003). "Taxonomic aspects of Peronosporaceae inferred from Bayesian molecular phylogenetics", Canadian Journal of Botany, 81(7):672-683.
Göker et al., (2004). "Phylogeny of Hyaloperonospora based on nuclear ribosomal internal transcribed spacer sequences", Mycological Progress, 3(2):83-94.
Grimplet et al., (2007). "Tissue-Specific mRNA Expression Profiling in Grape Berry Tissues", BMC Genomics, 8(187):1-23.
Gurr et al., (2005). "Engineering plants with increased disease resistance: how are we going to express it?" Trends Biotechnol., 23(6):283-290.
Gurr et al., (2005). "Engineering plants with increased disease resistance: what are we going to express?" Trends Biotechnology, 23(6):275-282.
Guzzo, Silvia Dias (2004). "Isolation of cv. Mundo Novo coffee plant genes associated with systemic acquired resistance", 21 pages (including 10 pages of English translation).
Hellens et al., (2000). "pGreen: a Versatile and Flexible Binary Ti vector for Agrobacterium-Mediated Plant Transformation", Plant Molecular Biology, 42:819-832.
Henikoff et al., (2004). "Tilling. Traditional Mutagenesis Meets Functional Genomics", Plant Physiology, 135:630-636.
Holub et al., (1994). "Phenotypic and Genotypic Characterization of Interactions Between Isolates of Peronospora parasitica and Accessions of *Arabidopsis thaliana*", 7(2):223-239.
Hong et al., (2008). "First confirmed report of downy mildew caused by Hyaloperonospora parasitica on broccoli in Korea", Plant Pathology, 57(4):777.
Instructions to the PhD candidate, filed Jul. 17, 2017, in Opposition against EP2455473, Utrecht University, 11 pages.
International Seed Federation Guidelines for Coding Pests of Vegetable and Cereal Crops, submitted in Opposition against EP2455477, dated Jan. 18, 2018, 4 pages.
Irish et al., (2007). "Three new races of the spinach downy mildew pathogen identified by a modified set of spinach differentials," Plant Disease, 91(11):1392-1396.
Jacobs et al., (2015). "Targeted genome modifications in soybean with CRISPR/Cas9," BMC Biotechnology, 15(1):16, 10 pages.

(56) References Cited

OTHER PUBLICATIONS

Karimi et al., (2002). "Gateway Vectors for Agrobacterium-Mediated Plant Transformation", Trends in Plant Science, 7(5):193-195.
Kim et al., (2006). "Characterization of Late Blight Resistance Derived from Solanum pimpinellifolium L3708 against Multiple Isolates of the Pathogen Phytophthora infestans", Journal of the American Society for Horticultural Science, 131(5):637-645.
Kitz, Leilani, (2008). "Evaluation of Downy Mildew (Peronospora farinosa f. sp. chenopodii) Resistance among Quinoa Genotypes and Investigation of P. farinosa Growth using Scanning Electron Microscopy", All Theses and Dissertations, Brigham Young University, 89 pages.
Kofoet et al., (1990). "Inheritance of Resistance to Downy Mildew (Peronospora Destructor [Berk.] Casp.) from Allium Roylei Stearn in the Backcross Allium Cepa L. x (A. Roylei xA. Cepa)", Plant Breeding, 105(2):144-149.
Kofoet et al., (1990). "Resistance to Downy Mildew (Peronospora Destructor (Berk.) Casp.) in Allium Species//Resistenz Gegen Falschen Mehltau (Peronospora Destructor (Berk.) Casp.) in Allium- Arten," Zeitschrift fuer Pflanzenkrankheiten und Pflanzenschutz//Journal of Plant Diseases and Protection, 97(1):13-23.
Kortekamp et al., (2006). "Expression Analysis of Defence-Related Genes in Grapevine Leaves after Inoculation with a Host and a Non-Host Pathogen", Plant Physiology and Biochemistry, 44(1):58-67.
Ku et al., (2000). "Comparing Sequenced Segments of the Tomato and Arabidopsis Genomes: Large-Scale Duplication Followed by Selective Gene Loss Creates a Network of Synteny", PNAS, 97(16):9121-9126.
Lacomme et al., (1999). "Bax-induced cell death in tobacco is similar to the hypersensitive response", Proc. Natl. Acad. Sci. 96(14):7956-7961.
Lamour et al., (2009). "Oomycete Genetics and Genomics: Diversity, Interactions and Research Tools", Wiley-Blackwell, 6 pages.
Lebeda, Ales, (1992). "Screening of wild cucumis species against downy mildew (Pseudoperonospora cubensis) isolates from cucumbers", Phytoparasitica, 20(3):203-210.
Lee et al., (1999). "Identification of the Gene Encoding Homoserine Kinase from *Arabidopsis Thaliana* and Characterization of the Recombinant Enzyme derived from the Gene", Arch. Biochem. Biophys., 372(1):135-142.
Lee et al., (2005). "Methionine and Threonine Synthesis are Limited by Homoserine availability and not the Activity of Homoserine Kinase in *Arabidopsis Thaliana*", The Plant Journal, 41:685-696.
Letter accompanying subsequently filed items, filed during prosecution of EP2455473, dated Mar. 10, 2014, 1 page.
Letter accompanying subsequently filed items, filed during prosecution of EP2455474, dated Mar. 10, 2014, 1 page.
Letter accompanying subsequently filed items, filed during prosecution of EP2455475, dated Mar. 10, 2014, 1 page.
Letter accompanying subsequently filed items, filed during prosecution of EP2455476, dated Mar. 10, 2014, 1 page.
Letter accompanying subsequently filed items, filed during prosecution of EP2455477, dated Mar. 10, 2014, 1 page.
Letter accompanying subsequently filed items, filed during prosecution of EP2455481, dated Mar. 10, 2014, 1 page.
Letter accompanying subsequently filed items, filed during prosecution of EP2455482, dated Mar. 10, 2014, 1 page.
Letter regarding the opposition procedure (no time limit) and Auxiliary requests I and II, filed during Opposition against EP2455477, dated Dec. 8, 2017, 22 pages.
Letter regarding the opposition procedure (no time limit), filed during Opposition against EP2455473, dated Sep. 14, 2017, 3 pages.
Letter regarding the opposition procedure (no time limit), filed during Opposition against EP2455473, dated Sep. 15, 2017, 17 pages.
Letter regarding the opposition procedure (no time limit), filed during Opposition against EP2455477, dated Jan. 18, 2018, 15 pages.
Letter regarding the opposition procedure and Auxiliary requests I and II, filed during Opposition against EP2455474, dated Dec. 14, 2018, 39 pages.
Letter regarding the opposition procedure and Auxiliary requests I and II, filed during Opposition against EP2455479, dated Jan. 8, 2019, 48 pages.
Li et al., (2016). "Loci and candidate gene identification for resistance to Phytophthora sojae via association analysis in soybean [Glycine max (L.) Merr.]," Molecular Genetics and Genomics, 291(3):1095-1103.
Lukacin et al., (1997). "Identification of strictly conserved histidine and arginine residues as part of the active site in Petunia hybrida flavanone 3P-hydroxylase," Eur. J. Biochem., 249:748-757.
Mae et al., (2001). "Transgenic Plants Producing the Bacterial Pheromone N-Acyl-Homoserine Lactone Exhibit Enhanced Resistance to the Bacterial Phytopathogen Erwinia Carotovora", Molecular Plant-Microbe Interactions, 14(9):1035-1042.
Matvienko et al. (2011). Locus JI1587921, TSA: Lactuca sativa Letassy_X1_9021 mRNA sequence, direct submission to Genome Center, University of California Davis, Genome and Biomedical Sciences Facility, 2 pages.
McCallum et al., (2000). "Targeted Screening for Induced Mutations", Nature Biotechnology, 18:455-457.
Meer et al., (1990). "An Interspecific Cross between Allium Roylei Stearn and Allium Cepa L, and its Backcross to A. Cepa", Euphytica, 47:29-31.
Mosher et al., (2006). "A Comprehensive Structure-Function Analysis of Arabidopsis SNI1 Defines Essential Regions and Transcriptional Repressor Activity", The Plant Cell, 18:1750-1765.
mRNA sequence ID XM_008464687.2 corresponding to melon DMR6 protein sequence ID XP_008462909.2, filed on Apr. 29, 2019 in Opposition proceedings against EP2455475, 2 pages.
Multiple alignment of cabbage DMR6 (B. oleracea) with known oxidoreductases, filed May 22, 2017, in Opposition against EP2455477, 2 pages.
Multiple alignment of spinach DMR6 (S. oleracea) with known oxidoreductases, filed Feb. 14, 2017, in Opposition against EP2455473, 1 page.
Nakashima et al. (2018). "Structure function and engineering of multifunctional non-heme iron dependent oxygenases in fungal meroterpenoid biosynthesis," Nature Communication, 9:104, 10 pages.
NCBI Reference Sequence NP_190692.1, dated Jul. 3, 2013, filed in Opposition against EP2455473 and during prosecution for EP2455474 and EP2455479, 1 page.
NCBI Reference Sequence NP_197841.1, dated Nov. 25, 2016, filed in Opposition against EP2455473 and during prosecution for EP2455474 and EP2455479, 2 pages.
Notice of appeal by Bird&Bird, filed in relation to EP2455473, dated Feb. 22, 2018, 2 pages.
Notice of appeal by Bird&Bird, filed in relation to EP2455477, dated Jul. 19, 2018, 2 pages.
Nowicki et al., (2012). "Potato and Tomato late blight caused by Phytophthora infestans: an overview of pathology and resistance breeding," Plant Disease, 96(1):4-17.
Official variety description spinach variety Bandola by the Naktuinbouw (1995), filed in Opposition against EP2455473, 1 page.
Official variety description spinach variety Maracas by the Naktuinbouw (1950), filed in Opposition against EP2455473, 1 page.
Official variety description spinach variety Marimba by the Naktuinbouw (1950), filed in Opposition against EP2455473, 1 page.
Official variety description spinach variety Symphony by the Naktuinbouw (1950), filed in Opposition against EP2455473, 3 pages.
Pacific Pests and Pathogens Fact Sheet on cabbage downy mildew, dated Sep. 20, 2017, 3 pages.
Parker et al., (1996). "Characterization of eds1, a mutation in Arabidopsis suppressing resistance to Peronospora parasitica specified by several different RPP genes", Plant Cell, American Society of Plant Physiologists, 8(11):2033-2046.

(56) References Cited

OTHER PUBLICATIONS

Partial set of drawings filed in response to formal objections, filed during prosecution of EP2455474, dated Mar. 13, 2012, 4 pages.
Partial set of drawings filed in response to formal objections, filed during prosecution of EP2455475, dated Mar. 13, 2012, 4 pages.
Partial set of drawings filed in response to formal objections, filed during prosecution of EP2455476, dated Mar. 13, 2012, 4 pages.
Partial set of drawings filed in response to formal objections, filed during prosecution of EP2455477, dated Mar. 13, 2012, 4 pages.
Partial set of drawings filed in response to formal objections, filed during prosecution of EP2455478, dated Mar. 13, 2012, 4 pages.
Partial set of drawings filed in response to formal objections, filed during prosecution of EP2455479, dated Mar. 13, 2012, 4 pages.
Partial set of drawings filed in response to formal objections, filed during prosecution of EP2455480, dated Mar. 13, 2012, 4 pages.
Partial set of drawings filed in response to formal objections, filed during prosecution of EP2455481, dated Mar. 13, 2012, 4 pages.
Partial set of drawings filed in response to formal objections, filed during prosecution of EP2455482, dated Mar. 13, 2012, 4 pages.
Partial set of drawings filed in response to formal objections, filed during prosecution of EP2455483, dated Mar. 13, 2012, 4 pages.
Perchepied et al., (2005). "Relationship Between Loci Conferring Downy Mildew and Powdery Mildew Resistance in Melon Assessed by Quantitative Trait Loci Mapping", Phytopathology, 95(5):556-565.
Pihlajamaa, Heli, Presentation slides taken from conference documentation, Presentation at the 8th conference on Intellectual Property Protection for Plant Innovation 2017, p. 197-205.
Preliminary Amendment, filed for U.S. Appl. No. 15/975,670, dated Jul. 23, 2018, 5 pages.
Preliminary Amendment, filed for U.S. Appl. No. 16/055,697, dated Aug. 6, 2018, 9 pages.
Preliminary Amendment, filed for U.S. Appl. No. 16/450,881, dated Jun. 25, 2019, 6 pages.
Preliminary Amendment, filed for U.S. Appl. No. 16/642,257, dated Feb. 26, 2020, 8 pages.
Preliminary Amendment, filed for U.S. Appl. No. 16/659,470, dated Dec. 12, 2019, 6 pages.
Primrose et al., (2006). "Principles of Gene Manipulation and Genomics," Chapter 9 of Bioinformatics, Blackwell Publishing, 21 pages.
Protocol for Distinctness, Uniformity and Stability Tests for Spinacea oleracea L. (2002). European Union Community Plant Variety Office, Final CPVO-TP-55-6 Final, 17 pages.
Qin et al., (2014). "Whole-Genome Sequencing of Cultivated and Wild Peppers Provides Insights into Capsicum Domestication and Specialization," PNAS, 111(14):5135-5140.
Radwan et al., (2011). "Molecular Characterization of Two Types of Resistance in Sunflower to Plasmopara halstedii, the Causal Agent of Downy Mildew", The American Phytopathological Society, 101(8):970-979.
Reply of the patent proprietor to the notice(s) of opposition dated Apr. 29, 2019, filed in Opposition against EP2455475, 38 pages.
Reply of the patent proprietor to the notice(s) of opposition dated Feb. 13, 2017, filed during Opposition against EP2455473, 28 pages.
Reply of the patent proprietor to the notice(s) of opposition dated Jul. 11, 2014, filed during Opposition against EP2115147, 5 pages.
Reply of the patent proprietor to the notice(s) of opposition dated May 22, 2017, filed during Opposition against EP2455477, 30 pages.
Reply to appeal by Bird&Bird filed in relation to EP2455473, dated Sep. 10, 2018, 40 pages.
Reply to Canadian Office Action dated Jun. 29, 2020 and Amended Claims, filed Oct. 20, 2020, during prosecution of Canadian Patent Application No. 2918706, 14 pages.
Reply to communication from the Examining Division, filed during prosecution of EP2115147, dated Aug. 20, 2010, 4 pages.
Reply to communication from the Examining Division, filed during prosecution of EP2115147, dated Feb. 2, 2012, 3 pages.
Reply to communication from the Examining Division, filed during prosecution of EP2115147, dated Jun. 5, 2012, 1 page.
Reply to communication from the Examining Division, filed during prosecution of EP2115147, dated May 26, 2011, 3 pages.
Reply to communication from the Examining Division, filed during prosecution of EP2455473, dated Jul. 4, 2013, 4 pages.
Reply to communication from the Examining Division, filed during prosecution of EP2455473, dated Oct. 21, 2013, 1 page.
Reply to communication from the Examining Division, filed during prosecution of EP2455474, dated Dec. 8, 2015, 7 pages.
Reply to communication from the Examining Division, filed during prosecution of EP2455474, dated Jul. 4, 2013, 4 pages.
Reply to communication from the Examining Division, filed during prosecution of EP2455474, dated Mar. 17, 2017, 2 pages.
Reply to communication from the Examining Division, filed during prosecution of EP2455475, dated Dec. 8, 2015, 7 pages.
Reply to communication from the Examining Division, filed during prosecution of EP2455475, dated Jul. 5, 2013, 4 pages.
Reply to communication from the Examining Division, filed during prosecution of EP2455476, dated Dec. 3, 2015, 7 pages.
Reply to communication from the Examining Division, filed during prosecution of EP2455476, dated Jul. 5, 2013, 4 pages.
Reply to communication from the Examining Division, filed during prosecution of EP2455477, dated Jul. 5, 2013, 4 pages.
Reply to communication from the Examining Division, filed during prosecution of EP2455477, dated Oct. 21, 2013, 1 page.
Reply to communication from the Examining Division, filed during prosecution of EP2455478, dated Dec. 11, 2015, 7 pages.
Reply to communication from the Examining Division, filed during prosecution of EP2455478, dated Jul. 5, 2013, 4 pages.
Reply to communication from the Examining Division, filed during prosecution of EP2455479, dated Dec. 8, 2015, 7 pages.
Reply to communication from the Examining Division, filed during prosecution of EP2455479, dated Jul. 5, 2013, 4 pages.
Reply to communication from the Examining Division, filed during prosecution of EP2455480, dated Dec. 3, 2015, 7 pages.
Reply to communication from the Examining Division, filed during prosecution of EP2455480, dated Jul. 8, 2013, 5 pages.
Reply to communication from the Examining Division, filed during prosecution of EP2455481, dated Dec. 3, 2015, 7 pages.
Reply to communication from the Examining Division, filed during prosecution of EP2455482, dated Jul. 8, 2013, 5 pages.
Reply to communication from the Examining Division, filed during prosecution of EP2455483, dated Jul. 8, 2013, 5 pages.
Reply to communication from the Examining Division, filed during prosecution of EP3024929, dated Oct. 15, 2018, 2 pages.
Reply to communication from the Examining Division, filed during prosecution of EP3094722, dated Jan. 17, 2018, 2 pages.
Reply to communication from the Examining Division, filed during prosecution of EP3094722, dated May 28, 2018, 1 page.
Reply to communication from the Examining Division, filed during prosecution of EP3167051, dated Apr. 17, 2018, 2 pages.
Reply to communication from the Examining Division, filed during prosecution of EP3167051, dated May 28, 2018, 1 page.
Reply to First Examination Report dated Feb. 25, 2020 and Amended Claims, filed Jul. 14, 2020 during prosecution of Indian Patent Application No. 201747001416, 8 pages.
Reply to First Examination Report dated Nov. 8, 2019 and Amended Claims, filed Dec. 19, 2019 during prosecution of Indian Patent Application No. 201647027274, 6 pages.
Reply to Japanese Office Action dated Apr. 1, 2019, filed Jun. 20, 2019 during prosecution of Japanese Patent Application No. 2016-528486, 8 pages.
Reply to Japanese Office Action dated Jun. 23, 2020 and Amended Claims, filed Aug. 31, 2020 during prosecution of Japanese Patent Application No. 2016-528486, 6 pages.
Reply to Japanese Office Action dated Mar. 27, 2018 and Amended Claims, filed Jun. 21, 2018 during prosecution of Japanese Patent Application No. 2016-528486, 12 pages.
Reply to Japanese Office Action dated May 29, 2012 and Amended Claims, filed Aug. 7, 2012 during prosecution of Japanese Patent Application No. 2008-538304, 12 pages.

(56) References Cited

OTHER PUBLICATIONS

Reply to Japanese Office Action dated Nov. 26, 2019 and Amended Claims, filed May 22, 2020 during prosecution of Japanese Patent Application No. 2019-11969, 6 pages.
Reply to Japanese Office Action dated Oct. 20, 2020 and Amended Claims, filed Oct. 30, 2020 during prosecution of Japanese Patent Application No. 2016-528486, 4 pages.
Reply to the invitation to remedy deficiencies, filed during prosecution of EP2115147, dated Jan. 27, 2010, 2 pages.
Reply to Written Opinion prepared by the EPO, filed during prosecution of EP2455473, dated Nov. 14, 2012, 3 pages.
Reply to Written Opinion prepared by the EPO, filed during prosecution of EP2455474, dated Nov. 14, 2012, 3 pages.
Reply to Written Opinion prepared by the EPO, filed during prosecution of EP2455475, dated Nov. 14, 2012, 3 pages.
Reply to Written Opinion prepared by the EPO, filed during prosecution of EP2455476, dated Nov. 14, 2012, 3 pages.
Reply to Written Opinion prepared by the EPO, filed during prosecution of EP2455477, dated Nov. 19, 2012, 3 pages.
Reply to Written Opinion prepared by the EPO, filed during prosecution of EP2455478, dated Nov. 19, 2012, 3 pages.
Reply to Written Opinion prepared by the EPO, filed during prosecution of EP2455480, dated Nov. 19, 2012, 3 pages.
Reply to Written Opinion prepared by the EPO, filed during prosecution of EP2455481, dated Nov. 19, 2012, 3 pages.
Request for further processing, filed during prosecution of EP3024929, dated Dec. 21, 2017, 2 pages.
Request for interpreters during oral proceedings, dated Sep. 14, 2017, filed during Opposition against EP2455473, 5 pages.
Request for Trial and Appeal, and Amended Claims, filed Aug. 8, 2013 during prosecution of Japanese Patent Application No. 2008-538304, 2 pages.
Request for Trial and Appeal, and Amended Claims, filed Jan. 28, 2019 during prosecution of Japanese Patent Application No. 2016-528486, 13 pages.
Response to Final Office Action, filed for U.S. Appl. No. 15/314,778, dated Aug. 26, 2019, 10 pages.
Response to Non-Final Office Action, filed for U.S. Appl. No. 15/594,293, dated Feb. 28, 2019, 11 pages.
Response to Notice to File Missing Parts in a Nonprovisional Application and Preliminary Amendment, filed for U.S. Appl. No. 16/773,781, dated Apr. 10, 2020, 6 pages.
Rijk Zwaan General Information Website, dated Jul. 11, 2014, filed in Opposition proceedings against EP2115147, Available Online at <http://www.rijkzwaan.com/wps/wcm/connect/RZ+Corporate/Rijk+Zwaan/Company/About+US/General+Information>, 1 page.
Rostas et al., (2013). "Copper and Herbivory Lead to Priming and Synergism in Phytohormones and Plant Volatiles in the Absence of Salicylate-Jasmonate Antagonism", Plant Signaling & Behavior, 8(6): e24264-1-e24264-3.
Rothrock et al., (2006). "Identification of Pythium-Resistant Cold-Tolerant Rice Germplasm through Controlled Environmental and Field Evaluations," Proceedings of the Thirty-First Rice Technical Working Group, Retrieved from the Internet http://www.uaex.edu/rtwg/Proceedings/2006/RTWG%20Proc%202006.pdf, [retrieved on Apr. 24, 2012], pp. 108-109.
Russell, G. E., (1966). "Some effects of inoculation with yellowing viruses on the susceptibility of sugar beet to fungal pathogens: I. Susceptibility to Peronospora farinosa", Transactions of the British Mycological Society, 49(4):611-619.
Sabetta et al., (2011). "sunTILL: a TILLING resource for gene function analysis in sunflower", Plant Methods 2011, 7(20):1-13.
Sandhu et al., (2005). "Soybean Phytophthora Resistance Gene Rps8 Maps Closely to the Rps3 Region", Journal of Heredity, 96(5): 536-541.
Schlegel, Rolf H.J. (2003). Encyclopedic dictionary of plant breeding and related subjects, Haworth Press Inc., Binghamton, New York, p. 234-237.
Sequence alignment of Spinacia oleracea DMR6 gene (Seq ID 80) and DMR6 protein (Seq ID 81) from EP2455473 with an alternative Spinacia oleracea DMR6 gene and DMR6 protein as identified in Spinacia oleracea L. accession SPI 173 (IPK, Gatersleben, Germany) and a number of spinach varieties, filed Aug. 24, 2016, in Opposition against EP2455473, 2 pages.
Sim et al., (2012). "SIFT web server: predicting effects of amino acid substitutions on proteins", Nucleic Acids Res., 40, Web Server issue, 6 pages.
Sinapidou et al., (2004). "Two TIR:NB:LRR Genes are Required to Specify Resistance to Peronospora Parasitica Isolate Cala2 in Arabidopsis", The Plant Journal, 38(6):898-909.
Skadhauge et al., (1997). "The role of the barley testa layer and its flavonoid content in resistance to Fusarium infections", Carlsberg Laboratory, Department of Physiology, 126:147-160.
Smart et al., "Best Control of Downy Mildew in Cole Crops", Dept. of Plant Pathology and Plant-Microbe Biology, Cornell University, Geneva NY, filed Dec. 8, 2017, in Opposition against EP2455477, 2 pages.
Solanum tuberosum naringenin, 2-oxoglutarate 3-dioxygenase-like (LOC102590513), mRNA, Dec. 12, 2013, cited in Chinese Application No. 2014800731630 Office Action dated Feb. 19, 2019, 2 pages.
Solanum tuberosum naringenin, 2-oxoglutarate 3-dioxygenase-like (LOC102604390), mRNA, Dec. 12, 2013, cited in Chinese Application No. 2014800731630 Office Action dated Feb. 19, 2019, 2 pages.
Somssich et al., (2003). "Closing another gap in the plant SAR puzzle," Cell, 113(7):815-816.
Statement of grounds of appeal by Bird&Bird, filed in relation to EP2455473, dated Apr. 26, 2018, 10 pages.
Submission by the proprietor in opposition proceedings for case EP2455474 dated May 28, 2020, concerning the staying of opposition proceedings, 5 pages.
Submission by the proprietor in opposition proceedings for case EP2455475 dated May 28, 2020, concerning the staying of opposition proceedings, 5 pages.
Submission by the proprietor in opposition proceedings for case EP2455479 dated May 28, 2020, concerning the staying of opposition proceedings, 5 pages.
Summary of the legal entity "Rijk Zwaan Zaadteelt en Zaadhandel B.V." obtained from the Dutch Chamber of Commerce, filed Jul. 11, 2014, in Opposition against EP2115147, 4 pages.
Summons to attend Oral Proceedings for case EP2455475, dated Mar. 22, 2016, in order to discuss outstanding objections under Articles 56 and 83 EPC, 7 pages.
Summons to attend Oral Proceedings pursuant to Rule 115(1) EPC, filed in Opposition against EP2455474, dated Jul. 13, 2016, 1 page.
Summons to attend Oral Proceedings pursuant to Rule 115(1) EPC, filed in Opposition against EP2455479, dated May 31, 2016, 5 pages.
Sun et al., (2016). "Silencing of Six Susceptibility Genes Results in Potato Late Blight Resistance", Transgenic Research, 25: 731-742 (with 12 pages of Supplementary Copy).
Szwacka et al., (2002). "Variable properties of transgenic cucumber plants containing the thaumatin II gene from Thaumatococcus daniellii", Acta Physiologiae Plantarum, 24(2):173-185.
Table 1: Spinach DMR6 mutants presented in 018, filed in Opposition against EP2455473, dated Oct. 20, 2017, 1 page.
Table on insufficiency of disclosure issues, filed Jul. 18, 2018, in Opposition against EP2455479, 3 pages.
Table on insufficiency of disclosure issues, filed Jul. 30, 2018, in Opposition against EP2455474, 3 pages.
Table on insufficiency of disclosure issues, filed Oct. 1, 2018, in Opposition against EP2455475, 3 pages.
Table with all insufficiency of disclosure issues, filed Apr. 26, 2018, in Appeal against EP2455473, 3 pages.
Takatsuji, Hiroshi, (2014). "Development of Disease-Resistant Rice Using Regulatory Components of Induced Disease Resistance", Frontiers in Plant Science, 5(630):12 pages.
Third Party Observations, filed in Opposition against EP 2455474, dated Feb. 9, 2017 for EP Application No. 12155887, 2 pages.
Thomas et al., (1992). "Resistance to Race 2 of Peronospora parasitica in U.S. Plant Introductions of *Brassica oleracea* var. capitata," HortScience, 27(10):1120-1122.

(56) References Cited

OTHER PUBLICATIONS

Thomas et al., (2000). "Linkage of random amplified polymorphic DNA markers to downy mildew resistance in cucumber (Cucumis sativus L.)", Euphytica, 115(2):105-113.
Thomazella et al., (2016). "CRISPR-Cas9 Mediated Mutagenesis of a DMR6 Ortholog in Tomato Confers Broad-Spectrum Disease Resistance", bioRxiv doi: 10.1101/064824, pp. 1-23.
Till et al., (2004). "Mismatch cleavage by single-strand specific nucleases", Nucleic Acids Research, 32(8):2632-2641.
Tor et al., (2004). "Arabidopsis Downy Mildew Resistance Gene RPP27 Encodes a Receptor-Like Protein Similar to CLAVATA2 and Tomato Cf-9 1", Plant Physiology, 135:1100-1112.
TWV/40/11, "Report of the Technical Working Party for Vegetables," Jun. 16, 2006, UPOV, 40th session, Mexico, 57 pages.
UniProt, XP002730065, retrieved from EBI Accession No. UNIPROT:M0ZIQ1 Database Accession No. M0ZIQ1 Sequence, 2 pages.
UniProt, XP002730066, retrieved from EBI Accession No. UNIPROT:M1CK41 Database Accession No. M1CK41 Sequence, 2 pages.
UniProt, XP002730067, retrieved from EBI Accession No. UNIPROT:K4C928, Database Accession No. K4C928 sequence, 2 pages.
Vailleau et al., (2002). "A R2R3-MYB gene, AtMYB30, acts as a positive regulator of the hypersensitive cell death program in plants in response to pathogen attack", PNAS, 99(15):10179-10184.
Van Damme et al., (2005). "Identification of *Arabidopsis* loci Required for Susceptibility to the Downy Mildew Pathogen Hyaloperonospora parasitica", Molecular Plant-Microbe Interactions, 18(6):583-592.
Van Damme et al., (2008). "Arabidopsis DMR6 encodes a putative 2OG-Fe(II) oxygenase that is defense-associated but required for susceptibility to downy mildew", The Plant Journal, 54:785-793.
Van Damme et al., (2009). "Downy Mildew Resistance in Arabidopsis by Mutation of Homoserine Kinase", The Plant Cell, 21:2179-2189.
Van Damme, Mireille, (2007). "Genetic analysis of disease susceptibility in the Arabidopsis-Hyaloperonospora parasitica interaction," Thesis, 134 pages.
Vandenbussche et al., (2008). "Generation of a 3D Indexed Petunia Insertion Database for Reverse Genetics", The Plant Journal, 54(6):1105-14.
Vicente et al., (2013). "Xanthomonas campestris pv. campestris (cause of black rot of crucifers) in the genomic era is still a worldwide threat to brassica crops," Molecular Plant Pathology, 14(1): 2-18.
Vogel et al., (2002). "PMR6, a Pectate Lyase-Like Gene Required for Powdery Mildew Susceptibility in Arabidopsis", The Plant Cell, 14:2095-2106.
Vogel et al., (2013). "Insights into the regulation of protein abundance from proteomic and transcriptomic analyses," Nat. Rev. Genet., 13(4):227-232.
Voglmayr, Hermann, (2003). "Phylogenetic relationships of Peronospora and related genera based on nuclear ribosomal ITS sequences", Mycol. Res., 107(10):1132-1142.
Weaver et al., (2006). "The *Arabidopsis thaliana* TIR-NB-LRR R-protein, RPP1A; protein localization and constitutive activation of defence by truncated alleles in tobacco and Arabidopsis," The Plant Journal, 47:829-840.
Wikipedia, "Expressed sequence tag", website as of Dec. 11, 2018, available online at <https://en.wikipedia.org/wiki/Expressed_sequence_tag>, filed during opposition of EP2455479, 4 pages.
Wikipedia, "Gene silencing", website as of Jul. 10, 2018, available online at <https://en.wikipedia.org/wiki/Gene_silencing>, filed during opposition of EP2455479, 12 pages.
Wikipedia, "Hyaloperonospora Brassicae", website as of Sep. 20, 2017, available online at <https://en.wikipedia.org/wiki/Hyaloperonospora_brassicae>, filed during opposition of EP2455477, 2 pages.
Wikipedia, "Hyaloperonospora Parasitica", website as of Sep. 20, 2017, available online at <https://en.wikipedia.org/wiki/Hyaloperonospora_parasitica>, filed during opposition of EP2455477, 3 pages.
Wilmouth et al., (2002). "Structure and Mechanism of Anthocyanidin Synthase from *Arabidopsis thaliana*," Structure, 10:93-103.
Withdrawal of a request for oral proceedings, filed during prosecution of EP2455482, dated Jan. 8, 2016, 1 page.
Withdrawal of a request for oral proceedings, filed during prosecution of EP2455483, dated Jan. 8, 2016, 1 page.
Withdrawal of an appeal, filed during appeal of EP2455477, dated Sep. 20, 2018, 1 page.
Written submission in preparation to/during oral proceedings, filed during prosecution of EP2455474, dated Oct. 10, 2016, 2 pages.
Written submission in preparation to/during oral proceedings, filed during prosecution of EP2455475, dated Aug. 30, 2016, 3 pages.
Written submission in preparation to/during oral proceedings, filed during prosecution of EP2455476, dated Jul. 21, 2016, 4 pages.
Written submission in preparation to/during oral proceedings, filed during prosecution of EP2455478, dated Oct. 10, 2016, 2 pages.
Written submission in preparation to/during oral proceedings, filed during prosecution of EP2455479, dated Oct. 5, 2016, 4 pages.
Written submission in preparation to/during oral proceedings, filed during prosecution of EP2455480, dated Jul. 21, 2016, 4 pages.
Written submission in preparation to/during oral proceedings, filed during prosecution of EP2455481, dated Aug. 30, 2016, 3 pages.
Written submission in preparation to/during oral proceedings, filed during prosecution of EP2455482, dated Oct. 13, 2015, 8 pages.
Written submission in preparation to/during oral proceedings, filed during prosecution of EP2455483, dated Oct. 13, 2015, 8 pages.
Xu et al., (2011). "Genome Sequence and Analysis of the Tuber Crop Potato", Nature, 475:189-195.
Yang et al., (2005). "Characterization and Mapping of Rpi1, a Gene that Confers Dominant Resistance to Stalk Rot in Maize", Molecular Genetics and Genomics, 274(3):229-234.
Zeilmaker et al., (2015). "Downy Mildew Resistant 6 and DMR6-LIKE Oxygenase 1 are Partially Redundant but Distinct Suppressors of Immunity in Arabidopsis", The Plant Journal, 81(2):210-222.
Zeilmaker, Tieme, (2012). Functional and Applied Aspects of the Downy Mildew Resistant 1 and 6 Genes in Arabidopsis, Universiteit Utrecht, Available at <http://web.science.uu.nl/pmi/publications/PDF/2012/Proefschrift-Zeilmaker-2012.pdf>, 147 pages.
Zhang et al., (2013). "Salicylic Acid 3-Hydroxylase Regulates Arabidopsis Leaf Longevity by Mediating Salicylic Acid Catabolism", Proceedings of The National Academy of Sciences of the United States of America, 110(36):1-6.
Zhang et al., (2017). "S5H/DMR6 Encodes a Salicylic Acid 5-Hydroxylase that Fine-Tunes Salicylic Acid Homeostasis," Plant Physiology Preview, DOI:10.1104/pp.17.00695, 41 pages.
Zhang, James Z. (2003). "Overexpression analysis of plant transcription factors", Curr. Opin. Plant Biol., 6(5):430-440.
Zimmermann et al., (2005). "Gene-expression analysis and network discovery using Genevestigator", Trends Plant Sci., 10(9):407-409.
Reply to Canadian Office Action dated Apr. 13, 2021 and Amended Claims, filed Aug. 10, 2021, during prosecution of Canadian Patent Application No. 2918706, 10 pages.
Reply to Indian First Examination Report dated Jun. 29, 2021 and Amended Claims, filed Dec. 17, 2021 during prosecution of Indian Patent Application No. 202048010647, 6 pages.
Reply to Indian Office Action dated Dec. 20, 2021 and Amended Claims, filed Dec. 27, 2021 during prosecution of Indian Patent Application No. 201747001416, 3 pages.
Reply to Indian Office Action dated Jun. 25, 2021 and Amended Claims, filed Jun. 25, 2021 during prosecution of Indian Patent Application No. 201747001416, 20 pages.
Response to Final Office Action, filed for U.S. Appl. No. 16/361,089, dated Apr. 20, 2021, 7 pages.
"Prosecution History of European Patent Application No. 08707413.4" 414 pages.
"Prosecution History of European Patent Application No. 12155885.2" 1335 pages.

(56) References Cited

OTHER PUBLICATIONS

"Prosecution History of European Patent Application No. 12155885. 2" 404 pages.
"Prosecution History of European Patent Application No. 12155893. 6" 1257 pages.
"Prosecution History of European Patent Application No. 12155893. 6" 161 pages.
de Jong et al., "Membrance-Associated Transcripts in Arabidopsis; Their Isolation and Characterization by DNA Microarray Analysis and Bioinformatics," The Plant Journal, vol. 46, 2006, pp. 708-721.
de las Mercedes, Dana et al., "Transgenic Tobacco Plants Overexpressing Chitinases of Fungal Origin Show Enhanced Resistance to Biotic and Abiotic Stress Agents," Plant Physiology, vol. 142, Oct. 2006, pp. 722-730.
EBI Accession No. AF082525, Available at <http://www.ebi.ac.uk/ena/data/view/AF082525&display=text>, Jun. 1, 1999, 2 pages.
EBI Database Accession No. DQ208192, Available at <http://www.ebi.ac.uk/ena/data/view/ABB20895&display=text>, Sep. 6, 2006, 2 pages.
Elliott, Charlotte, "Relative Susceptibility to Pythium Root Rot of Twelve Dent Corn Inbreds," Journal of Agricultural Research, vol. 64, No. 12, Jun. 15, 1992, pp. 711-723.
Non-Final Office Action received for U.S. Appl. No. 15/111,285, mailed Feb. 7, 2018, 13 pages.
Preliminary Amendment, filed for U.S. Appl. No. 15/594,293, dated May 12, 2017, 7 pages.
Preliminary Amendment, filed for U.S. Appl. No. 15/975,670 dated Jul. 12, 2018, 5 pages.
Preliminary Amendment, filed for U.S. Application No. 15/990,182, dated Aug. 13, 2018, 5 pages.
Response to Non-Final Office Action, filed for U.S. Appl. No. 15/191,919, dated Aug. 22, 2018, 8 pages.
Response to Non-Final Office Action, filed for U.S. Appl. No. 15/314,778, dated Nov. 21, 2018, 8 pages.
Response to Restriction Requirement, filed for U.S. Appl. No. 15/314,778, dated Apr. 5, 2018, 8 pages.
Zeilmaker et al., "Downy Mildew Resistant 6 and DMR6-like Oxygenase 1 are Partially Redundant but Distinct Suppressors of Immunity in Arabidopsis," The Pant Journal, vol. 81, 2015, pp. 210-222.
Zhang et al., "Salicylic Acid 3-Hydroxylase Regulates Arabidopsis Leaf Longevity by Mediating Salicylic Acid Catabolism," Proceedings of The National Academy of Sciences of the United States of America, vol. 110, No. 36, Sep. 3, 2013, pp. 14807-14812.
Zhang, James Z., "Overexpression Analysis of Plant Transcription Factors," Curr Opin Plant Biol., vol. 6, No. 5, 2003, pp. 430-440.
Zimmermann et al., "Gene-Expression Analysis andd Network Discovery using Genevestigator," Trends Plant Sci., vol. 10, No. 9, Sep. 2005, pp. 407-409.

* cited by examiner dmr6.1 x dmr6.2 double mutant    Wild type

DISEASE RESISTANT PETUNIA PLANTS

CROSS-REFERENCE TO RELATED APPLICATIONS

This application is a continuation-in-part application of U.S. patent application Ser. No. 16/361,089, filed Mar. 21, 2019, now abandoned, which is a continuation of U.S. patent application Ser. No. 16/055,697, filed Aug. 6, 2018, now abandoned, which is a continuation of U.S. patent application Ser. No. 15/111,285, internationally filed Jan. 14, 2014, now abandoned, which is a U.S. National Phase application under 35 U.S.C. § 371 of International Application No. PCT/EP2014/050572, filed Jan. 14, 2014, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701802011921SEQLIST.TXT, date recorded: Nov. 15, 2021, size: 81,697 bytes).

TECHNICAL FIELD

The present invention relates to mutant *petunia* (*Petunia* spp.) plants including mutant dmr6.1 and dmr6.2 alleles. The mutant *petunia* plants are resistant to oomycete and fungal pathogens.

BACKGROUND

In plant breeding there is a constant struggle to identify new sources of mostly monogenic dominant resistance genes. In cultivars with newly introduced single resistance genes, protection from disease is often rapidly broken, because pathogens evolve and adapt at a high frequency and regain the ability to successfully infect the host plant. Therefore, the availability of new sources of disease resistance is highly needed.

The plant pathogen *Phytophthora* is a genus of plant-damaging Oomycetes (water molds), whose member species are capable of causing large economic losses to crops worldwide, as well as environmental damage in natural ecosystems. The genus was first described by Heinrich Anton de Bary in 1875. Approximately 100 species have been described, although an estimated 100 to 500 undiscovered *Phytophthora* species are suspected to exist. *Phytophthora* pathogens are mostly pathogens of dicotyledonous plants and generally are host-specific parasites.

Powdery mildew is a fungal disease that is caused by multiple closely related fungal species. While each fungal species has a limited plant host range, the group of powdery mildew fungi as a whole infects a wide range of plants. Many crop plants are susceptible to powdery mildew, including vegetable and cereal crops. Further, powdery mildews are some of the most common diseases of ornamental plants. Many ornamental plants grown for their flowers are susceptible to powdery mildew.

Many bedding plants are susceptible to blight, root- or crown-rot caused by *Phytophthora* species. In *petunia*, this can cause major problems after flower beds have been contaminated, as the spores will stay viable for many years, allowing re-infection. *Phytophthora nicotianae* (previously *P. parasitica*) is the primary cause of these diseases, and there is currently no robust resistance available in *petunia* varieties. In addition to *P. nicotianae*, the destructive late blight pathogen *Phytophthora infestans* has recently been shown to infect *petunia* and cause commercial damage (McLeod (2006), DOI: 10.1094/PD-90-1550B; Deahl (2003), DOI: 10.1094/PDIS.2003.87.8.1004A). *Petunia* varieties resistant to *P. infestans* are also not available. Current examples of commercial resistance to *Phytophthora* species in other solanaceous plants (e.g., potato, tomato, pepper) is usually limited to species-specific resistance to one *Phytophthora* species or to a limited set of pathogen races of one *Phytophthora* species. There is therefore a need for *petunia* plants with broad resistance to oomycete and fungal pathogens, in particular *Phytophthora* species and powdery mildew.

BRIEF SUMMARY

The present disclosure relates to *petunia* (*Petunia* spp.) plants that are resistant to both oomycete and fungal pathogens. *Petunia* plants of the present disclosure are resistant or tolerant to both *Phytophthora nicotianae* and *Phytophthora infestans*, regardless of pathogen race. Further, the *petunia* plants of the present disclosure are resistant to powdery mildew. The *petunia* plants contain mutant dmr6.1 and dmr6.2 alleles, which provide the genetic basis for the disease resistance.

Accordingly, certain aspects of the present disclosure relate to a mutant *petunia* (*Petunia* spp.) plant including a first nucleotide sequence including SEQ ID NO: 14 and a second nucleotide sequence including SEQ ID NO: 16. In some embodiments, the mutant *petunia* plant further includes a first polypeptide sequence including SEQ ID NO: 2 and a second polypeptide sequence including SEQ ID NO: 6.

In some embodiments, the mutant *petunia* plant exhibits resistance selected from the group of resistance to *Phytophthora nicotianae*, resistance to *Phytophthora infestans*, or resistance to powdery mildew. In some embodiments, the mutant *petunia* plant exhibits resistance to *Phytophthora nicotianae*. In some embodiments, the mutant *petunia* plant exhibits resistance to *Phytophthora infestans*. In some embodiments, the mutant *petunia* plant exhibits resistance to powdery mildew.

In some aspects, the present disclosure relates to a tissue or plant part of the *petunia* plant of any of the above embodiments, wherein the tissue or plant part includes the first nucleotide sequence including SEQ ID NO: 14 and the second nucleotide sequence including SEQ ID NO: 16. In some embodiments, the plant part includes a root, a stem, a leaf, a flower, a petal, an anther, a pistil, an ovule, or a pollen grain.

In some aspects, the present disclosure relates to a seed produced from the mutant *petunia* plant of any of the above embodiments.

In some aspects, the present disclosure relates to a tissue culture produced from protoplasts or cells from the mutant *petunia* plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell. In some aspects, the present disclosure relates to a *petunia* plant regenerated from the tissue culture, wherein the plant includes the first nucleotide sequence including SEQ ID NO: 14 and the second nucleotide sequence including SEQ ID NO: 16. In some embodiments, the plant further includes the first polypeptide sequence including SEQ ID NO: 2 and the second polypeptide sequence including SEQ ID NO: 6. In some embodiments, the plant exhibits resistance selected from the group of resistance to *Phytophthora nicotianae*, resistance to *Phytophthora infestans*, or resistance to powdery mildew.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows the results of a soil drench assay with *Phytophthora nicotianae* at 45 days post inoculation (dpi). The bars show percentages of living *petunia* plants at 45 dpi: white indicates dead plants, light green indicates symptomatic but alive plants, and dark green indicates alive plants with a healthy appearance. The first bar shows wild type *petunia* plants (0% living plants), the second bar shows dmr6.1 mutant *petunia* plants (20% living plants), the third bar shows dmr6.2 mutant *petunia* plants (20% living plants), and the fourth bar shows dmr6.1×dmr6.2 double mutant *petunia* plants (45% living plants). FIG. 1B is a representative image from the soil drench assay showing a comparison of wild type *petunia* plants (bottom left quadrant; within dashed blue line) and dmr6.1×dmr6.2 double mutant *petunia* plants (bottom right quadrant, top right quadrant, and top left quadrant) at 23 days post inoculation (dpi). FIG. 1C shows a close-up view of FIG. 1B, specifically the top left quadrant (dmr6.1×dmr6.2 double mutant *petunia* plants) and the bottom left quadrant (wild type *petunia* plants).

FIG. 2A shows the results of a plant spray assay with *Phytophthora nicotianae* at 10 days post infection (dpi). The bars show percentages of living *petunia* plants at 10 dpi: white indicates dead plants, light green indicates symptomatic but alive plants, and dark green indicates alive plants with a healthy appearance. The first bar shows wild type *petunia* plants (28% living plants), the second bar shows dmr6.2 mutant *petunia* plants (42% living plants), the third bar shows dmr6.1 mutant *petunia* plants (71% living plants), and the fourth bar shows dmr6.1×dmr6.2 double mutant *petunia* plants (91% living plants). FIG. 2B shows the average disease index of wild type *petunia* plants, dmr6.1 single mutant plants, dmr6.2 single mutant plants, and dmr6.1×dmr6.2 double mutant *petunia* plants inoculated with *Phytophthora nicotianae*. The x-axis shows the days post inoculation (DPI), the y-axis shows the disease score (0=no symptoms; 1=lesions on leaves; 2=rotten stems and petioles; 3=collapsed). The number of plants evaluated for each genotype (n) was 11 plants for wild type, 7 plants for dmr6.1 single mutant, 7 plants for dmr6.2 single mutant, and 18 plants for dmr6.1×dmr6.2 double mutant.

FIG. 4A shows a comparison of wild type *petunia* plants (on left and second from right) and dmr6.1×dmr6.2 double mutant *petunia* plants (second from left and on right). FIG. 4B shows a close-up view of FIG. 4A, specifically the middle of the image with the dmr6.1×dmr6.2 double mutant *petunia* plants on left and the wild type *petunia* plants on right.

DETAILED DESCRIPTION

DMR6

Figure 1A:
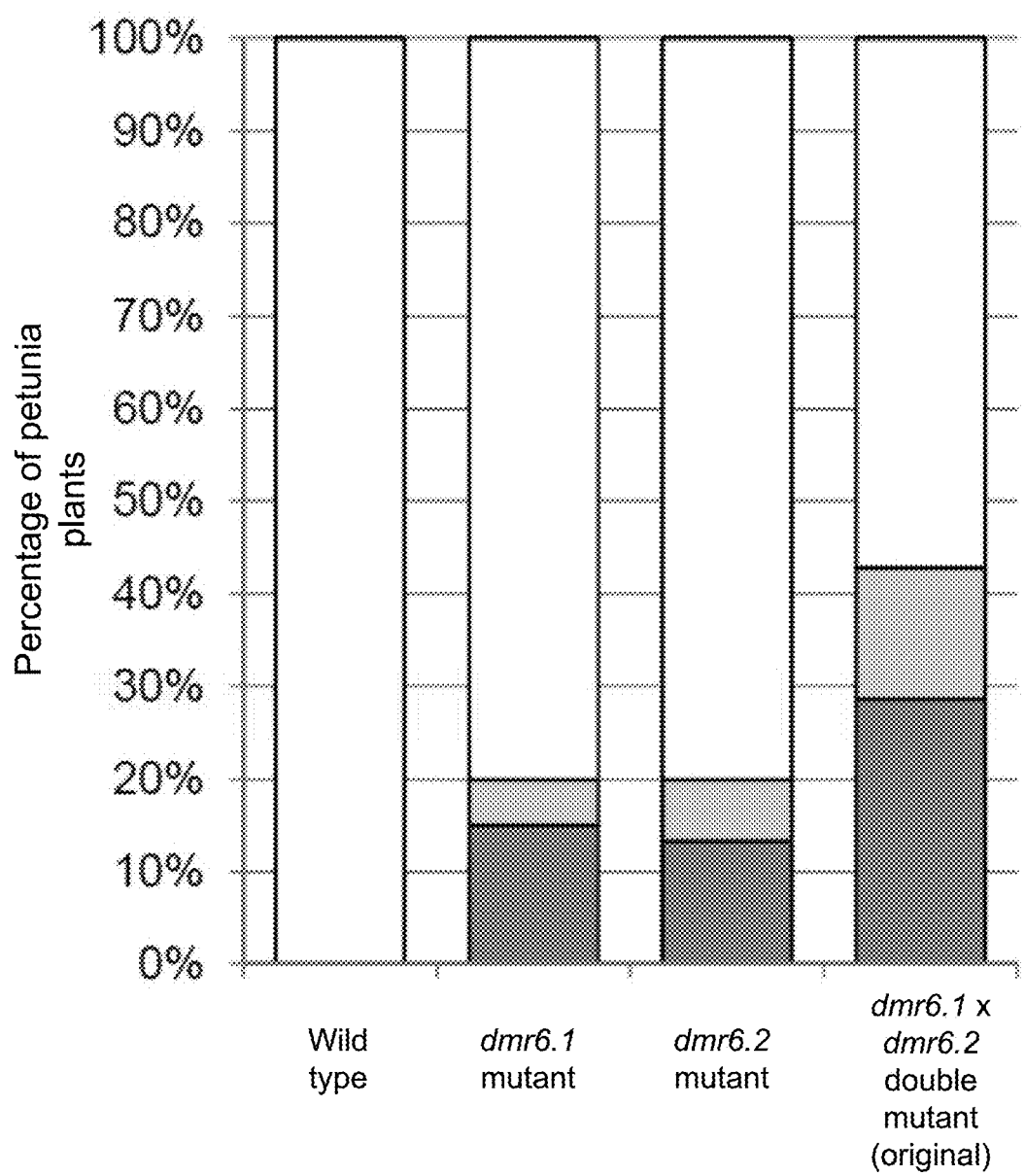
FIGS. 1A-1C show the results and representative images of plants of a soil drench assay of wild type *petunia* plants, dmr6.1 mutant *petunia* plants, dmr6.2 mutant *petunia* plants, and dmr6.1×dmr6.2 double mutant *petunia* plants (W138 background) with *Phytophthora nicotianae*.

The dmr6 mutant was first identified in a loss-of-susceptibility screen in the *Arabidopsis thaliana* Ler eds1-2 background. The DMR6 gene was then cloned and characterized as gene At5g24530, encoding an oxidoreductase. Oxidoreductases are enzymes that catalyze the transfer of electrons from one molecule, the oxidant, to another, the reductant. Disease resistance assays found that lack of a functional DMR6 protein in *A. thaliana* resulted in downy mildew resistance.

While *A. thaliana* has a single DMR6 gene, as do most other plant species, some plant species have multiple DMR6 genes. *Petunia* is one of these, and it has the genes DMR6.1 (genomic DNA=SEQ ID NO: 9; genomic DNA from start to stop=SEQ ID NO: 10) and DMR6.2 (genomic DNA=SEQ ID NO: 11; genomic DNA from start to stop=SEQ ID NO: 12). The coding sequence of DMR6.1 is SEQ ID NO: 3, and the coding sequence of DMR6.2 is SEQ ID NO: 7. The protein sequence of DMR6.1 is SEQ ID NO: 4 and the protein sequence of DMR6.2 is SEQ ID NO: 8. Disease resistance assays identified that lack of a functional DMR6.1 protein and a functional DMR6.2 protein resulted in *petunia* plants resistant to *Phytophthora* spp. and powdery mildew.

The present disclosure thus provides *petunia* plants resistant to fungal or oomycete pathogens, characterized in that the plant has mutant alleles that knock out the DMR6.1 protein and the DMR6.2 protein. These mutant alleles contain transposon footprints, and are designated as dmr6.1 (genomic DNA from start to stop=SEQ ID NO: 14; coding sequence=SEQ ID NO: 1) and dmr6.2 (genomic DNA from start to stop=SEQ ID NO: 16; coding sequence=SEQ ID NO: 5). The mutant alleles are predicted to encode truncated proteins dmr6.1 (SEQ ID NO: 2) and dmr6.2 (SEQ ID NO: 6).

*Phytophthora* and powdery mildew pathogens

Many species of *Phytophthora* are plant pathogens of considerable economic importance. *Phytophthora infestans* was the infective agent of the potato blight that caused the Great Irish Famine (1845-1849). It continues to be the most destructive pathogen of solanaceous crops, including tomato and potato. The soybean root and stem rot agent, *Phytophthora sojae*, has also caused longstanding problems for the agricultural industry. In general, plant diseases caused by the *Phytophthora* genus are difficult to control chemically, and thus the growth of resistant cultivars is the main management strategy.

Other important *Phytophthora* species include the following: *Phytophthora cactorum*, which causes rhododendron root rot affecting rhododendrons and azaleas and also causes bleeding canker in hardwood trees; and *Phytophthora capsici*, which infects Solanaceae (e.g. pepper, tomato), and Cucurbitaceae fruits, such as cucumbers and squash. The *Phytophthora* species that infect *Petunia* spp., are primarily *Phytophthora nicotianae* (previously known as *Phytoph-*

*thora parasitica*), *Phytophthora cactorum, Phytophthora cryptogea*, and *Phytophthora infestans*.

Solanaceae

The Solanaceae, or nightshades, are an economically important family of flowering plants. The family ranges from herbs to trees, and includes a number of important agricultural crops, medicinal plants, spices, and ornamentals. Many members of the family contain potent alkaloids, and some are highly toxic. The Solanaceae family belongs to the order Solanales, in the asterid group dicotyledons (Magnoliopsida). The Solanaceae family consists of approximately 98 genera and 2,700 species, which have a great diversity of habitats, morphology and ecology. The family has a worldwide distribution being present on all continents except *Antarctica*. The greatest diversity in species is found in South America and Central America.

Solanaceae includes a number of commonly collected or cultivated species.

Perhaps the most economically important genus of the family is *Solanum*, which contains the potato (*Solanum tuberosum*), the tomato (*Solanum lycopersicum*), and the eggplant (*Solanum melongena*). Another important genus is *Capsicum*, which includes both chili peppers and bell peppers. The genus *Physalis* includes groundcherries, as well as tomatillo (*Physalis philadelphica*), Cape gooseberry, and Chinese lantern. The genus *Lycium* contains boxthorns and wolfberry (*Lycium barbarum*). *Nicotiana* contains, among other species, the plant that produces tobacco. Some other important members of Solanaceae include a number of ornamental plants such as *Petunia, Browallia* and *Lycianthes*, the source of psychoactive alkaloids, *Datura, Mandragora* (mandrake), and *Atropa belladonna* (deadly nightshade). Certain species are universally known for their medicinal uses, their psychotropic effects or for being poisonous.

With the exception of tobacco (Nicotianoideae) and *petunia* (Petunioideae), most of the economically important genera are contained in the subfamily Solanoideae. Finally, but not less importantly, Solanaceae includes many model organisms which are important in the investigation of fundamental biological questions at a cellular, molecular and genetic level, such as tobacco and *petunia*.

Petunia Plants of the Present Disclosure

Accordingly, certain aspects of the present disclosure relate to a mutant *petunia* (e.g., *Petunia* spp., *Petunia*× *hybrida*, etc.) plant including a first nucleotide sequence (dmr6.1) including SEQ ID NO: 14 and a second nucleotide sequence (dmr6.2) including SEQ ID NO: 16. Some aspects of the present disclosure relate to a mutant *petunia* plant including a first nucleotide sequence (dmr6.1) including SEQ ID NO: 13 and a second nucleotide sequence (dmr6.2) including SEQ ID NO: 15. In some embodiments, the mutant *petunia* plant includes a first coding sequence (dmr6.1) including SEQ ID NO: 1 and a second coding sequence (dmr6.2) including SEQ ID NO: 5. In some embodiments, the first nucleotide sequence includes a transposon footprint corresponding to nucleotides 305-310 of SEQ ID NO: 1, and the second nucleotide sequence includes a transposon footprint corresponding to nucleotides 369-375 of SEQ ID NO: 5. The transposon footprints in dmr6.1 and dmr6.2 introduce premature stop codons into the coding sequences. Without wishing to be bound by theory, it is thought that these premature stop codons knock out the full-length wild type protein sequences and/or produce a truncated protein transcripts.

In some embodiments, the mutant *petunia* plant further includes a first polypeptide sequence (dmr6.1) including SEQ ID NO: 2 and a second polypeptide sequence (dmr6.2) including SEQ ID NO: 6. In some embodiments, the first polypeptide sequence includes a stop codon after residue 103 of SEQ ID NO: 2, and the second polypeptide sequence includes a stop codon after residue 124 of SEQ ID NO: 6. Both the polypeptide sequence of dmr6.1 and the polypeptide sequence of dmr6.2 are truncated sequences containing premature stop codons.

In some embodiments, the mutant *petunia* plant exhibits resistance selected from the group of resistance to *Phytophthora nicotianae* (previously known as *Phytophthora parasitica*), resistance to *Phytophthora infestans*, resistance to *Phytophthora cactorum*, resistance to *Phytophthora cryptogea*, or resistance to powdery mildew. In some embodiments, the mutant *petunia* plant exhibits resistance to *Phytophthora nicotianae* (*Phytophthora parasitica*). In some embodiments, the mutant *petunia* plant exhibits resistance to *Phytophthora infestans*. In some embodiments, the mutant *petunia* plant exhibits resistance to *Phytophthora cactorum*. In some embodiments, the mutant *petunia* plant exhibits resistance to *Phytophthora cryptogea*. In some embodiments, the mutant *petunia* plant exhibits resistance to *Phytophthora nicotianae* (previously known as *Phytophthora parasitica*), *Phytophthora infestans*, *Phytophthora cactorum*, and *Phytophthora cryptogea*. In some embodiments, the mutant *petunia* plant further exhibits resistance to powdery mildew. In some embodiments, any of the resistances of the above embodiments are the result of the plant including the first nucleotide sequence including SEQ ID NO: 14 and the second nucleotide sequence including SEQ ID NO: 16. In some embodiments, any of the resistances of the above embodiments are the result of the plant including the first nucleotide sequence including SEQ ID NO: 13 and the second nucleotide sequence including SEQ ID NO: 15. In some embodiments, any of the resistances of the above embodiments are the result of the plant including the first coding sequence including SEQ ID NO: 1 and the second coding sequence including SEQ ID NO: 5. In some embodiments, any of the resistances of the above embodiments are the result of the plant including the first polypeptide sequence including SEQ ID NO: 2 and the second polypeptide sequence including SEQ ID NO: 6.

In some embodiments, the present disclosure relates to a tissue or plant part of the *petunia* plant of any of the above embodiments, wherein the tissue or plant part includes the first nucleotide sequence including SEQ ID NO: 14 and the second nucleotide sequence including SEQ ID NO: 16. In some embodiments, the present disclosure relates to a tissue or plant part of the *petunia* plant of any of the above embodiments, wherein the tissue or plant part includes the first nucleotide sequence including SEQ ID NO: 13 and the second nucleotide sequence including SEQ ID NO: 15. In some embodiments, the tissue or plant part includes the first coding sequence including SEQ ID NO: 1 and the second coding sequence including SEQ ID NO: 5. *Petunia* plant tissues include differentiated and undifferentiated tissues of plants including those present in roots, shoots, leaves, inflorescences, anthers, pollen, ovaries, seeds, and tumors. *Petunia* plant parts include roots, root tips, stems, leaves, flowers, petals, sepals, anthers, pistils, ovules, pollen grains, and parts thereof. In some embodiments, the plant part includes a root, a stem, a leaf, a flower, a petal, an anther, a pistil, an ovule, or a pollen grain.

In some aspects, the present disclosure relates to a seed produced from the plant of any of the above embodiments. In some embodiments, the seed includes the first nucleotide sequence including SEQ ID NO: 14 and the second nucleotide sequence including SEQ ID NO: 16. In some embodiments, the seed includes the first nucleotide sequence including SEQ ID NO: 13 and the second nucleotide sequence including SEQ ID NO: 15. In some embodiments, the seed includes the first coding sequence including SEQ ID NO: 1 and the second coding sequence including SEQ ID NO: 5. In some embodiments, the seed further includes the first polypeptide sequence including SEQ ID NO: 2 and the second polypeptide sequence including SEQ ID NO: 6.

In some aspects, the present disclosure relates to a protoplast produced from the plant of any of the above embodiments. In some aspects, the present disclosure relates to a tissue culture produced from protoplasts or cells from the plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell. Tissue culture may include organ culture, tissue culture, or cell culture (e.g., single cells, protoplasts, embryos, callus, etc.). In some embodiments, the present disclosure relates to a *petunia* plant regenerated from the tissue culture, wherein the plant includes the first nucleotide sequence including SEQ ID NO: 14 and the second nucleotide sequence including SEQ ID NO: 16. In some embodiments, the *petunia* plant regenerated from the tissue culture includes the first nucleotide sequence including SEQ ID NO: 13 and the second nucleotide sequence including SEQ ID NO: 15. In some embodiments, the *petunia* plant regenerated from the tissue culture includes the first coding sequence including SEQ ID NO: 1 and the second coding sequence including SEQ ID NO: 5. In some embodiments, the plant further includes the first polypeptide sequence including SEQ ID NO: 2 and the second polypeptide sequence including SEQ ID NO: 6. In some embodiments, the plant exhibits resistance selected from the group of resistance to *Phytophthora nicotianae* (previously known as *Phytophthora parasitica*), resistance to *Phytophthora infestans*, resistance to *Phytophthora cactorum*, resistance to *Phytophthora cryptogea*, or resistance to powdery mildew. In some embodiments, the mutant *petunia* plant exhibits resistance to *Phytophthora nicotianae* (previously known as *Phytophthora parasitica*), *Phytophthora infestans*, *Phytophthora cactorum*, and *Phytophthora cryptogea*. In some embodiments, the mutant *petunia* plant further exhibits resistance to powdery mildew.

All 2OG oxygenases such as DMR6 (Wilmouth et al. (2002), Structure, 10:93-103) have conserved essential iron-binding residues. The transposon footprint insertions in the dmr6.1 mutant allele and the dmr6.2 mutant allele results, in both cases, in a premature stop codon (directly encoded in the 7 nt footprint). This leads to a truncated protein of 103 amino acids (dmr6.1) or 124 amino acids (dmr6.2). In the wild type (unaltered) DMR6.1 and DMR6.2 proteins, the essential oxygenase domain that includes the iron-binding residues (pfam 03171 oxoglutarate/iron-dependent oxygenase) begins at amino acid residues 185 (DMR6.1) and 187 (DMR6.2). This means that both the dmr6.1 mutant allele and the dmr6.2 mutant allele result in protein truncations that completely lose the essential and characteristic oxygenase domain, rendering the proteins non-functional.

*Petunia* plants of the present disclosure may further include plants in which the genes DMR6.1 (genomic DNA=SEQ ID NO: 9; genomic DNA from start to stop=SEQ ID NO: 10) and DMR6.2 (genomic DNA=SEQ ID NO: 11; genomic DNA from start to stop=SEQ ID NO: 12) are mutated such that premature stop codons are introduced into the coding sequences (DMR6.1 coding sequence=SEQ ID NO: 3; DMR6.2 coding sequence=SEQ ID NO: 7). In some embodiments, the introduction of a premature stop codon may be through a single nucleotide change, a multiple nucleotide change, a single nucleotide deletion, a multiple nucleotide deletion, the deletion of nucleotides such that a frameshift mutation is produced, or the insertion of nucleotides such that a frameshift mutation is produced. *Petunia* plants of the present disclosure may therefore further include frameshift mutations introduced into the DMR6.1 and DMR6.2 coding sequences, insertions introduced into the DMR6.1 and DMR6.2 coding sequences, deletions of a part or a whole of the DMR6.1 and DMR6.2 coding sequences, or alteration of the DMR6.1 and DMR6.2 coding sequences such that one or more encoded amino acids are altered. In some embodiments, the *petunia* plants of the present disclosure include knocked out full-length wild type protein sequences and/or truncated protein transcripts.

As used herein, the term "mutant *petunia* plant" refers to a *petunia* (*Petunia* spp.) plant including mutated alleles of DMR6.1 (genomic DNA=SEQ ID NO: 9; genomic DNA from start to stop=SEQ ID NO: 10; coding sequence=SEQ ID NO: 3) and DMR6.2 (genomic DNA=SEQ ID NO: 11; genomic DNA from start to stop=SEQ ID NO: 12; coding sequence=SEQ ID NO: 7), wherein the mutated alleles include premature stop codons. Preferably, the mutated alleles are dmr6.1 (genomic DNA=SEQ ID NO: 13; genomic DNA from start to stop=SEQ ID NO: 14; coding sequence=SEQ ID NO: 1) and dmr6.2 (genomic DNA=SEQ ID NO: 15; genomic DNA from start to stop=SEQ ID NO: 16; coding sequence=SEQ ID NO: 5). Mutant *petunia* plants of the present disclosure include *petunia* plants exhibiting resistance to *Phytophthora nicotianae* (previously known as *Phytophthora parasitica*), resistance to *Phytophthora infestans*, resistance to *Phytophthora cactorum*, resistance to *Phytophthora cryptogea*, or resistance to powdery mildew. In some embodiments, the mutant *petunia* plant exhibits resistance to *Phytophthora nicotianae* (previously known as *Phytophthora parasitica*), *Phytophthora infestans*, *Phytophthora cactorum*, and *Phytophthora cryptogea*. In some embodiments, the mutant *petunia* plant further exhibits resistance to powdery mildew.

In order to determine whether a plant is a plant of the present disclosure, and therefore whether said plant has the same alleles as plants of the present disclosure, the genotype of a plant can be examined. There are many laboratory-based techniques known in the art that are available for the analysis, comparison and characterization of plant genotype. Such techniques include, without limitation, High Resolution Melting (HRM), DNA- or RNA-sequencing, CAPS Markers, Single Nucleotide Polymorphisms (SNPs), Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs, which are also referred to as Microsatellites). By using these techniques, it is possible to assess the presence of the alleles involved in the resistance phenotype of the *petunia* plants of the present disclosure. The phenotypes of plants containing these alleles can further be compared to the phenotype of a known plant of the present disclosure using the assay methods described herein.

Methods for Obtaining *Petunia* Plants of the Present Disclosure

Further aspects of the present disclosure relate to methods for obtaining a mutant *petunia* (*Petunia* spp.) plant including: introducing a first nucleotide sequence including SEQ ID NO: 14 and a second nucleotide sequence including SEQ ID NO: 16. In some aspects, the present disclosure relates to methods for obtaining a mutant *petunia* (*Petunia* spp.) plant including: introducing a first nucleotide sequence including SEQ ID NO: 13 and a second nucleotide sequence including SEQ ID NO: 15. In some aspects, the present disclosure relates to methods for obtaining a mutant *petunia* (*Petunia* spp.) plant including: introducing a first coding sequence including SEQ ID NO: 1 and a second coding sequence including SEQ ID NO: 5. In some embodiments, the introduction is achieved through traditional breeding (e.g., using a *petunia* line including transposons, known to have active transposons, etc.) or a gene editing technique. In some embodiments, the gene editing technique is selected from the group of transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques.

Additional aspects of the present disclosure relate to methods for obtaining mutant *petunia* plants including premature stop codons introduced into the coding sequences of DMR6.1 (SEQ ID NO: 3) and DMR6.2 (SEQ ID NO: 7). The introduction of a premature stop codon may be through a single nucleotide change, a multiple nucleotide change, a single nucleotide deletion, a multiple nucleotide deletion, the deletion of nucleotides such that a frameshift mutation is produced, or the insertion of nucleotides such that a frameshift mutation is produced. In some embodiments, the introduction of a premature stop codon may be by any suitable methodology, including, without limitation, mutagenic treatment (e.g., EMS), radiation treatment, transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques. These premature stop codons may truncate or remove the essential oxygenase domain of the DMR6.1 protein and the DMR6.2 protein.

Further aspects of the present disclosure include loss-of-function mutations introduced into the coding sequences of DMR6.1 (SEQ ID NO: 3) and DMR6.2 (SEQ ID NO: 7). The introduction of a loss-of-function mutation may be through a single or multiple nucleotide change, a single or multiple nucleotide deletion, or a single or multiple nucleotide insertion such that an amino acid substitution occurs at the protein level. In some embodiments, the introduction of a loss-of-function mutation may be by any suitable methodology, including, without limitation, mutagenic treatment (e.g., EMS), radiation treatment, transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques. These loss-of-function mutations may disrupt or alter the essential oxygenase domain of the DMR6.1 protein and the DMR6.2 protein.

Some aspects of the present disclosure relate to a mutant *petunia* plant produced by any of the above methods. In some embodiments, the mutant *petunia* plant exhibits resistance selected from the group of resistance to *Phytophthora nicotianae* (previously known as *Phytophthora parasitica*), resistance to *Phytophthora infestans*, resistance to *Phytophthora cactorum*, resistance to *Phytophthora cryptogea*, or resistance to powdery mildew. In some embodiments, the mutant *petunia* plant exhibits resistance to *Phytophthora nicotianae*. In some embodiments, the mutant *petunia* plant exhibits resistance to *Phytophthora infestans*. In some embodiments, the mutant *petunia* plant exhibits resistance to *Phytophthora cactorum*. In some embodiments, the mutant *petunia* plant exhibits resistance to *Phytophthora cryptogea*. In some embodiments, the mutant *petunia* plant exhibits resistance to *Phytophthora nicotianae* (previously known as *Phytophthora parasitica*), *Phytophthora infestans*, *Phytophthora cactorum*, and *Phytophthora cryptogea*. In some embodiments, the mutant *petunia* plant further exhibits resistance to powdery mildew.

The present invention is illustrated in the following examples that are not intended to limit the invention in any way. In the examples, reference is made to the figures described above.

EXAMPLES

Example 1: Development of Dmr6.1×Dmr6.2 Double Mutant *Petunia* Plants and Resistance Testing with *Phytophthora nicotianae*

The following example describes the identification of dmr6.1 and dmr6.2 transposon insertion alleles in *petunia*, and the development of dmr6.1×dmr6.2 double mutant *petunia* plants. Further, experiments in which the resistance of dmr6.1 and dmr6.2 mutant plants to *Phytophthora nicotianae* was tested are described.

Materials and Methods

Plant Lines

*Petunia* transposon insertion lines were identified from a transposon insertion library. The transposon insertion system was described in Gerats et al., and included a dTph1 transposon in the *Petunia* spp. line W138 (Gerats at al. (1990). Plant Cell 2(11):1121-1128). The method used to identify transposon insertions in dmr6.1 and dmr6.2 was described in Vandenbussche et al. (Vandenbussche et al. (2008). The Plant Journal 54: 1105-1114). Two dTph1 transposon insertion alleles were identified in DMR6.1 (SEQ ID NO: 3), and three dTph1 transposon insertion alleles were identified in DMR6.2 (SEQ ID NO: 7).

The dTph1 transposons were known to jump out of their insertion locations again, often restoring the function of the gene ("revertant" gene). With reasonable frequency, however, the transposons would leave a footprint of 7-8 bases. In these cases, a mutation would be present that was stable (no more chance to get a revertant). Further, if this footprint was early enough in the gene, a 7-8 base deletion would lead to a frame-shift and loss of function. On the basis of this knowledge, the approach was taken of crossing the two dTph1 transposon insertion alleles in DMR6.1 to the three dTph1 transposon insertion alleles in DMR6.2 (several crosses) to generate homozygous double mutant offspring. Among these, plants that had lost the transposon were identified. These plants were then re-sequenced to make sure that they contained mutant alleles with transposon footprints and not revertant alleles.

This approach identified the transposon insertion alleles dmr6.1 (genomic DNA=SEQ ID NO: 13; genomic DNA from start to stop=SEQ ID NO: 14; coding sequence=SEQ ID NO: 1) and dmr6.2 (genomic DNA=SEQ ID NO: 15; genomic DNA from start to stop=SEQ ID NO: 16; coding sequence=SEQ ID NO: 5), which were selected for further testing. The first plants used in testing were the original double mutant plants from the single mutant cross (W138 background). The W138 background, while useful for transposon tagging, produced sickly plants that were difficult to work with in disease assays. The second plants used in testing were the result of introgression of the transposon insertion alleles dmr6.1 and dmr6.2 into different commercial *Petunia* spp. backgrounds (e.g., Ez Rider® white background). These second plants were the results of 1-2 backcrosses and 2 selfings (i.e., BC1S2 plants) to develop a series of homozygous mutant plants in different backgrounds. The transfer of the dmr6.1 and dmr6.2 alleles into these backgrounds resulted in plants that were easier to work with and had restored vigor.

*Phytophthora nicotianae* Assay

Wild type, dmr6.1 single mutant, dmr6.2 single mutant, and dmr6.1×dmr6.2 double mutant *petunia* plants were individually potted in standard potting soil, and grown at 25° C.

*Phytophthora nicotianae* spores were harvested from cultures grown on V8 agar plates by covering the cultures with water for 2 days. This was followed by an hour of incubation in the refrigerator, which allowed the sporangia to activate/release spores. Spore suspensions were adjusted to 10,000 spores/ml and plants were treated either by drenching the soil (~2 ml suspension/plant) or by spraying the whole plant. Plant lesions and collapse (disease symptoms) were monitored regularly.

Results

Figure 1B:
Figure 1C:

The results of the *P. nicotianae* soil drench assay testing the original dmr6.1×dmr6.2 double mutant plants in the W138 background are shown in FIGS. 1A-1C. FIG. 1A shows the percentages of living *petunia* plants at 45 dpi, and it can be seen that 100% of the wild type *petunia* plants died. For both the dmr6.1 mutant *petunia* plants and the dmr6.2 mutant *petunia* plants, 80% of the plants died and 20% of the plants survived. In contrast, 45% of the dmr6.1×dmr6.2 double mutant *petunia* plants survived. FIGS. 1B-1C show representative images of the dmr6.1×dmr6.2 double mutant and the wild type plants from this assay at 23 dpi. It can be seen that the wild type plants have almost all died, while the dmr6.1×dmr6.2 double mutant plants appear healthy and are flowering. Thus, the dmr6.1×dmr6.2 double mutant *petunia* plants showed enhanced resistance to *P. nicotianae* (minimal disease symptoms) as compared to the wild type plants (largely collapsed).

Figure 2A:
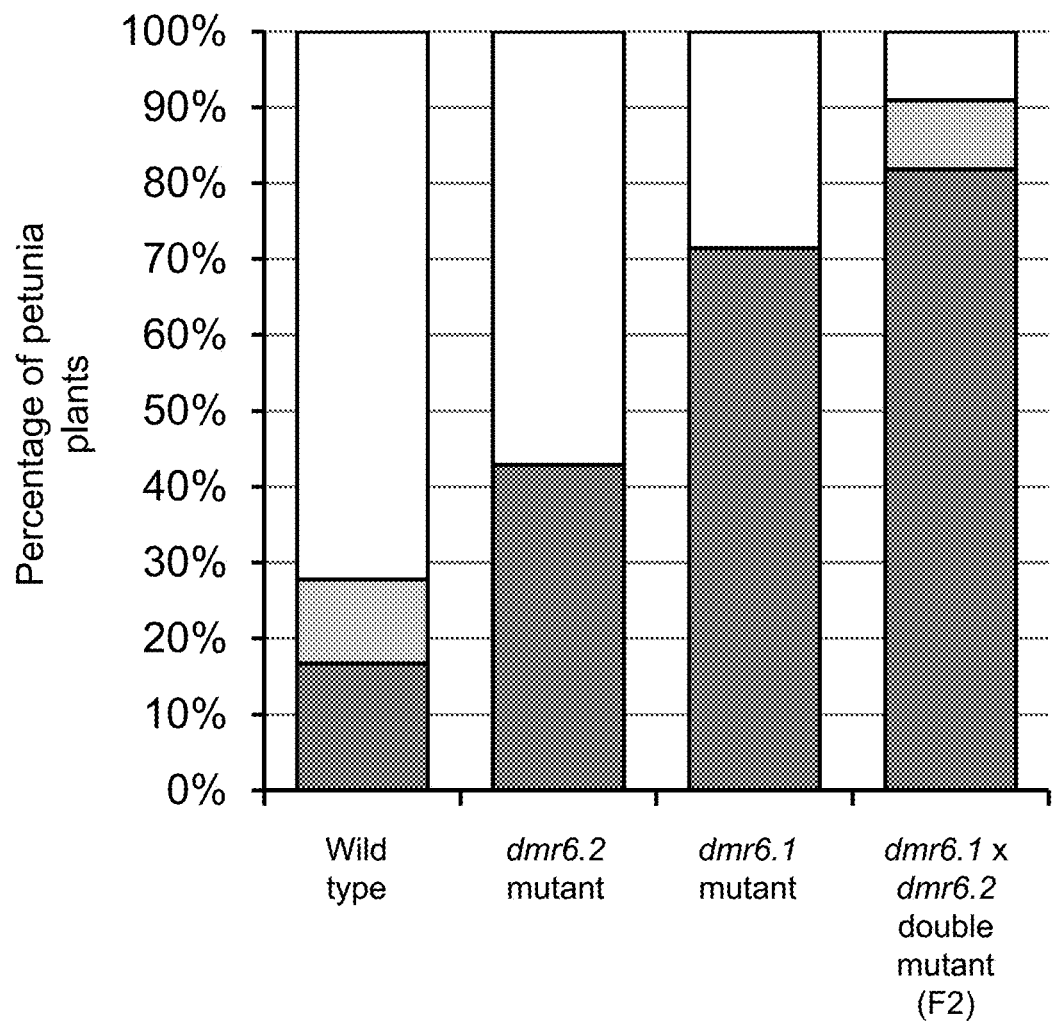
FIGS. 2A-2B show the results and the average disease index of a plant spray assay of wild type *petunia* plants, dmr6.1 mutant *petunia* plants, dmr6.2 mutant *petunia* plants, and dmr6.1×dmr6.2 double mutant *petunia* plants (BC1S2 plants) with *Phytophthora nicotianae*.
Figure 2B:
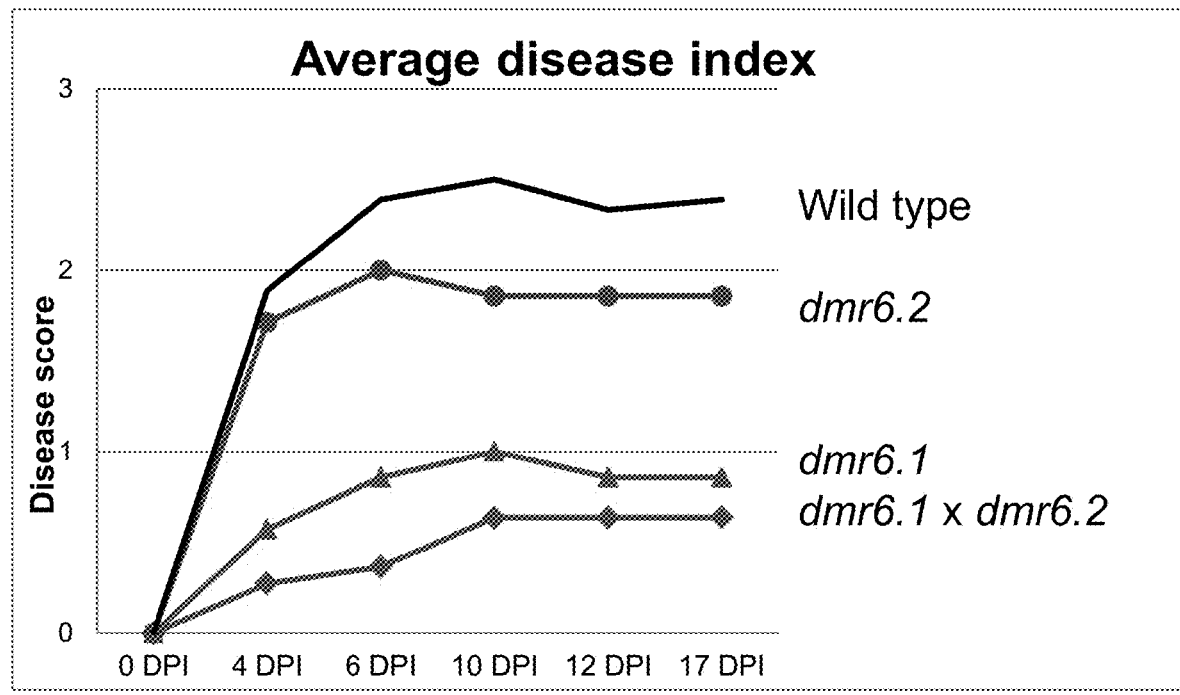

The results of the *P. nicotianae* plant spray assay testing of the BC1S2 dmr6.1×dmr6.2 double mutant plants are shown in FIGS. 2A-2B. FIG. 2A shows the percentages of living *petunia* plants at 10 dpi. About 70% of the wild type plants died (about 30% survived), about 60% of the dmr6.2 mutant plants died (about 40% survived), and about 30% of the dmr6.1 mutant plants died (about 60% survived). The dmr6.1×dmr6.2 double mutant *petunia* plants outperformed all the others tested: only about 10% of the plants died, and about 90% of the plants survived. The average disease index over the course of the experiment is shown in FIG. 2B (0=no symptoms; 1=lesions on leaves; 2=rotten stems and petioles; 3=collapsed). It can be seen that the wild type *petunia* plants had a disease index over 2 at about 5 dpi. In contrast, the dmr6.1×dmr6.2 double mutant *petunia* plants had a disease index less than 1 throughout the course of the experiment. The results for the dmr6.2 single mutant were more similar to wild type, while results for the dmr6.1 single mutant were more similar to the dmr6.1×dmr6.2 double mutant. The average disease index indicated that the dmr6.1×dmr6.2 double mutant maintains enhanced resistance with minimal disease symptoms throughout the experiment.

Moreover, these results clearly demonstrated that the dmr6.1 and dmr6.2 mutant alleles could be transferred to another genetic background and maintain the phenotypic effect of enhanced resistance.

Example 2: Resistance Testing of Dmr6.1×Dmr6.2 Double Mutant *Petunia* Plants with *Phytophthora infestans*

The following example describes experiments in which the resistance of dmr6.1×dmr6.2 mutant plants to *Phytophthora infestans* was tested.

Materials and Methods

Plant Lines

The *petunia* dmr6.1×dmr6.2 double mutant BC1S2 plants described in Example 1 were used.

*Phytophthora infestans* Assay

Wild type and dmr6.1×dmr6.2 double mutant *petunia* plants were individually potted in standard potting soil, and grown at 18° C. *Phytophthora infestans* was cultured on rye agarose plates and spores were harvested by washing them off the plate with water. Spore suspensions were adjusted to 100,000 spores/ml and sprayed over the plants. Plants were kept at 100% relative humidity (RH) at 18° C. and monitored regularly for disease symptoms.

Results

Figure 3:
FIG. 3 shows a representative image of a wild type *petunia* plant (on left) and a dmr6.1×dmr6.2 double mutant BC1S2 *petunia* plant (on right) inoculated with *Phytophthora infestans* at 10 days post inoculation (dpi).

FIG. 3 shows a representative image of a wild type *petunia* plant and a dmr6.1×dmr6.2 double mutant *petunia* plant infected with *Phytophthora infestans* at 10 dpi. The dmr6.1×dmr6.2 double mutant *petunia* plant showed improved resistance to *P. infestans* as compared to the wild type plant. The dmr6.1×dmr6.2 double mutant *petunia* plant showed minimal disease symptoms compared to the wild type *petunia* plant, which had visible lesions.

Example 3: Resistance Testing of Dmr6.1×Dmr6.2 Double Mutant *Petunia* Plants with Powdery Mildew The following example describes experiments in which the resistance of dmr6.1×dmr6.2 mutant plants to powdery mildew was tested.

Materials and Methods

Plant Lines

The *petunia* dmr6.1×dmr6.2 double mutant BC1S2 plants described in Example 1 were used.

Powdery Mildew Assay

Wild type and dmr6.1×dmr6.2 double mutant *petunia* plants were individually potted in standard potting soil, and grown at 23° C. Powdery mildew (PM) infection was done by shaking PM-infected leaves or plants above the plants to be tested, resulting in a visible "dusting" with spores from a naturally infected plant. Plants were maintained at normal conditions and PM infection was monitored visually.

Results

Figure 4A:
FIGS. 4A-4B show representative images of wild type *petunia* plants and dmr6.1×dmr6.2 double mutant BC1S2 *petunia* plants inoculated with powdery mildew (harvested from a naturally infected plant) at 14 days post inoculation (dpi).
Figure 4B:
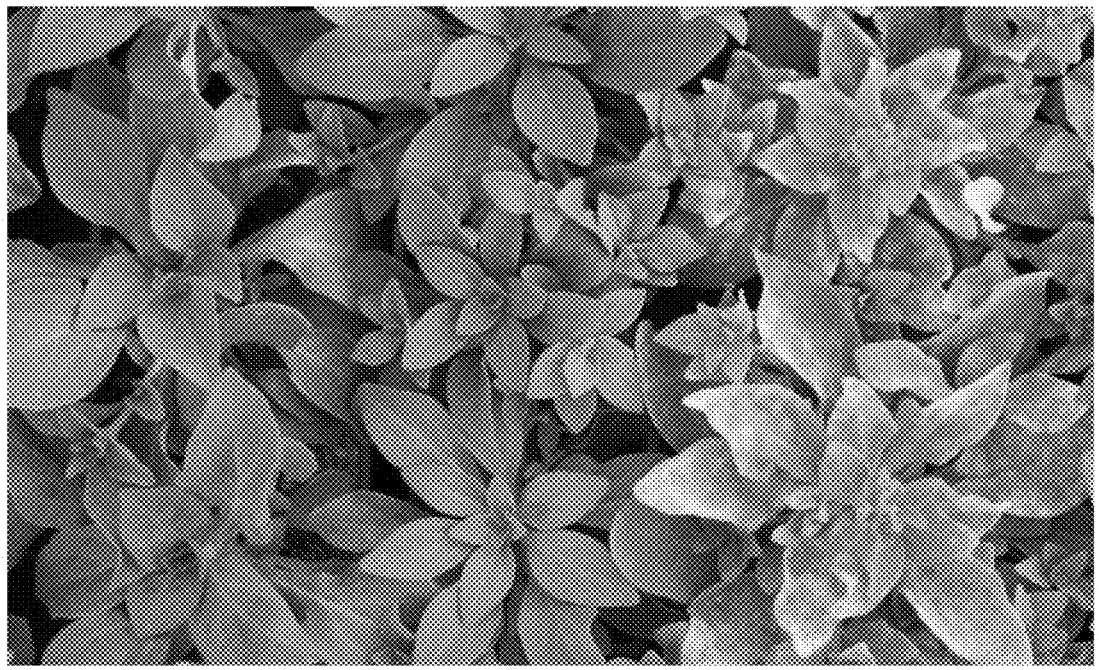

FIGS. 4A-4B show representative images of wild type *petunia* plants and a dmr6.1×dmr6.2 double mutant *petunia* plant infected with powdery mildew at 14 dpi. The dmr6.1×dmr6.2 double mutant *petunia* plant showed improved resistance to powdery mildew as compared to the wild type plant. The dmr6.1×dmr6.2 double mutant *petunia* plants showed minimal disease symptoms compared to the wild type *petunia* plants, which had visible powdery mildew (white powdery appearance of leaves).

What is claimed is:

1. A mutant *petunia* (*Petunia* spp.) plant comprising, homozygous DMR6.1 alleles each comprising a nucleotide sequence comprising SEQ ID NO: 14 and homozygous DMR6.2 alleles each comprising a nucleotide sequence comprising SEQ ID NO: 16.

2. The mutant *petunia* plant of claim 1, wherein the plant comprises a polypeptide having a sequence comprising SEQ ID NO: 2 and a polypeptide having a sequence comprising SEQ ID NO: 6.

3. The mutant *petunia* plant of claim 1, wherein the plant exhibits resistance selected from the group consisting of resistance to *Phytophthora nicotianae*, resistance to *Phytophthora infestans*, and resistance to powdery mildew.

4. The mutant *petunia* plant of claim 3, wherein the plant exhibits resistance to *Phytophthora nicotianae*.

5. The mutant *petunia* plant of claim 3, wherein the plant exhibits resistance to *Phytophthora infestans*.

6. The mutant *petunia* plant of claim 3, wherein the plant exhibits resistance to powdery mildew.

7. A tissue or plant part of the mutant *petunia* plant of claim 1, wherein the tissue or plant part comprises homozygous DMR6.1 alleles each comprising a nucleotide sequence comprising SEQ ID NO: 14 and homozygous DMR6.2 alleles each comprising a nucleotide sequence comprising SEQ ID NO: 16.

8. The plant part of claim 7, wherein the plant part comprises a root, a stem, a leaf, a flower, a petal, an anther, a pistil, an ovule, or a pollen grain.

9. A seed produced from the mutant *petunia* plant of claim 1, the seed comprising homozygous DMR6.1 alleles each comprising a nucleotide sequence comprising SEQ ID NO: 14 and homozygous DMR6.2 alleles each comprising a nucleotide sequence comprising SEQ ID NO: 16.

10. A tissue culture produced from protoplasts or cells from the mutant *petunia* plant of claim 1, wherein the protoplasts or cells are produced from a plant part selected from the group consisting of leaf, anther, pistil, stem, petiole, root, root primordia, root tip, fruit, seed, flower, cotyledon, hypocotyl, embryo, and meristematic cell, and wherein the protoplasts or cells comprise homozygous DMR6.1 alleles each comprising a nucleotide sequence comprising SEQ ID NO: 14 and homozygous DMR6.2 alleles each comprising a nucleotide sequence comprising SEQ ID NO: 16.

11. A *petunia* plant regenerated from the tissue culture of claim 10, the plant comprising homozygous DMR6.1 alleles each comprising a nucleotide sequence comprising SEQ ID NO: 14 and homozygous DMR6.2 alleles each comprising a nucleotide sequence comprising SEQ ID NO: 16.

12. The *petunia* plant of claim 11, wherein the plant comprises a polypeptide having a sequence comprising SEQ ID NO: 2 and a polypeptide having a sequence comprising SEQ ID NO: 6.

13. The *petunia* plant of claim 11, wherein the plant exhibits resistance selected from the group consisting of resistance to *Phytophthora nicotianae*, resistance to *Phytophthora infestans*, and resistance to powdery mildew.

14. A mutant *petunia* (*Petunia* spp.) plant resistant to one or more fungal or oomycete pathogens, wherein the mutant *petunia* plant comprises mutant alleles of DMR6.1 such that it does not express a DMR6.1 protein comprising a DMR6.1 oxygenase domain and mutant alleles of DMR6.2 such that it does not express a DMR6.2 protein comprising a DMR6.2 oxygenase domain.

15. The mutant *petunia* plant of claim 14, wherein the mutant alleles of DMR6.1 encode a truncated DMR6.1 protein, wherein the truncated DMR6.1 protein does not comprise a DMR6.1 oxygenase domain, and the mutant alleles of DMR6.2 encode a truncated DMR6.2 protein, wherein the truncated DMR6.2 protein does not comprise a DMR6.2 oxygenase domain.

16. The mutant *petunia* plant of claim 15, wherein the mutant alleles of DMR6.1 encode a truncated DMR6.1 protein having the sequence of SEQ ID NO: 2 and wherein the mutant alleles of DRM6.2 encode a truncated DMR6.2 protein having the sequence of SEQ ID NO: 6.

17. The mutant *petunia* plant of claim 15, wherein the coding sequence of each of the mutant alleles of DMR6.1 comprises the nucleic acid sequence of SEQ ID NO: 1 and wherein the coding sequence of each of the mutant alleles of DMR6.2 comprises the nucleic acid sequence of SEQ ID NO: 5.

18. A tissue or plant part of the mutant *petunia* plant of claim 14, wherein the tissue or plant part comprises mutant alleles of DMR6.1 such that the tissue or plant part does not express a DMR6.1 protein comprising a DMR6.1 oxygenase domain and mutant alleles of DMR6.2 such that the tissue or plant part does not express a DMR6.2 protein comprising a DMR6.2 oxygenase domain.

19. The plant part of claim 18, wherein the plant part comprises a root, a stem, a leaf, a flower, a petal, an anther, a pistil, an ovule, or a pollen grain.

20. A seed produced from the mutant *petunia* plant of claim 14, wherein the seed comprises mutant alleles of DMR6.1 such that it does not express a DMR6.1 protein comprising a DMR6.1 oxygenase domain and mutant alleles of DMR6.2 such that it does not express a DMR6.2 protein comprising a DMR6.2 oxygenase domain.

* * * * *

SEQUENCE LISTING

<160> NUMBER OF SEQ ID NOS: 16

<210> SEQ ID NO 1
<211> LENGTH: 1021
<212> TYPE: DNA
<213> ORGANISM: Artificial Sequence
<220> FEATURE:
<223> OTHER INFORMATION: Synthetic Construct

<400> SEQUENCE: 1

```
atggaaacaa aagttctttc aagtggaatc cgtcattcta ccctccctca aaattatgtc    60
cgacccaaat ccgataggcc acgtctttca gaagtggcca attgtgaaaa cgttccagtt   120
attgacttgg gttgtgctga cagaactctc ataattcatc aaattagcga agcctgtcgt   180
ctttatggtt ttttccaggt aataaaccat ggtgtaccaa aaaaaatagt tgaggaaatg   240
ctagagatag ctggggagtt ttttaggcta ccagttgaag agaagcttaa gttgtattca   300
gatgtgagat gacccttcaa agaccatgag attatcaact agtttttaatg taaagaagga   360
gacggtgcac aattggagag attatctcag acttcattgt tatcctctgg agaaatatgc   420
tcctgaatgg ccttcaaatc cttcatcttt cagggaaatc gtgagcagat attgcacgga   480
agttcgacaa cttggattca gattgcaaga agccatagca gaaagcttag cttagagaa    540
agagtgtata aaggatgtgt taggtgaaca aggtcaacat atggctataa acttttatcc   600
tccatgccca gaaccagaac tcacttacgg gctgccagcc cataccgatc caaatgctct   660
tacaattctt cttcaagact tgcaagtagc tggtctccaa gttcttaaag atggcaaatg   720
gttggctgtc aaacctcagc ccgatgcctt tgttgttaat ctcggtgatc aactgcaggc   780
agtgagtaac ggaaggtaca aaagcgtatg gcatcgagct gttgtaaata cagaaaatgc   840
caggatgtct gtggcttcgt tcttatgtcc ctgtgatagt gcaaaaatca gtgctccaaa   900
actcctcact gatgatggat ctccaataat ttatcgggac ttcacgtatg cagagtatta   960
caagaagttc tggagcagga atttggacca agaacattgt ttggaacttt tcaagaatta  1020
a                                                                   1021
```

<210> SEQ ID NO 2
<211> LENGTH: 103
<212> TYPE: PRT
<213> ORGANISM: Artificial Sequence
<220> FEATURE:
<223> OTHER INFORMATION: Synthetic Construct

<400> SEQUENCE: 2

```
Met Glu Thr Lys Val Leu Ser Ser Gly Ile Arg His Ser Thr Leu Pro
1               5                  10                  15

Gln Asn Tyr Val Arg Pro Lys Ser Asp Arg Pro Arg Leu Ser Glu Val
            20                  25                  30

Ala Asn Cys Glu Asn Val Pro Val Ile Asp Leu Gly Cys Ala Asp Arg
        35                  40                  45

Thr Leu Ile Ile His Gln Ile Ser Glu Ala Cys Arg Leu Tyr Gly Phe
    50                  55                  60

Phe Gln Val Ile Asn His Gly Val Pro Lys Lys Ile Val Glu Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Val Arg
            100
```

<210> SEQ ID NO 3
<211> LENGTH: 1014
<212> TYPE: DNA
<213> ORGANISM: Petunia x hybrida

<400> SEQUENCE: 3

```
atggaaacaa aagttctttc aagtggaatc cgtcattcta ccctccctca aaattatgtc      60
cgacccaaat ccgataggcc acgtctttca gaagtggcca attgtgaaaa cgttccagtt     120
attgacttgg gttgtgctga cagaactctc ataattcatc aaattagcga agcctgtcgt     180
ctttatggtt ttttccaggt aataaaccat ggtgtaccaa aaaaaatagt tgaggaaatg     240
ctagagatag ctggggagtt ttttaggcta ccagttgaag agaagcttaa gttgtattca     300
gatgacccct caaagaccat gagattatca actagttta atgtaaagaa ggagacggtg     360
cacaattgga gagattatct cagacttcat tgttatcctc tggagaaata tgctcctgaa     420
tggccttcaa atccttcatc tttcaggaa atcgtgagca gatattgcac ggaagttcga     480
caacttggat tcagattgca agaagccata gcagaaagct taggcttaga gaaagagtgt     540
ataaaggatg tgttaggtga acaaggtcaa catatggcta taaacttta tcctccatgc     600
ccagaaccag aactcactta cgggctgcca gcccataccg atccaaatgc tcttacaatt     660
cttcttcaag acttgcaagt agctggtctc caagttctta agatggcaa atggttggct     720
gtcaaacctc agcccgatgc ctttgttgtt aatctcggtg atcaactgca ggcagtgagt     780
aacggaaggt acaaaagcgt atggcatcga gctgttgtaa atacagaaaa tgccaggatg     840
tctgtggctt cgttcttatg tccctgtgat agtgcaaaaa tcagtgctcc aaaactcctc     900
actgatgatg gatctccaat aatttatcgg gacttcacgt atgcagagta ttacaagaag     960
ttctggagca ggaatttgga ccaagaacat tgtttggaac ttttcaagaa ttaa          1014
```

<210> SEQ ID NO 4
<211> LENGTH: 337
<212> TYPE: PRT
<213> ORGANISM: Petunia x hybrida

<400> SEQUENCE: 4

```
Met Glu Thr Lys Val Leu Ser Ser Gly Ile Arg His Ser Thr Leu Pro
1               5                   10                  15

Gln Asn Tyr Val Arg Pro Lys Ser Asp Arg Pro Arg Leu Ser Glu Val
            20                  25                  30

Ala Asn Cys Glu Asn Val Pro Val Ile Asp Leu Gly Cys Ala Asp Arg
        35                  40                  45

Thr Leu Ile Ile His Gln Ile Ser Glu Ala Cys Arg Leu Tyr Gly Phe
    50                  55                  60

Phe Gln Val Ile Asn His Gly Val Pro Lys Lys Ile Val Glu Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Ala Pro Glu Trp Pro Ser Asn
    130                 135                 140

Pro Ser Ser Phe Arg Glu Ile Val Ser Arg Tyr Cys Thr Glu Val Arg
145                 150                 155                 160
```

Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gly Gln His Met
            180                 185                 190

Ala Ile Asn Phe Tyr Pro Pro Cys Pro Glu Pro Glu Leu Thr Tyr Gly
            195                 200                 205

Leu Pro Ala His Thr Asp Pro Asn Ala Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Val Asn Leu Gly Asp Gln Leu
                245                 250                 255

Gln Ala Val Ser Asn Gly Arg Tyr Lys Ser Val Trp His Arg Ala Val
            260                 265                 270

Val Asn Thr Glu Asn Ala Arg Met Ser Val Ala Ser Phe Leu Cys Pro
        275                 280                 285

Cys Asp Ser Ala Lys Ile Ser Ala Pro Lys Leu Leu Thr Asp Asp Gly
    290                 295                 300

Ser Pro Ile Ile Tyr Arg Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 5
<211> LENGTH: 1030
<212> TYPE: DNA
<213> ORGANISM: Artificial Sequence
<220> FEATURE:
<223> OTHER INFORMATION: Synthetic Construct

<400> SEQUENCE: 5

```
atggaatcta atgttatttc agcggaacc  aaatacacaa acctccctaa aagttatgtt      60
cgcccagaat cccaacgacc tcggttatct gaagtagacg attgccaaga taatattcca     120
gttattgatt tgtgttgcag agacaataac gttatcattc aacaaattga agaagcttgt     180
cgtctttatg cttttttca  ggtaataaac catggtgtac caagaaaact aatagaggaa     240
atgctagggg tagctcatga gttttttcaag ctaccagtgg aagagaagat gaagttgtac     300
tcagatgatc catcaaagac catgagatta tcaacaagtt ttaatgtgaa gaaggaaact     360
gttcataaat cataattgga gagactatct tagattgcac tgctatcctt tggagaaata     420
tgcccctgaa tggccttcta ctccctcttc tttcagggaa atcgttagca gatattgcat     480
agaagttcga caacttggat atagattaca agaagcaata tcagagagct taggcctaga     540
gaaagattgt ataaaaaata tattgggtga acaaggtcaa catatggctg ttaattatta     600
ccctccatgt ccagaaccag aactaactta tggtttgcca gcccatactg atcctaatgc     660
ccttactata cttcttcaag acttgcaagt agcaggtctt caagttctca aggatggtaa     720
atggttatct gtgaaacctc gggccaatgc ctttgtcatc aatcttggtg atcaattgca     780
ggcgctgagt aatggaaaat atagaagtgt atggcacaga gctatagtaa attcagacaa     840
accaaggctg tcagtggctt ctttcttgtg tcctagtgat tgtgcgataa tcagtgctcc     900
aaaaacctta actgaagatg ggtctccaac cattatcgg  gatttcacgt atccagaata     960
ttacaagaaa ttttggagca gaaatttaga tcaagaacac tgtatggaac ttttcaagaa    1020
```
aggaagctag 1030

<210> SEQ ID NO 6
<211> LENGTH: 124
<212> TYPE: PRT
<213> ORGANISM: Artificial Sequence
<220> FEATURE:
<223> OTHER INFORMATION: Synthetic Construct

<400> SEQUENCE: 6

```
Met Glu Ser Asn Val Ile Ser Ser Gly Thr Lys Tyr Thr Asn Leu Pro
1               5                   10                  15

Lys Ser Tyr Val Arg Pro Glu Ser Gln Arg Pro Arg Leu Ser Glu Val
            20                  25                  30

Asp Asp Cys Gln Asp Asn Ile Pro Val Ile Asp Leu Cys Cys Arg Asp
        35                  40                  45

Asn Asn Val Ile Ile Gln Gln Ile Glu Glu Ala Cys Arg Leu Tyr Gly
    50                  55                  60

Phe Phe Gln Val Ile Asn His Gly Val Pro Lys Lys Leu Ile Glu Glu
65                  70                  75                  80

Met Leu Gly Val Ala His Glu Phe Phe Lys Leu Pro Val Glu Glu Lys
                85                  90                  95

Met Lys Leu Tyr Ser Asp Asp Pro Ser Lys Thr Met Arg Leu Ser Thr
            100                 105                 110

Ser Phe Asn Val Lys Lys Glu Thr Val His Lys Ser
        115                 120
```

<210> SEQ ID NO 7
<211> LENGTH: 1023
<212> TYPE: DNA
<213> ORGANISM: Petunia x hybrida

<400> SEQUENCE: 7
atggaatcta atgttatttc cagcggaacc aaatacacaa acctccctaa aagttatgtt 60
cgcccagaat cccaacgacc tcggttatct gaagtagacg attgccaaga taatattcca 120
gttattgatt tgtgttgcag agacaataac gttatcattc aacaaattga agaagcttgt 180
cgtctttatg gcttttttca ggtaataaac catggtgtac caaagaaact aatagaggaa 240
atgctagggg tagctcatga gttttttcaag ctaccagtgg aagagaagat gaagttgtac 300
tcagatgatc catcaaagac catgagatta tcaacaagtt ttaatgtgaa gaaggaaact 360
gttcataatt ggagagacta tcttagattg cactgctatc ctttggagaa atatgcccct 420
gaatggcctt ctactccctc ttctttcagg gaaatcgtta gcagatattg catagaagtt 480
cgacaacttg gatatagatt acaagaagca atatcagaga gcttaggcct agagaaagat 540
tgtataaaaa atatattggg tgaacaaggt caacatatgg ctgttaatta ttaccctcca 600
tgtccagaac cagaactaac ttatggtttg ccagcccata ctgatcctaa tgcccttact 660
atacttcttc aagacttgca agtagcaggt cttcaagttc tcaaggatgg taaatggtta 720
tctgtgaaac ctcgggccaa tgcctttgtc atcaatcttg gtgatcaatt gcaggcgctg 780
agtaatggaa aatatagaag tgtatggcac agagctctag taaattcaga caaaccaagg 840
ctgtcagtgg cttctttctt gtgtcctagt gattgtgcga taatcagtgc tccaaaaacc 900
ttaactgaag atgggtctcc aaccatttat cgggatttca cgtatccaga atattacaag 960
aaatttttgga gcagaaattt agatcaagaa cactgtatgg aacttttcaa gaaaggaagc 1020
tag                                                              1023

<210> SEQ ID NO 8
<211> LENGTH: 340
<212> TYPE: PRT
<213> ORGANISM: Petunia x hybrida

<400> SEQUENCE: 8

Met Glu Ser Asn Val Ile Ser Ser Gly Thr Lys Tyr Thr Asn Leu Pro
1               5                   10                  15

Lys Ser Tyr Val Arg Pro Glu Ser Gln Arg Pro Arg Leu Ser Glu Val
            20                  25                  30

Asp Asp Cys Gln Asp Asn Ile Pro Val Ile Asp Leu Cys Cys Arg Asp
        35                  40                  45

Asn Asn Val Ile Ile Gln Gln Ile Glu Glu Ala Cys Arg Leu Tyr Gly
    50                  55                  60

Phe Phe Gln Val Ile Asn His Gly Val Pro Lys Lys Leu Ile Glu Glu
65                  70                  75                  80

Met Leu Gly Val Ala His Glu Phe Phe Lys Leu Pro Val Glu Glu Lys
                85                  90                  95

Met Lys Leu Tyr Ser Asp Asp Pro Ser Lys Thr Met Arg Leu Ser Thr
            100                 105                 110

Ser Phe Asn Val Lys Lys Glu Thr Val His Asn Trp Arg Asp Tyr Leu
        115                 120                 125

Arg Leu His Cys Tyr Pro Leu Glu Lys Tyr Ala Pro Glu Trp Pro Ser
    130                 135                 140

Thr Pro Ser Ser Phe Arg Glu Ile Val Ser Arg Tyr Cys Ile Glu Val
145                 150                 155                 160

Arg Gln Leu Gly Tyr Arg Leu Gln Glu Ala Ile Ser Glu Ser Leu Gly
                165                 170                 175

Leu Glu Lys Asp Cys Ile Lys Asn Ile Leu Gly Glu Gln Gly Gln His
            180                 185                 190

Met Ala Val Asn Tyr Tyr Pro Pro Cys Pro Glu Pro Glu Leu Thr Tyr
        195                 200                 205

Gly Leu Pro Ala His Thr Asp Pro Asn Ala Leu Thr Ile Leu Leu Gln
    210                 215                 220

Asp Leu Gln Val Ala Gly Leu Gln Val Leu Lys Asp Gly Lys Trp Leu
225                 230                 235                 240

Ser Val Lys Pro Arg Ala Asn Ala Phe Val Ile Asn Leu Gly Asp Gln
                245                 250                 255

Leu Gln Ala Leu Ser Asn Gly Lys Tyr Arg Ser Val Trp His Arg Ala
            260                 265                 270

Ile Val Asn Ser Asp Lys Pro Arg Leu Ser Val Ala Ser Phe Leu Cys
        275                 280                 285

Pro Ser Asp Cys Ala Ile Ile Ser Ala Pro Lys Thr Leu Thr Glu Asp
    290                 295                 300

Gly Ser Pro Thr Ile Tyr Arg Asp Phe Thr Tyr Pro Glu Tyr Tyr Lys
305                 310                 315                 320

Lys Phe Trp Ser Arg Asn Leu Asp Gln Glu His Cys Met Glu Leu Phe
                325                 330                 335

Lys Lys Gly Ser
            340

<210> SEQ ID NO 9
<211> LENGTH: 10000

```
<212> TYPE: DNA
<213> ORGANISM: Petunia x hybrida
<220> FEATURE:
<221> NAME/KEY: misc_feature
<222> LOCATION: 25, 26, 27, 28, 29, 91, 92, 93, 94, 95, 96, 97, 98, 99,
      100, 101, 102, 103, 104, 105, 106, 107, 108, 109, 110, 111, 112,
      113, 114, 115, 116, 117, 118, 119, 120, 121, 122, 123, 124, 125,
      126, 127, 128, 8456
<223> OTHER INFORMATION: n = A,T,C or G

<400> SEQUENCE: 9
```

| | | | | |
|---|---|---|---|---|
| ggttcttgat attcatgcat catannnnnc tttaacttgt ttaatttaac tgctttgcag | 60 |
| gtgtttggtt cttgatattc atgcatcata nnnnnnnnnn nnnnnnnnnn nnnnnnnnnn | 120 |
| nnnnnnnntt acgcgcggga tcttctagct caatatcaga agggaagctt aactaatcgt | 180 |
| tcaaggtaga ggatcatgca aagcaatata gagatagctg tgcaacttgt tacaattatt | 240 |
| taacaacgct acaatattaa ccatggctat ggcaataaat actactcgta taaaaagcct | 300 |
| tccataacac acacagtaaa aaaacaaaa aagaataaac aaaataaaa cacaaataca | 360 |
| atacgtacat acatacagac atacataa tatatagact cacagacacg attaaatatc | 420 |
| agtaaattgc ttcagctcat tttcaaatta aaagaaaaa aaaacgact ttctttgcct | 480 |
| ttggaaatat gattgaatct gcttgagcta atcaattttt taatgtggtc aatattacat | 540 |
| aattatttca aaattaattt ttagcattta tcatccttgc actgacctgt acggagatat | 600 |
| aattaagaat gagtaaaagt atataattag ttgtagaaag ggaggaacat tattcgttta | 660 |
| caaatctatt aatgataaac aaggattata tgaaaaatg catgaaactc atagaaaaat | 720 |
| ggtcttagat acaataaatg attctctctc tatcacaaag ttaatttgca tatataaaat | 780 |
| gtaataaata aattaagatt tttgtaaact cgtgactaaa ataagctata agtatttgtg | 840 |
| tagttgtaaa taaataaaat gagaatattt aagtaaaatt attttcaaat tgaaaaatat | 900 |
| gagaattctt ttttttttaat gaatgaaata ccttcaaata tagggtcaag tcatactcac | 960 |
| acttgtgaaa ctccgttata ggtgacgaat taaacatgac gtaagtaaat taatacggcg | 1020 |
| agccttgcag cttgcctata tataacttgg aaatttccta gaaactgaaa atctgagttg | 1080 |
| tgggcaattc ttttcgttcc caaatcacaa ataattttt tctttatatg cgagtcaaaa | 1140 |
| tcagattcaa tggaaacaaa agttctttca agtggaatcc gtcattctac cctccctcaa | 1200 |
| aattatgtcc gacccaaatc cgataggcca cgtctttcag aagtggccaa ttgtgaaaac | 1260 |
| gttccagtta ttgacttggg ttgtgctgac agaactctca taattcatca aattagcgaa | 1320 |
| gcctgtcgtc tttatggttt tttccaggta aacataatta atcatttctg tttcttcatt | 1380 |
| atcaaaatct acatttatgg taaccaattt aactttatgt ttaggtaata aaccatggtg | 1440 |
| taccaaaaaa aatagttgag gaaatgctag agatagctgg ggagttttt aggctaccag | 1500 |
| ttgaagagaa gcttaagttg tattcagatg acccttcaaa gaccatgaga ttatcaacta | 1560 |
| gttttaatgt aaagaaggag acggtgcaca attggagaga ttatctcaga cttcattgtt | 1620 |
| atcctctgga gaaatatgct cctgaatggc cttcaaatcc ttcatctttc aggtaaacac | 1680 |
| cattaagact cttcactaag ctttcttctt gggttaatct ggtttcatgt gtgttggtgg | 1740 |
| atacatttgc tatccgagtc atatatttta tccttatcta cgtcaaccat gtttgtttgt | 1800 |
| tgtactataa tcactaagca ctgcatggat gcaaaactaa aataacatta ttgtgcgttg | 1860 |
| cacgtaataa tatgttgcaa taatatgttg tcatctatat aaattgttta tacatattaa | 1920 |
| ataaataaaa tattctaaaa gaagtatatt ctttatgagc atatatcagg tacgtatcag | 1980 |
| gtgtttgttt gtttgtccta catgatatat aatcaggtgt ttgtttgttt gtcctacata | 2040 |

```
atatataata aatactagac gaaatatatc gcatcaatat taagaaatat ttagagttat    2100
aaattatctg ggcacgtgtc aggtgtttgt ctgtttgtcc tacatgatat gtaataaata    2160
ccagaagaaa tattcctaaa atatccatca atattaagaa atatttagag ttataaatta    2220
tctgggcacg tgtgagacac gtgtcaagtg tttatctgtt tgtactgaag gtatatgata    2280
aatactcaaa aaaattaaaa tattgactcg ctattaagaa aatatttaat aatttatatt    2340
actagtacat tagtagtaat tgttttgatt atggagtata ctaatacaat actatttcac    2400
tctagcgagg tcgttttgaa aatagagggt caatcattct aaaaattgat atgattaaaa    2460
taaacctttt tattgatctg acaaaaacca tttagtctct ctaagactct aaccttctaa    2520
gtagtaatgt aaaaagtcct tgagagtttt aagagaatgc atgttccatg tgaatgtgcc    2580
aaccatttct catttcttca ccttttcctt tttatatttt ccatatctta tgaatattta    2640
agaagtatca agttggagtt gtccaatagg attacttagt aatcgaaaat gaaatggagc    2700
aagattatgg agtcttgacc ttgacactgg ttttgttgat gctccttatg atagaattgc    2760
aagaactaat ggccacggaa gctattgtac accatttta gaagttggat tctctatata    2820
gagcttgagt tcctaattca gtattatttt acatgttctt cttatatagg taagtttaaa    2880
aaatacaatg taggtacact gagtaaaatta tagaaaaatc gagataggta agttgagcta    2940
caattggaga aaggaaagta ctcctccgtc ccaaattagt tgacgtttta gcaataatta    3000
tttaactcaa attatacccct taataattaa aataattctc aacaaaattt aatagacaaa    3060
cttaaatagg ggtaacatag taaaatatac accttattaa tgatttctta atggacgtga    3120
aaaagctgaa ggcgacaatt aatttgggac ggagggagta gaaatttgag tggacaaggg    3180
gtagacgtta gagataacag aaaagaagca tgtgaaaaaa agcatgtgag gccacatttg    3240
actattctag atttaatcct attgattgaa attaaaactt ccatcaactt atcttgcagc    3300
catgtgctgc caattaacta gcaccttctt cggtgccaaa acccaaattt tcttttcctt    3360
caacttacaa aatggctatt tgttacgtca tggctaacga atttgatgac atcatgtttg    3420
ttgccatatt agcccagtaa tcgacacgta atcaatgatt gtgtcaccat caagatgaag    3480
tcatttggta gatagttggt ggcataagca gacaatggaa gtaaatgttg gatagccaaa    3540
cttgtgattt ttgtgtcggc tagtatccat aggggatgcg atgacttcca gagtctcctt    3600
taaatgaata ctttaggaaa gaacttacta aaagattctc aaaaaagtac tttgattttt    3660
agttaatata gtacatctat ttgctacaga aaaagtactt ttagaaaatg aaataaagag    3720
tactctagcg aggatctaaa aaatgtccgc tttaccatta caggcccgt gattttcgtg     3780 cttcttgtgc cttgtataat ttcttcttcg cctgggaaag taaagaaaag taggcttaag    3840
taaagaggaa tggagaaaac aaaaaagtta ctgtactaat taaaggata attaaaagag    3900 aaaatttatt cgaataaaga aaaacaaaa taatccataa aaaattaata ggggaatccc    3960
ttcgagaaaa ttaataacgg tttagctgag acctaacatc caatatattt tgcacaagtc    4020
tttttgtaat gaaatttttct tgagaatcgt cctaaaccta gctagtagaa gttaacgtag    4080
gcataatcta ctcgctgcca acacactgct ccaattaagc cgaacaacgg caaacagcat    4140
aacaataaac aaagataagt gggttattgg ttttagtata gtctagagta ccccgcatag    4200
gctgtatcat ccatttcgaa tttgtgtcca gaaaaatact tccgctattt catttatat     4260 ggcaagattt aaaatgcgag agtcaaactt gttagcttta aatattttta agaaaatgta    4320
atgaaatatt taataaaaat gtggtcgaaa ctgaaataaa gactccatag actcctaagc    4380
```

```
tagcgtttgg acatagattt gggtagaaag tttgtgaggg aaaaaaaaaa actcccaaat    4440
tctggtttca accggaatgt gggattttga agtttggag aaattctata acaaataag     4500 ttttaaaat  aatactcccc aaattttatg tccaaacggg aggtaaataa taatatggca   4560
cataaaatgg agtagtccgc caatggtaag ggattaagat ctggtcatga attattttc    4620 cataccaatt tgtttatacg tttattgggt agatgactta atcatattct taagaaatca   4680
atagtagtac ttaatgaagg tgggtgagca atcaagatct ctgaagcata taagtgaga    4740 ataagcagct aaaacgcgtt ttaaaggact taggtaccaa atgaaaaaga cctggaacat   4800
aaaatcaatg gcctaacgta agccaaggaa taatggggtt tatggttcaa tcatggacca   4860
tttgattaag ttttatataca tgagaatgaa tggcgtatag tagaatccga cgtatcatat  4920
ctacttgttt attcatttct tgtgttgtag gggttcttaa ttttactaag tacatcgtga   4980
aggtcaccat caaaactgat ccgagctagt ctttacatta attaagagca gtaaattgaa   5040
atttgtcaat gctaattgcg gctgttctca cgcgttgtta aatgatgtta gcgtgctaat   5100
tgcatctctg taaacttcca aattgttgtg ctaccgacgt gttatctttt tcaaattttc   5160
tttagataga gatggacttt ggattacagt agaggaaaaa gtagagagga gactatccca   5220
ttcaacctat tgaccatttg tcctattgca tcacctgttt gtattggttg ctttggtcat   5280
ggtttgttat tgctaaaatt tgtgttagag cgaattctg gtagattgt catatttagc     5340 cccagaaaag aatattatgc aaaaagtgaa ttccttgtga tcagtaatga catttttta    5400 ctacagtcct gacaatttgc tagaaggtgc cttaaattt ggcggagaag ctacaaccaa    5460
cttttttttt cagaggatta aagttaaaaa gaggcactaa aatagtctat ccatgcaaat   5520
atccctcttt tttcgggga agtgcaccaa aggccacatt tgccagtggt ctttagtttg    5580
aagccacttt ttttttattg attttacata aagatcact ttttgaaata tcaattcttt    5640
tggcttgaac ttcacacgag ttcagcccac aaggattaaa gttcaacttc agcccaccac   5700
aaggattgaa gttgaacttc tatacctaaa agtttagtcc ttactgattg aagttgagac   5760
ttcataattt aggcatgaag ttcaatctac atggtttgaa tttcagctca caaagattgg   5820
agttccaaaa aaatgacctc tcatataaga caaataaaaa agtgacttaa aactaaatac   5880
cagtaaaaaa aagtggcatg tgggtaaaaa tttcactttt ttattgacag tataagcatc   5940
gggatatttg tagtaataga atatttcagt gctactattt aactttttat cccatttcaa   6000
gaatttaact tttagactct ggcactagaa tttggagcca cttcctaatg gattaccagg   6060
attcacttca taaggtcct  aacaagtcct tatggataga cataaagagc taaataatta   6120
accctttctt  cttaggagcc taaaaaaatt aaacacagct gccagcgcca gtctcccaca   6180
acagtggttt aacaaaatag catttgcatg atttttataaa tgaatttcgg tcgaaaatag  6240
ccctacgaat tatataatga cgcccgcatc taactttctt tctcgtaagt acaggcagca   6300
cttgcctcct attgcttagg caacatttgc actgaaatct ctttcaagat ccttatagat   6360
aacttgaatt gttgcctagg caatacttgt ggttgaaatc ttgcctaggc aacaattgac   6420
gttgaaaaat gcttatctag gtaacacttg tcttttgacc tcttttcacg ttctttcata   6480
taacttgaaa tattgcctat ggacgaagcg gagataattc tgctaaaatc atcttaaacg   6540
tggacaaact cttaaaatta gtcaattttg aggatacgag tgaaactttt taaaatatgt   6600
gttgtaatac gcactattag ccgctttgtg ttatgcattt aagtgcaggg aaagtgcagg   6660
aatagctttt ttttttttt  tgcccgcatt atagtttata agctatttt  aaaaaattat    6720 ttagtttta  gtcacttttt aaatttcaag ccttgggtct gatctttaaa tcttcagagt    6780
```

```
tgaagttcaa cttcagacct tcaggtctta acttaagata ttttatgcct aatttcaaac    6840
ttcaagtttg aagttagata tggaaggttt gaagtttgat atagtgacta aaaccacat    6900 cttcaccaaa atcttgtact ctattacata ttggggaggg gaaagaaaaa gaaaaatgat    6960
agaagagctg atgagaatcg cactcactct accagctggt tagagtcctc taggtaattt    7020
tgaggaaatt caagttggct ttgaaatgtg taacctggca acattaaaat aacatagcag    7080
tttgtacctt atattatata tactcattgt acaaggaatg tttgagcaat taatatagtt    7140
aattgaggtc taacatgcta tttttgatat tataagtttt agacattgtc agtataactt    7200
ttataagtta ttgtctacac tagtaaggaa taataactgt agtcagattt tcaattcatg    7260
cttgtagtag aggttcttaa aaacttgata gcccaacaat tgttcatgtc taaattgcta    7320
atgagttgat ttatttgtct ccctgttagc ctgtttcccc tcgtagcatg cttagccacc    7380
agtaacagct ttatgcatgc ttcatttctg caattaacaa taagttcctc catgcttatt    7440
aacaagtttc tgcatttaac agttttcttg cacataata tcttttaatt gaaataaaa    7500 ataatcttat ttgtcaatgt tctggttgac agggaaatcg tgagcagata ttgcacggaa    7560
gttcgacaac ttggattcag attgcaagaa gccatagcag aaagcttagg cttagagaaa    7620
gagtgtataa aggatgtgtt aggtgaacaa ggtcaacata tggctataaa cttttatcct    7680
ccatgcccag aaccagaact cacttacggg ctgccagccc ataccgatcc aaatgctctt    7740
acaattcttc ttcaagactt gcaagtagct ggtctccaag ttcttaaaga tggcaaatgg    7800
ttggctgtca aacctcagcc cgatgccttt gttgttaatc tcggtgatca actgcaggta    7860
aaacagaatt aacgctataa ttaaattagt tacttatatg caactgaatg catacattaa    7920
atatttaact tgtatacagt ttgaagaaat attacagtat catagtagta ttttaacacg    7980
tagtagtagg ttattgcctt tcatggcgga tgaaaccttt gctcaacggg ttgaactgaa    8040
cctaaaattt gtaaaattgc gaaattctat tataatctca acaaatgtta gattttgaaa    8100
ccataatttc agtgtgcgat cagttataaa agttaaactc atactctaaa ctaatgctcg    8160
ttggtcacgg tcattctgca ggcagtgagt aacggaaggt acaaaagcgt atggcatcga    8220
gctgttgtaa atacagaaaa tgccaggatg tctgtggctt cgttcttatg tccctgtgat    8280
agtgcaaaaa tcagtgctcc aaaactcctc actgatgatg gatctccaat aatttatcgg    8340
gacttcacgt atgcagagta ttacaagaag ttctggagca ggaatttgga ccaagaacat    8400
tgtttggaac ttttcaagaa ttaaagctag tatttaaaaa aaaaaaaaaa aaaccntatg    8460
gggtgagaat tagattagaa aataaaaaca gttatatctt cattgcttag ctgatttacc    8520
caattacaat acactggcct gtttggcaag ttgctaataa gcagtagcaa ttggctagaa    8580
ctggactaca agatctattt ggaagaggaa ttacaagggt ccagtatcca gatttgtttg    8640
tgtaggaata atatatactt attggttatt tctttccctg attttacttc cttctatgga    8700 agttacgtg tatcctatga attattttac ttctgtactt gtagtatata tgatttaccg    8760
cgcaaaagaa taattaatct aagtttgttg atatcctgaa gtatactgga acaaaaatac    8820
atctacttat tgggcactgg aagttggacc aagtccaaga tctacacttg aacgatgggt    8880
tacgcccaaa tcactatgta agcaaagact tccagtattt gatcaagtaa acagagattt    8940
taaagctaga aaaattagcg aatgactttt tctgcgaatc atccttggaa agaattagct    9000
ctaatgaata tatggacaat tagtcgataa tgtgctgaag taaagaagga acagctgaac    9060
aaagccacct aatatccagg acttctacat taaacacatt ccttaatcta aataacttca    9120
```

-continued

```
gcctttcatc tcctgtgacc taatatcttt aaattaatca tcaaatcttt agttaatccc    9180
aaaactataa tctcattttc taggtatccc actttattcc accaaccaaa catgcgtaag    9240
ttcctttctt ttgtcaaagc atgtgacctt taccaacttc tcctaggaac ttttgtaaag    9300
tgatcggaat ttggagcgaa acatagttgc ggaccaaaag tattttcctc aaagtgattg    9360
tgtgaacact gataatcata attatgattt aggtgtccat cagcttcata gttggcccaa    9420
cttagaattt tttagcacca aactgtataa ttgcaaacac tcgtactgaa tacatttggc    9480
tacttccaat tggccattta gtttccaaat tattttttaag ctgagcccta caactccttt    9540
cgaatttaac tttttctttt ttggtaggac atgatcagat catccaagac catttgcttt    9600
catatggctg ttacttgatg tgatcatgtt tacttaagtt tagtttaatt ttgtatgacc    9660
acacacttgt cttaacaatc aaattttaca acatcctact agtacatgta aactatgtct    9720
gagtcttaag agtatgattg gtcgaaagta aatgattagt acatgtgtgt tacagaaata    9780
catatactat aataaaattc aaagccagct aaaagaagct tcaatttaaa gacattgctt    9840
ttctgggagc aattatttca tcttcctcat atcttttgaa catcaatctc ttcaaggtaa    9900
aagctaattt tcttttattt cgcagtgaca tgtaatacat aacgctcaag ccactctgaa    9960
aaaagcaggt cacaattgca aaaggagcag tatatatatt                           10000
```

<210> SEQ ID NO 10
<211> LENGTH: 7275
<212> TYPE: DNA
<213> ORGANISM: Petunia x hybrida

<400> SEQUENCE: 10

```
atggaaacaa aagttctttc aagtggaatc cgtcattcta ccctccctca aaattatgtc      60
cgacccaaat ccgataggcc acgtctttca gaagtggcca attgtgaaaa cgttccagtt     120
attgacttgg ttgtgctga cagaactctc ataattcatc aaattagcga agcctgtcgt     180
ctttatggtt ttttccaggt aaacataatt aatcatttct gtttcttcat tatcaaaatc     240
tacatttatg gtaaccaatt taactttatg tttaggtaat aaaccatggt gtaccaaaaa     300
aaatagttga ggaaatgcta gagatagctg gggagttttt taggctacca gttgaagaga     360
agcttaagtt gtattcagat gacccttcaa agaccatgag attatcaact agttttaatg     420
taaagaagga gacggtgcac aattggagag attatctcag acttcattgt tatcctctgg     480
agaaatatgc tcctgaatgg ccttcaaatc cttcatcttt caggtaaaca ccattaagac     540
tcttcactaa gctttcttct tgggttaatc tggtttcatg tgtgttggtg atacatttg      600
ctatccgagt catatatttt atccttatct acgtcaacca tgtttgtttg ttgtactata     660
atcactaagc actgcatgga tgcaaaacta aaataacatt attgtgcgtt gcacgtaata     720
atatgttgca ataatatgtt gtcatctata taaattgttt atacatatta aataaataaa     780
atattctaaa agaagtatat tctttatgag catatatcag gtacgtatca ggtgtttgtt     840
tgtttgtcct acatgatata taatcaggtg tttgtttgtt tgtcctacat aatatataat     900
aaatactaga cgaaatatat cgcatcaata ttaagaaata tttagagtta taaattatct     960
gggcacgtgt caggtgtttg tctgtttgtc ctacatgata tgtaataaat accagaagaa    1020
atattcctaa aatatccatc aatattaaga aatatttaga gttataaatt atctgggcac    1080
gtgtgagaca cgtgtcaagt gtttatctgt ttgtactgaa ggtatatgat aaatactcaa    1140
aaaaattaaa atattgactc gctattaaga aaatatttaa taattatat tactagtaca    1200
ttagtagtaa ttgttttgat tatggagtat actaatacaa tactatttca ctctagcgag    1260
```

```
gtcgttttga aaatagaggg tcaatcattc taaaaattga tatgattaaa ataaacctttt    1320 ttattgatct gacaaaaacc atttagtctc tctaagactc taaccttcta agtagtaatg    1380
taaaaagtcc ttgagagttt aagagaatg catgttccat gtgaatgtgc caaccatttc    1440
tcatttcttc accttttcct ttttatattt tccatatctt atgaatattt aagaagtatc    1500
aagttggagt tgtccaatag gattacttag taatcgaaaa tgaaatggag caagattatg    1560
gagtcttgac cttgacactg gttttgttga tgctccttat gatagaattg caagaactaa    1620
tggccacgga agctattgta caccattttt agaagttgga ttctctatat agagcttgag    1680
ttcctaattc agtattattt tacatgttct tcttatatag gtaagtttaa aaaatacaat    1740
gtaggtacac tgagtaaatt atagaaaaat cgagataggt aagttgagct acaattggag    1800
aaaggaaagt actcctccgt cccaaattag ttgacgtttt agcaataatt atttaactca    1860
aattataccc ttaataatta aaataattct caacaaaatt taatagacaa acttaaatag    1920
gggtaacata gtaaaatata caccttatta atgatttctt aatggacgtg aaaaagctga    1980
aggcgacaat taatttggga cggagggagt agaaatttga gtggacaagg ggtagacgtt    2040
agagataaca gaaagaagc atgtgaaaaa aagcatgtga ggccacattt gactattcta    2100
gatttaatcc tattgattga aattaaaact tccatcaact tatcttgcag ccatgtgctg    2160
ccaattaact agcaccttct tcggtgccaa aacccaaatt ttcttttttct tcaacttaca    2220 aaatggctat ttgttacgtc atggctaacg aatttgatga catcatgttt gttgccatat    2280
tagcccagta atcgacacgt aatcaatgat tgtgtcacca tcaagatgaa gtcatttggt    2340
agatagttgg tggcataagc agacaatgga agtaaatgtt ggatagccaa acttgtgatt    2400
tttgtgtcgg ctagtatcca taggggatgc gatgacttcc agagtctcct ttaaatgaat    2460
actttaggaa agaacttact aaaagattct caaaaaagta ctttgatttt tagttaatat    2520
agtacatcta tttgctacag aaaaagtact tttagaaaat gaaataaaga gtactctagc    2580
gaggatctaa aaaatgtccg ctttaccatt acaggccccg tgattttcgt gcttcttgtg    2640
ccttgtataa tttcttcttc gcctgggaaa gtaaagaaaa gtaggcttaa gtaaagagga    2700
atggagaaaa caaaaaagtt actgtactaa ttaaaaggat aattaaaaga gaaaatttat    2760
tcgaataaag aaaaaacaaa ataatccata aaaaattaat aggggaatcc cttcgagaaa    2820
attaataacg gtttagctga gacctaacat ccaatatatt ttgcacaagt cttttgtaa    2880 tgaaattttc ttgagaatcg tcctaaacct agctagtaga agttaacgta ggcataatct    2940
actcgctgcc aacacactgc tccaattaag ccgaacaacg gcaaacagca taacaataaa    3000
caaagataag tgggttattg gttttagtat agtctagagt accccgcata ggctgtatca    3060
tccatttcga atttgtgtcc agaaaaatac ttccgctatt tcattttata tggcaagatt    3120
taaaatgcga gagtcaaact tgttagcttt aaaatatttt aagaaaatgt aatgaaatat    3180
ttaataaaaa tgtggtcgaa actgaaataa agactccata gactcctaag ctagcgtttg    3240
gacatagatt tgggtagaaa gtttgtgagg gaaaaaaaaa aactcccaaa ttctggtttc    3300
aaccggaatg tgggattttg aagttttgga gaaattctat aaacaaataa gttttttaaaa    3360 taatactccc caaattttat gtccaaacgg gaggtaaata ataatatggc acataaaatg    3420
gagtagtccg ccaatggtaa gggattaaga tctggtcatg aattattttt ccataccaat    3480
ttgtttatac gttattggg tagatgactt aatcatattc ttaagaaatc aatagtagta    3540
cttaatgaag gtgggtgagc aatcaagatc tctgaagcat aataagtgag aataagcagc    3600
```

```
taaaacgcgt tttaaaggac ttaggtacca aatgaaaaag acctggaaca taaaatcaat   3660
ggcctaacgt aagccaagga ataatggggt ttatggttca atcatggacc atttgattaa   3720
gttttttatac atgagaatga atggcgtata gtagaatccg acgtatcata tctacttgtt  3780
tattcatttc ttgtgttgta ggggttctta attttactaa gtacatcgtg aaggtcacca   3840
tcaaaactga tccgagctag tctttacatt aattaagagc agtaaattga aatttgtcaa   3900
tgctaattgc ggctgttctc acgcgttgtt aaatgatgtt agcgtgctaa ttgcatctct   3960
gtaaacttcc aaattgttgt gctaccgacg tgttatcttt ttcaaatttt ctttagatag   4020
agatggactt tggattacag tagaggaaaa agtagagagg agactatccc attcaaccta   4080
ttgaccattt gtcctattgc atcacctgtt tgtattggtt gctttggtca tggtttgtta   4140
ttgctaaaat ttgtgttaga gcgaatttct gggtagattg tcatatttag ccccagaaaa   4200
gaatattatg caaaaagtga attccttgtg atcagtaatg acatttttttt actacagtcc   4260
tgacaatttg ctagaaggtg ccttaaattt tggcggagaa gctacaacca acttttttttt 4320
tcagaggatt aaagttaaaa agaggcacta aaatagtcta tccatgcaaa tatccctctt   4380
ttttcggggg aagtgcacca aaggccacat tgccagtgg tctttagttt gaagccactt     4440
tttttttatt gattttacat aaaagatcac tttttgaaat atcaattctt ttggcttgaa   4500
cttcacacga gttcagccca caaggattaa agttcaactt cagcccacca caaggattga   4560
agttgaactt ctatacctaa aagtttagtc cttactgatt gaagttgaga cttcataatt   4620
taggcatgaa gttcaatcta catggtttga atttcagctc acaaagattg gagttccaaa   4680
aaaatgacct ctcatataag acaaataaaa aagtgactta aaactaaata ccagtaaaaa   4740
aaagtggcat gtgggtaaaa atttcactttt tttattgaca gtataagcat cgggatattt   4800
gtagtaatag aatatttcag tgctactatt taacttttta tcccatttca agaatttaac   4860
ttttagactc tggcactaga atttggagcc acttcctaat ggattaccag gattcacttc   4920
ataaggtcc taacaagtcc ttatggatag acataaagag ctaaataatt aacccttctt    4980
tcttaggagc ctaaaaaaat taaacacagc tgccagcgcc agtctcccac aacagtggtt   5040
taacaaaata gcatttgcat gatttttataa atgaatttcg gtcgaaaata gcccctacgaa 5100
ttatataatg acgcccgcat ctaactttct ttctcgtaag tacaggcagc acttgcctcc   5160
tattgcttag gcaacatttg cactgaaatc tctttcaaga tccttataga taacttgaat   5220
tgttgcctag gcaatacttg tggttgaaat cttgcctagg caacaattga cgttgaaaaa   5280
tgcttatcta ggtaacactt gtcttttgac ctctttttcac gttctttcat ataacttgaa  5340
atattgccta tggacgaagc ggagataatt ttgctaaaat catcttaaac gtggacaaac   5400
tcttaaaatt agtcaatttt gaggatacga gtgaaacttt ttaaaatatg tgttgtaata   5460
cgcactatta gccgctttgt gttatgcatt taagtgcagg gaaagtgcag gaatagcttt   5520
tttttttttt ttgcccgcat tatagtttat aagctatttt taaaaaatta tttagttttt   5580
agtcactttt taaatttcaa gccttgggtc tgatctttaa atcttcagag ttgaagttca   5640
acttcagacc ttcaggtctt aacttaagat attttatgcc taatttcaaa cttcaagttt   5700
gaagttagat atggaaggtt tgaagtttga tatagtgact aaaaaccaca tcttcaccaa   5760
aatcttgtac tctattacat attggggagg ggaaagaaaa agaaaaatga tagaagagct   5820
gatgagaatc gcactcactc taccagctgg ttagagtcct ctaggtaatt ttgaggaaat   5880
tcaagttggc tttgaaatgt gtaacctggc aacattaaaa taacatagca gtttgtacct   5940
tatattatat atactcattg tacaaggaat gtttgagcaa ttaatatagt taattgaggt   6000
```

-continued

```
ctaacatgct attttgata ttataagttt tagacattgt cagtataact tttataagtt      6060
attgtctaca ctagtaagga ataataactg tagtcagatt ttcaattcat gcttgtagta      6120
gaggttctta aaaacttgat agcccaacaa ttgttcatgt ctaaattgct aatgagttga      6180
tttatttgtc tccctgttag cctgtttccc ctcgtagcat gcttagccac cagtaacagc      6240
tttatgcatg cttcatttct gcaattaaca ataagttcct ccatgcttat taacaagttt      6300
ctgcatttaa cagtttcttt ggcacataat atcttttaat tgaaaataaa aataatctta      6360
tttgtcaatg ttctggttga cagggaaatc gtgagcagat attgcacgga agttcgacaa      6420
cttggattca gattgcaaga agccatagca gaaagcttag gcttagagaa agagtgtata      6480
aaggatgtgt taggtgaaca aggtcaacat atggctataa acttttatcc tccatgccca      6540
gaaccagaac tcacttacgg gctgccagcc cataccgatc caaatgctct tacaattctt      6600
cttcaagact tgcaagtagc tggtctccaa gttcttaaag atggcaaatg gttggctgtc      6660
aaacctcagc ccgatgcctt tgttgttaat ctcggtgatc aactgcaggt aaaacagaat      6720
taacgctata attaaattag ttacttatat gcaactgaat gcatacatta aatatttaac      6780
ttgtatacag tttgaagaaa tattacagta tcatagtagt attttaacac gtagtagtag      6840
gttattgcct ttcatggcgg atgaaacctt tgctcaacgg gttgaactga acctaaaatt      6900
tgtaaaattg cgaaattcta ttataatctc aacaaatgtt agattttgaa accataattt      6960
cagtgtgcga tcagttataa aagttaaact catactctaa actaatgctc gttggtcacg      7020
gtcattctgc aggcagtgag taacggaagg tacaaaagcg tatggcatcg agctgttgta      7080
aatacagaaa atgccaggat gtctgtggct tcgttcttat gtccctgtga tagtgcaaaa      7140
atcagtgctc caaaactcct cactgatgat ggatctccaa taatttatcg ggacttcacg      7200
tatgcagagt attacaagaa gttctggagc aggaatttgg accaagaaca ttgtttggaa      7260
cttttcaaga attaa                                                      7275
```

<210> SEQ ID NO 11
<211> LENGTH: 6000
<212> TYPE: DNA
<213> ORGANISM: Petunia x hybrida
<220> FEATURE:
<221> NAME/KEY: misc_feature
<222> LOCATION: 1790, 1791, 1792, 1793, 1794, 1795, 1796, 1797, 1798,
      1799, 1800, 1801, 1802, 1803, 1804, 1805
<223> OTHER INFORMATION: n = A,T,C or G

<400> SEQUENCE: 11

```
cttttttact cttccatatt gagttcacat aatattcgtt gacttctgta ctaatggagg        60
actaagaaag ggacaaaatt agtggggata gcatataaag gaagcactaa aatacattat       120
tctcccataa tatattaacg ttatgaatac atgtaccaaa aaaacaggt tatgaataag        180
cgtcgatgaa atgaatacat tgcattgtga accatcaaa actcgaaact cgattggcta        240
attgtaaaag tgtgtgaaaa gccttcaagc actgctagaa gtgaaagaat gttaaaaagg       300
taggtttaac atatttgatt agacacagat cttaaatata ttattataat atttatgaac       360
tataaaagct tatcgttaaa agtaaataat ctcttttcaa atcaaaaaga gttttttttt       420
ttccttttaa atgagctata aaaagataaa ggtcacatca attgaaatgg aaatagtgta       480
tgtccacctt tcaatattgt ctataactcg aaatcaaaga cgttggtagt ctcacgtttt       540
accttacgtt ggtccaatta tagtttaatc aattaagttg gtataaaaca aaaagataat       600
gcgaacaatt aatgttaata ttgtgatttg gtgcatgtga aagaatcaac atccctata        660
```

```
tagcttgagc tttcctgtga acttcttgca cacatctcta gcattaacca ttctcctgca    720
ctctcaacta cagctctttc tttatgttct cgttatatat aatatatatt catgaatgga    780
atctaatgtt atttccagcg gaaccaaata cacaaacctc cctaaaagtt atgttcgccc    840
agaatcccaa cgacctcggt tatctgaagt agacgattgc caagataata ttccagttat    900
tgatttgtgt tgcagagaca ataacgttat cattcaacaa attgaagaag cttgtcgtct    960
ttatggcttt tttcaggtac ttacacttac acataaaatt atgagttacc tttcactggc   1020
ataagtacta aaaaaattgt gccataaaaa attggataga tgagaagaaa atcagctcgt   1080 atttatttt  tctggaattt aaatcttctt gtagctcaac agtcaaacaa gactcgcctt   1140
tggatgcaat tcattaaaaa tattaaagta aatttttttt ttgtgacata tcttctctcc   1200
tttttttttt ttaaaaaaaa attaaaaacg aaatattata tattaaggga tgctcacaat   1260
tagaagcaaa ggctacgttg agcatcaaag ataccaaagt accaaagtta gctagcatat   1320
tacagatccc aaaagagatg tttgcatcat tcacaaaagt agtagtacta ctagtagaag   1380
gcgactgaag aaatacacac tctagagcta ctataattag tgagtccatc attcacaaaa   1440
gtagtaataa tactagtgac gggccttctc atcattttaa tggaacttct tgatgatcag   1500
gtaataaacc atggtgtacc aaagaaacta atagaggaaa tgctaggggt agctcatgag   1560
tttttcaagc taccagtgga agagaagatg aagttgtact cagatgatcc atcaaagacc   1620
atgagattat caacaagttt taatgtgaag aaggaaactg ttcataattg gagagactat   1680
cttagattgc actgctatcc tttggagaaa tatgcccctg aatggccttc tactccctct   1740
tctttcaggt aagtaaacgc ctttaaagcc cgatagcttt ttttttttn nnnnnnnnn    1800 nnnnaacta caaacaacat gccatatttt tttttatgca tatcacatat tcttaaaatt   1860
acaaatttta gcactcctta aaaaaaaaaa cttagctaca aaactcaccc tctcctgcca   1920
ttgagccgcc gacagacacc ctccccgcac cgccagtggt gacattactt ttttatattt   1980
tattgaattt atgttgatga gtctatataa ttacttaga  taaatttata cacacaaatt   2040
tctcctcaaa aaataaataa tacatgaata tatgtatata aatacatcgc aataagagaa   2100
atataaaaat atatacacaa aaaagtaaa  aattcatata aacatcctta atatacaaat   2160
ttatatattc gcatatatat acttatacaa atttatataa ttttatacac gtgtaaaaaa   2220
ttatataaac ttgcggcatg ctgctttctc gggaagatgg tgacatgtcg ggtaacatcc   2280
gaaaatatga gacattttg  gtaattttca ttttgcttg  tctttagcg  taattatccc   2340 ttatttttt  tatttttct  atgtactcct tccgtcataa tttatgtgac accattttct   2400
tttttgttta tctcaaaaag aattacacat ttctttattt gacaattatt taatatacca   2460
tctttatttt acatttgttg gattctacat acttttaaag ctaccaacaa ttttgtatt   2520 actcaaatat tctctttctt attttttcaa gagtaaaatt gaaactttac aaggtcaatc   2580 tctattttc  ttaaactcat tagtaccaca taaaatgaga aggatggatt ataatttatt   2640 cttcttttt  agaaaggtgg agtaaaatat tctgtgaaag tacaccaatc gattttgtga   2700
ctgtcaatac ttatatggtg gaataacata tctaaattag tcagggtccc aaaagtatac   2760
ctcactaaca atgaactaga ttatgtcaaa cgttgtatcg ttagttgcac tagaaaatta   2820
atcgtatcac tgatactctt ttagtattct taaaattgac gaataataca tttctagccg   2880
gtatgaagac cttcttttc  ccttttcttt aataggttct ctatttgggg tctttaattt   2940
aatctagcta ctatttagtt ttgacccttta atataattca gaaccctcat gtaacgttac   3000
```

```
agaattacat gcaaaactaa agaagatgaa gatctaatta aattgataac tcgaactttg    3060
tatttgttcc ctgtttgcca tgtccaaaag tccgtccgcc atgacttcac ttgtatgatt    3120
tgcaagttga actgtggaat tcgattaca  aatacaactt gtcaagtata gtattttaaa    3180
ttaaacataa aaaatgaatt tgcattgaga acttatagta attttttttca attaagatta   3240 tttagtgaaa ttaatcttca aatgcaactt gaacatctat aatgtttaaa ggcctttat    3300 cgttagtgac gccatatgga tgacttgggc tgatgacacc aatgtgatga tgattgattc    3360
cttagttaac aagtacctat agtactagga aacagcgact tttggatatg ttgttagtaa    3420 tttttttaaag taatattttg aaatcagcat ctttggatcg atttcccagt ggatgtataa   3480
gagtcacttt attttttctct tatcatgccc attaattaat tttttaaatt tttttacaac    3540
taattattat gtgtattata tctaattgtg tccttattta ctaaccttgc tgaccaagtt    3600
taagtacatt aatcttttct tacctcttta atcaagggta agattagaaa aaataatta    3660 attttccatt gattttctaa agtgatagga gtacttattt tgggacaact aaaaagagaa    3720
aattgatatt tattaaggac ggatggtgta tgatagaata ctaattttt tatggaaaat    3780 agaaatgtat cattttgtat ttgaaaatag tttaccttta gattgtcgat cattctctta    3840
aattcatgat tttatagcta tagaaatgta attgttggtt taaagctcaa gttttcaaga    3900
atttcctcaa tttttttttg tctatactca aataagttca caataaaata aatagatgga    3960
aactcagcat cctcgctaag caaatatata atacatcaac aaaacacgtg agagttgttt    4020
ggtatgcaag gaagtgacat tagaccatag tgattcggtt tgaactctta gcttgtccgc    4080
ctaaacacaa aatggacaat atcagtagta gatttgacgg tttaatattt tcaaattgca    4140
ttttcaattt taactgaaaa atgaatctta taacgttatt aatattttcg ttgacaggga    4200
aatcgttagc agatattgca tagaagttcg acaacttgga tatagattac aagaagcaat    4260
atcagagagc ttaggcctag agaaagattg tataaaaaat atattgggtg aacaaggtca    4320
acatatggct gttaattatt accctccatg tccagaacca gaactaactt atggtttgcc    4380
agcccatact gatcctaatg ccccttactat acttcttcaa gacttgcaag tagcaggtct    4440
tcaagttctc aaggatggta aatggttatc tgtgaaacct cgggccaatg cctttgtcat    4500
caatcttggt gatcaattgc aggtaaagta tatctctttc attcaacata atttaatttc    4560
tatccacctg acagtttaag atcaatttca tcacttatca ggtcacataa aaagtactat    4620
agttatgcta taagtatata tcaaacctag cttgttaaac attatgtaca cattatagaa    4680
cataaactca tttcaaaata ttactttaac aagtaacata atgtataaaa ggcccgtggt    4740
tatcctgcag gcgctgagta atggaaaata tagaagtgta tggcacagag ctatagtaaa    4800
ttcagacaaa ccaaggctgt cagtggcttc tttcttgtgt cctagtgatt gtgcgataat    4860
cagtgctcca aaaaccttaa ctgaagatgg gtctccaacc atttatcggg atttcacgta    4920
tccagaatat tacaagaaat tttggagcag aaatttagat caagaacact gtatggaact    4980
tttcaagaaa ggaagctagc ttagtgttta tgtccagcaa tttcatctgc ttacttaagt    5040
tcgcgcaggg gtggaggtag ggttttattt ggtagaaccg aataactttc tcaaatcatg    5100
tgtatgtgtt ttaaaaaata tattaagtat gaacaaatta tgaacttagt taatagcaca    5160
tgaacacctg tattagaatc cagaactaat aaatttcaaa tccttaataa atcgggcggg    5220
tagccatccg accctctaat aagtgtctta ggagatttgt gcaagcattt ttctttgtaa    5280
aagtttcctt ttcttgttgt attggaaaaa ctttttctga aacaagatcc aaggcaactg    5340
tcctgtccat atattgtcta attggaaaag ttcataattc acttgaagaa ttccataatc    5400
```

```
caaatgctaa aagcaaaata tgccttgcga aattctgtga aaccagccat gaataatcca    5460
ctgcaagaac ataatttatc accatttcac gtaggttcat aagcatcaac taaagctaac    5520
tgattagtta caaccaatt aggactataa tgatgccgaa gatgagacag gtttaatagt     5580
gatatgaact ctaccatgt taactgaaaa acaaactcgg gtttcaggta aaatatggt      5640 cacagtgtga ttcacacgaa taggctattt tcatgtgttg tttaagtttt ttaaatttgc    5700
gaaagattaa tctcacttat ttgagttttg gcagacgcat gttaacaatc tcattacaag    5760
ttttgattga tccgtcaaaa gtatatatgt taacaactac tgaatcgtta aaacctgggt    5820
acactattaa aaaattacaa gtttgacatg tccatcatac actggtaaac aattgaactt    5880
ttgacacatt catcaaactt gcaaatattg ctatttctta cacaatgtca taacaaggtc    5940
aaaacttaag cagaaccatg ccaaatggcc acctgatcaa tttatttctg atagacaata    6000

<210> SEQ ID NO 12
<211> LENGTH: 4224
<212> TYPE: DNA
<213> ORGANISM: Petunia x hybrida
<220> FEATURE:
<221> NAME/KEY: misc_feature
<222> LOCATION: 1015, 1016, 1017, 1018, 1019, 1020, 1021, 1022, 1023,
      1024, 1025, 1026, 1027, 1028, 1029, 1030
<223> OTHER INFORMATION: n = A,T,C or G

<400> SEQUENCE: 12
atggaatcta atgttatttc cagcggaacc aaatacacaa acctccctaa agttatgtt     60 cgcccagaat cccaacgacc tcggttatct gaagtagacg attgccaaga taatattcca    120
gttattgatt tgtgttgcag agacaataac gttatcattc aacaaattga agaagcttgt    180
cgtctttatg gcttttttca ggtacttaca cttacacata aaattatgag ttaccttta     240 ctggcataag tactaaaaaa attgtgccat aaaaaattgg atagatgaga gaaaatcag    300 ctcgtattta ttttttctgg aatttaaatc ttcttgtagc tcaacagtca aacaagactc    360
gcctttggat gcaattcatt aaaaatatta agtataatt ttttttgtg acatatcttc      420 tctcctttt ttttttaaa aaaaaattaa aaacgaaata ttatatatta agggatgctc     480
acaattagaa gcaaaggcta cgttgagcat caaagatacc aaagtaccaa agttagctag    540
catattacag atcccaaaag agatgtttgc atcattcaca aaagtagtag tactactagt    600
agaaggcgac tgaagaaata cacactctag agctactata attagtgagt ccatcattca    660
caaaagtagt aataatacta gtgacgggcc ttctcatcat tttaatggaa cttcttgatg    720
atcaggtaat aaaccatggt gtaccaaaga aactaataga ggaaatgcta ggggtagctc    780
atgagttttt caagctacca gtggaagaga agatgaagtt gtactcagat gatccatcaa    840
agaccatgag attatcaaca agttttaatg tgaagaagga aactgttcat aattggagag    900
actatcttag attgcactgc tatcctttgg agaaatatgc ccctgaatgg ccttctactc    960
cctcttcttt caggtaagta aacgccttta aagcccgata gcttttttt ttttnnnnn    1020 nnnnnnnnn aactacaaac aacatgccat atttttttt atgcatatca catattctta    1080
aaattacaaa tttagcact ccttaaaaaa aaaaacttag ctacaaaact caccctctcc    1140
tgccattgag ccgccgacag acaccctccc cgcaccgcca gtggtgacat acttttta      1200 tattttattg aatttatgtt gatgagtcta taattact ttagataaat ttatacacac      1260
aaatttctcc tcaaaaaata aataatacat gaatatatgt atataaatac atcgcaataa    1320
gagaaatata aaatatata cacaaaaaaa gtaaaaattc atataaacat ccttaatata    1380
```

```
caaatttata tattcgcata tatatactta tacaaattta tataattttta tacacgtgta   1440 aaaaattata taaacttgcg gcatgctgct ttctcgggaa gatggtgaca tgtcgggtaa   1500
catccgaaaa tatgagacat ttttggtaat tttcattttt gcttgtcttt tagcgtaatt   1560
atcccttatt ttttttattt tttctatgta ctccttccgt cataatttat gtgacaccat   1620 tttcttttt gtttatctca aaagaatta cacatttctt tatttgacaa ttatttaata    1680
taccatcttt atttacatt tgttggattc tacatacttt taaagctacc aacaattttt   1740
gtattactca aatattctct ttcttatttt ttcaagagta aaattgaaac tttacaaggt   1800
caatctctat ttttcttaaa ctcattagta ccacataaaa tgagaaggat ggattataat   1860
ttattcttct tttttagaaa ggtggagtaa atattctgt gaaagtacac caatcgattt    1920
tgtgactgtc aatacttata tggtggaata acatatctaa attagtcagg gtcccaaaag   1980
tatacctcac taacaatgaa ctagattatg tcaaacgttg tatcgttagt tgcactagaa   2040
aattaatcgt atcactgata ctcttttagt attcttaaaa ttgacgaata atacatttct   2100
agccggtatg aagaccttct ttttcccttt tctttaatag gttctctatt tggggtcttt   2160
aatttaatct agctactatt tagttttgac ctttaatata attcagaacc ctcatgtaac   2220
gttacagaat tacatgcaaa actaaagaag atgaagatct aattaaattg ataactcgaa   2280
ctttgtattt gttccctgtt tgccatgtcc aaaagtccgt ccgccatgac ttcacttgta   2340
tgatttgcaa gttgaactgt ggaatttcga ttacaaatac aacttgtcaa gtatagtatt   2400
ttaaattaaa cataaaaaat gaatttgcat tgagaactta tagtaatttt tttcaattaa   2460
gattatttag tgaaattaat cttcaaatgc aacttgaaca tctataatgt ttaaaggcct   2520
tttatcgtta gtgacgccat atggatgact tgggctgatg acaccaatgt gatgatgatt   2580
gattccttag ttaacaagta cctatagtac taggaaacag cgacttttgg atatgttgtt   2640
agtaattttt taaagtaata ttttgaaatc agcatctttg gatcgatttc ccagtggatg   2700
tataagagtc actttatttt tctcttatca tgcccattaa ttaatttttt aaattttttt   2760
acaactaatt attatgtgta ttatatctaa ttgtgtcctt atttactaac cttgctgacc   2820
aagtttaagt acattaatct tttcttacct ctttaatcaa gggtaagatt agaaaaaaat   2880
aattaatttt ccattgattt tctaaagtga taggagtact tattttggga caactaaaaa   2940
gagaaaattg atatttatta aggacggatg gtgtatgata gaatactaat tttttttatgg  3000 aaaatagaaa tgtatcattt tgtatttgaa aatagtttac ctttagattg tcgatcattc   3060
tcttaaattc atgatttat agctatagaa atgtaattgt tggtttaaag ctcaagtttt    3120
caagaatttc ctcaattttt ttttgtctat actcaaataa gttcacaata aaataaatag   3180
atggaaactc agcatcctcg ctaagcaaat atataataca tcaacaaaac acgtgagagt   3240
tgtttggtat gcaaggaagt gacattagac catagtgatt cggtttgaac tcttagcttg   3300
tccgcctaaa cacaaaatgg acaatatcag tagtagattt gacggtttaa tattttcaaa   3360
ttgcattttc aattttaact gaaaaatgaa tcttataacg ttattaatat tttcgttgac   3420
agggaaatcg ttagcagata ttgcatagaa gttcgacaac ttggatatag attacaagaa   3480
gcaatatcag agagcttagg cctagagaaa gattgtataa aaaatatatt gggtgaacaa   3540
ggtcaacata tggctgttaa ttattacect ccatgtccag aaccagaact aacttatggt   3600
ttgccagccc atactgatcc taatgccctt actatacttc ttcaagactt gcaagtagca   3660
ggtcttcaag ttctcaagga tggtaaatgg ttatctgtga aacctcgggc caatgccttt   3720
```

| | |
|---|---|
| gtcatcaatc ttggtgatca attgcaggta aagtatatct ctttcattca acataattta | 3780 |
| atttctatcc acctgacagt ttaagatcaa tttcatcact tatcaggtca cataaaaagt | 3840 |
| actatagtta tgctataagt atatatcaaa cctagcttgt taaacattat gtacacatta | 3900 |
| tagaacataa actcatttca aaatattact ttaacaagta acataatgta taaaaggccc | 3960 |
| gtggttatcc tgcaggcgct gagtaatgga aaatatagaa gtgtatggca cagagctata | 4020 |
| gtaaattcag acaaccaag gctgtcagtg gcttctttct tgtgtcctag tgattgtgcg | 4080 |
| ataatcagtg ctccaaaaac cttaactgaa gatgggtctc caaccattta tcgggatttc | 4140 |
| acgtatccag aatattacaa gaaattttgg agcagaaatt tagatcaaga acactgtatg | 4200 |
| gaacttttca agaaaggaag ctag | 4224 |

<210> SEQ ID NO 13
<211> LENGTH: 10007
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 25, 26, 27, 28, 29, 91, 92, 93, 94, 95, 96, 97, 98, 99,
       100, 101, 102, 103, 104, 105, 106, 107, 108, 109, 110, 111, 112,
       113, 114, 115, 116, 117, 118, 119, 120, 121, 122, 123, 124, 125,
       126, 127, 128, 8463
<223> OTHER INFORMATION: n = A,T,C or G

<400> SEQUENCE: 13

| | |
|---|---|
| ggttcttgat attcatgcat catannnnnc tttaacttgt ttaatttaac tgctttgcag | 60 |
| gtgtttggtt cttgatattc atgcatcata nnnnnnnnnn nnnnnnnnnn nnnnnnnnnn | 120 |
| nnnnnnnntt acgcgcggga tcttctagct caatatcaga agggaagctt aactaatcgt | 180 |
| tcaaggtaga ggatcatgca aagcaatata gagatagctg tgcaacttgt tacaattatt | 240 |
| taacaacgct acaatattaa ccatggctat ggcaataaat actactcgta taaaaagcct | 300 |
| tccataacac acacagtaaa aaaaacaaaa aagaataaac aaaaataaaa cacaaataca | 360 |
| atacgtacat acatacagac atatacataa tatatagact cacagacacg attaaatatc | 420 |
| agtaaattgc ttcagctcat tttcaaatta aaaagaaaaa aaaacgact ttctttgcct | 480 |
| ttggaaatat gattgaatct gcttgagcta atcaattttt taatgtggtc aatattacat | 540 |
| aattatttca aaattaattt ttagcattta tcatccttgc actgacctgt acggagatat | 600 |
| aattaagaat gagtaaaagt atataattag ttgtagaaag ggaggaacat tattcgttta | 660 |
| caaatctatt aatgataaac aaggattata tgaaaaaatg catgaaactc atagaaaaat | 720 |
| ggtcttagat acaataaatg attctctctc tatcacaaag ttaatttgca tatataaaat | 780 |
| gtaataaata aattaagatt tttgtaaact cgtgactaaa ataagctata agtatttgtg | 840 |
| tagttgtaaa taaataaaat gagaatattt aagtaaaatt attttcaaat tgaaaaatat | 900 |
| gagaattctt ttttttttaat gaatgaaata ccttcaaata tagggtcaag tcatactcac | 960 |
| acttgtgaaa ctccgttata ggtgacgaat taaacatgac gtaagtaaat taatacggcg | 1020 |
| agccttgcag cttgcctata taacttgg aaatttccta gaaactgaaa atctgagttg | 1080 |
| tgggcaattc ttttcgttcc caaatcacaa ataatttttt tctttatatg cgagtcaaaa | 1140 |
| tcagattcaa tggaaacaaa agttctttca agtggaatcc gtcattctac cctccctcaa | 1200 |
| aattatgtcc gacccaaatc cgataggcca cgtctttcag aagtggccaa ttgtgaaaac | 1260 |
| gttccagtta ttgacttggg ttgtgctgac agaactctca taattcatca aattagcgaa | 1320 |

```
gcctgtcgtc tttatggttt tttccaggta aacataatta atcatttctg tttcttcatt      1380
atcaaaatct acatttatgg taaccaattt aactttatgt ttaggtaata aaccatggtg      1440
taccaaaaaa aatagttgag gaaatgctag agatagctgg ggagttttt aggctaccag       1500 ttgaagagaa gcttaagttg tattcagatg tgagatgacc cttcaaagac catgagatta     1560
tcaactagtt ttaatgtaaa gaaggagacg gtgcacaatt ggagagatta tctcagactt     1620
cattgttatc ctctggagaa atatgctcct gaatggcctt caaatccttc atctttcagg     1680
taaacaccat taagactctt cactaagctt tcttcttggg ttaatctggt ttcatgtgtg     1740
ttggtggata catttgctat ccgagtcata tattttatcc ttatctacgt caaccatgtt    1800
tgtttgttgt actataatca ctaagcactg catggatgca aaactaaaat aacattattg    1860
tgcgttgcac gtaataatat gttgcaataa tatgttgtca tctatataaa ttgtttatac    1920
atattaaata aataaaatat tctaaaagaa gtatattctt tatgagcata tatcaggtac    1980
gtatcaggtg tttgtttgtt tgtcctacat gatatataat caggtgtttg tttgtttgtc    2040
ctacataata taataaaat actagacgaa atatatcgca tcaatattaa gaaatattta     2100
gagttataaa ttatctgggc acgtgtcagg tgtttgtctg tttgtcctac atgatatgta    2160
ataaatacca gaagaaatat tcctaaaata tccatcaata ttaagaaata tttagagtta   2220
taaattatct gggcacgtgt gagacacgtg tcaagtgttt atctgtttgt actgaaggta    2280
tatgataaat actcaaaaaa attaaaatat tgactcgcta ttaagaaaat atttaataat    2340
ttatattact agtacattag tagtaattgt tttgattatg gagtatacta atacaatact    2400
atttcactct agcgaggtcg ttttgaaaat agagggtcaa tcattctaaa aattgatatg   2460
attaaaataa acctttttat tgatctgaca aaaaccattt agtctctcta agactctaac    2520
cttctaagta gtaatgtaaa aagtccttga gagttttaag agaatgcatg ttccatgtga    2580
atgtgccaac catttctcat ttcttcacct tttcctttt atattttcca tatcttatga     2640
atatttaaga agtatcaagt tggagttgtc caataggatt acttagtaat cgaaaatgaa    2700
atggagcaag attatggagt cttgaccttg acactggttt tgttgatgct ccttatgata    2760
gaattgcaag aactaatggc cacggaagct attgtacacc attttagaa gttggattct     2820 ctatatagag cttgagttcc taattcagta ttattttaca tgttcttctt atataggtaa    2880
gtttaaaaaa tacaatgtag gtacactgag taaattatag aaaaatcgag ataggtaagt    2940
tgagctacaa ttggagaaag gaaagtactc ctccgtccca aattagttga cgttttagca    3000
ataattattt aactcaaatt ataccccttaa taattaaaat aattctcaac aaaatttaat   3060
agacaaactt aaatagggt aacatagtaa aatatacacc ttattaatga tttcttaatg     3120
gacgtgaaaa agctgaaggc gacaattaat ttgggacgga gggagtagaa atttgagtgg    3180
acaaggggta gacgttagag ataacagaaa agaagcatgt gaaaaaagc atgtgaggcc    3240 acatttgact attctagatt taatcctatt gattgaaatt aaaacttcca tcaacttatc    3300
ttgcagccat gtgctgccaa ttaactagca ccttcttcgg tgccaaaacc caaatttct     3360 ttttcttcaa cttacaaaat ggctatttgt tacgtcatgg ctaacgaatt tgatgacatc    3420
atgtttgttg ccatattagc ccagtaatcg acacgtaatc aatgattgtg tcaccatcaa    3480
gatgaagtca tttggtagat agttggtggc ataagcagac aatggaagta aatgttggat    3540
agccaaactt gtgattttg tgtcggctag tatccatagg ggatgcgatg acttccagag     3600
tctcctttaa atgaatactt taggaaagaa cttactaaaa gattctcaaa aaagtacttt    3660
gatttttagt taatatagta catctatttg ctacagaaaa agtactttta gaaaatgaaa    3720
```

```
taaagagtac tctagcgagg atctaaaaaa tgtccgcttt accattacag gccccgtgat    3780
tttcgtgctt cttgtgcctt gtataatttc ttcttcgcct gggaaagtaa agaaaagtag    3840
gcttaagtaa agaggaatgg agaaaacaaa aaagttactg tactaattaa aaggataatt    3900
aaaagagaaa atttattcga ataaagaaaa aacaaaataa tccataaaaa attaataggg    3960
gaatcccttc gagaaaatta ataacggttt agctgagacc taacatccaa tatattttgc    4020
acaagtcttt ttgtaatgaa attttcttga gaatcgtcct aaacctagct agtagaagtt    4080
aacgtaggca taatctactc gctgccaaca cactgctcca attaagccga caacggcaa     4140 acagcataac aataaacaaa gataagtggg ttattggttt tagtatagtc tagagtaccc    4200
cgcataggct gtatcatcca tttcgaattt gtgtccagaa aaatacttcc gctatttcat    4260
tttatatggc aagatttaaa atgcgagagt caaacttgtt agctttaaaa tattttaaga    4320
aaatgtaatg aaatatttaa taaaaatgtg gtcgaaactg aaataaagac tccatagact    4380
cctaagctag cgtttggaca tagatttggg tagaaagttt gtgagggaaa aaaaaaaact    4440
cccaaattct ggtttcaacc ggaatgtggg attttgaagt tttggagaaa ttctataaac    4500
aaataagttt ttaaaataat actccccaaa tttttatgtcc aaacggggag taataataa    4560 tatggcacat aaaatggagt agtccgccaa tggtaaggga ttaagatctg gtcatgaatt    4620
atttttccat accaatttgt ttatacgttt attgggtaga tgacttaatc atattcttaa    4680
gaaatcaata gtagtactta atgaaggtgg gtgagcaatc aagatctctg aagcataata    4740
agtgagaata agcagctaaa acgcgtttta aaggacttag gtaccaaatg aaaaagacct    4800
ggaacataaa atcaatggcc taacgtaagc caaggaataa tgggggtttat ggttcaatca    4860 tggaccattt gattaagttt ttatacatga gaatgaatgg cgtatagtag aatccgacgt    4920
atcatatcta cttgtttatt catttcttgt gttgtagggg ttcttaatt tactaagtac      4980 atcgtgaagg tcaccatcaa aactgatccg agctagtctt tacattaatt aagagcagta    5040
aattgaaatt tgtcaatgct aattgcggct gttctcacgc gttgttaaat gatgttagcg    5100
tgctaattgc atctctgtaa acttccaaat tgttgtgcta ccgacgtgtt atcttttca     5160 aattttcttt agatagagat ggactttgga ttacagtaga ggaaaaagta gagaggagac    5220
tatcccattc aacctattga ccatttgtcc tattgcatca cctgtttgta ttggttgctt    5280
tggtcatggt ttgttattgc taaaatttgt gttagagcga atttctgggt agattgtcat    5340
atttagcccc agaaaagaat attatgcaaa aagtgaattc cttgtgatca gtaatgacat    5400 tttttttacta cagtcctgac aatttgctag aaggtgcctt aaattttggc ggagaagcta    5460
caaccaactt ttttttttcag aggattaaag ttaaaagag gcactaaaat agtctatcca    5520
tgcaaatatc cctctttttt cggggggaagt gcaccaaagg ccacatttgc cagtggtctt    5580
tagtttgaag ccacttttt tttattgatt ttacataaaa gatcacttt tgaaatatca      5640 attcttttgg cttgaacttc acacgagttc agcccacaag gattaaagtt caacttcagc    5700
ccaccacaag gattgaagtt gaacttctat acctaaaagt ttagtcctta ctgattgaag    5760
ttgagacttc ataatttagg catgaagttc aatctacatg gtttgaattt cagctcacaa    5820
agattggagt tccaaaaaaa tgacctctca tataagacaa ataaaaaagt gacttaaaac    5880
taaataccag taaaaaaaag tggcatgtgg gtaaaaattt cacttttta ttgacagtat     5940 aagcatcggg atatttgtag taatagaata tttcagtgct actatttaac ttttttatccc   6000 atttcaagaa tttaacttttt agactctggc actagaattt ggagccactt cctaatggat   6060
```

-continued

```
taccaggatt cacttcataa aggtcctaac aagtccttat ggatagacat aaagagctaa    6120
ataattaacc cttctttctt aggagcctaa aaaaattaaa cacagctgcc agcgccagtc    6180
tcccacaaca gtggtttaac aaaatagcat ttgcatgatt ttataaatga atttcggtcg    6240
aaaatagccc tacgaattat ataatgacgc ccgcatctaa ctttctttct cgtaagtaca    6300
ggcagcactt gcctcctatt gcttaggcaa catttgcact gaaatctctt tcaagatcct    6360
tatagataac ttgaattgtt gcctaggcaa tacttgtggt tgaaatcttg cctaggcaac    6420
aattgacgtt gaaaaatgct tatctaggta acacttgtct tttgacctct tttcacgttc    6480
tttcatataa cttgaaatat tgcctatgga cgaagcggag ataattttgc taaaatcatc    6540
ttaaacgtgg acaaactctt aaaattagtc aattttgagg atacgagtga aactttttaa    6600
aatatgtgtt gtaatacgca ctattagccg ctttgtgtta tgcatttaag tgcagggaaa    6660
gtgcaggaat agcttttttt tttttttgc ccgcattata gtttataagc tattttaaa     6720
aaattattta gttttagtc acttttaaa tttcaagcct tgggtctgat ctttaaatct     6780
tcagagttga agttcaactt cagaccttca ggtcttaact taagatattt tatgcctaat    6840
ttcaaacttc aagtttgaag ttagatatgg aaggtttgaa gtttgatata gtgactaaaa    6900
accacatctt caccaaaatc ttgtactcta ttacatattg gggaggggaa agaaaaagaa    6960
aaatgataga agagctgatg agaatcgcac tcactctacc agctggttag agtcctctag    7020
gtaattttga ggaaattcaa gttggctttg aaatgtgtaa cctggcaaca ttaaaataac    7080
atagcagttt gtaccttata ttatatatac tcattgtaca aggaatgttt gagcaattaa    7140
tatagttaat tgaggtctaa catgctattt ttgatattat aagttttaga cattgtcagt    7200
ataacttta taagttattg tctacactag taaggaataa taactgtagt cagattttca    7260
attcatgctt gtagtagagg ttcttaaaaa cttgatagcc caacaattgt tcatgtctaa    7320
attgctaatg agttgattta tttgtctccc tgttagcctg tttccctcg tagcatgctt     7380
agccaccagt aacagcttta tgcatgcttc atttctgcaa ttaacaataa gttcctccat    7440
gcttattaac aagtttctgc atttaacagt tttcttggca cataatatct tttaattgaa    7500
aataaaaata atcttatttg tcaatgttct ggttgacagg gaaatcgtga gcagatattg    7560
cacggaagtt cgacaacttg gattcagatt gcaagaagcc atagcagaaa gcttaggctt    7620
agagaaagag tgtataaagg atgtgttagg tgaacaaggt caacatatgg ctataaactt    7680
ttatcctcca tgcccagaac cagaactcac ttacgggctg ccagcccata ccgatccaaa    7740
tgctcttaca attcttcttc aagacttgca agtagctggt ctccaagttc ttaaagatgg    7800
caaatggttg gctgtcaaac ctcagcccga tgcctttgtt gttaatctcg gtgatcaact    7860
gcaggtaaaa cagaattaac gctataatta aattagttac ttatatgcaa ctgaatgcat    7920
acattaaata tttaacttgt atacagtttg aagaaatatt acagtatcat agtagtattt    7980
taacacgtag tagtaggtta ttgcctttca tggcggatga aacctttgct caacgggttg    8040
aactgaacct aaaatttgta aaattgcgaa attctattat aatctcaaca aatgttagat    8100
tttgaaacca taatttcagt gtgcgatcag ttataaaagt taaactcata ctctaaacta    8160
atgctcgttg gtcacggtca ttctgcaggc agtgagtaac ggaaggtaca aaagcgtatg    8220
gcatcgagct gttgtaaata cagaaaatgc caggatgtct gtggcttcgt tcttatgtcc    8280
ctgtgatagt gcaaaaatca gtgctccaaa actcctcact gatgatggat ctccaataat    8340
ttatcgggac ttcacgtatg cagagtatta caagaagttc tggagcagga atttggacca    8400
agaacattgt ttggaacttt tcaagaatta aagctagtat ttaaaaaaaa aaaaaaaaaa    8460
```

```
ccntatgggg tgagaattag attagaaaat aaaaacagtt atatcttcat tgcttagctg    8520
atttacccaa ttacaataca ctggcctgtt tggcaagttg ctaataagca gtagcaattg    8580
gctagaactg gactacaaga tctatttgga agaggaatta caagggtcca gtatccagat    8640
ttgtttgtgt aggaataata tatacttatt ggttatttct ttccctgatt ttacttcctt    8700
ctatggaagt ttacgtgtat cctatgaatt attttacttc tgtacttgta gtatatatga    8760
tttaccgcgc aaaagaataa ttaatctaag tttgttgata tcctgaagta tactggaaca    8820
aaaatacatc tacttattgg gcactggaag ttggaccaag tccaagatct acacttgaac    8880
gatgggttac gcccaaatca ctatgtaagc aaagacttcc agtatttgat caagtaaaca    8940
gagattttaa agctagaaaa attagcgaat gacttttttct gcgaatcatc cttggaaaga    9000
attagctcta atgaatatat ggacaattag tcgataatgt gctgaagtaa agaaggaaca    9060
gctgaacaaa gccacctaat atccaggact tctacattaa acacattcct taatctaaat    9120
aacttcagcc tttcatctcc tgtgacctaa tatctttaaa ttaatcatca aatctttagt    9180
taatcccaaa actataatct catttttctag gtatcccact ttattccacc aaccaaacat    9240
gcgtaagttc ctttcttttg tcaaagcatg tgacctttac caacttctcc taggaacttt    9300
tgtaaagtga tcggaatttg gagcgaaaca tagttgcgga ccaaaagtat tttcctcaaa    9360
gtgattgtgt gaacactgat aatcataatt atgatttagg tgtccatcag cttcatagtt    9420
ggcccaactt agaattttt agcaccaaac tgtataattg caaacactcg tactgaatac    9480
atttggctac ttccaattgg ccatttagtt tccaaattat tttaagctg agccctacaa    9540 ctcctttcga atttaacttt ttcttttttg gtaggacatg atcagatcat ccaagaccat    9600
ttgctttcat atggctgtta cttgatgtga tcatgtttac ttaagtttag tttaattttg    9660
tatgaccaca cacttgtctt aacaatcaaa ttttacaaca tcctactagt acatgtaaac    9720
tatgtctgag tcttaagagt atgattggtc gaaagtaaat gattagtaca tgtgtgttac    9780
agaaatacat atactataat aaaattcaaa gccagctaaa agaagcttca atttaaagac    9840
attgcttttc tgggagcaat tatttcatct tcctcatatc ttttgaacat caatctcttc    9900
aaggtaaaag ctaattttct tttatttcgc agtgacatgt aatacataac gctcaagcca    9960
ctctgaaaaa agcaggtcac aattgcaaaa ggagcagtat atatatt              10007
```

<210> SEQ ID NO 14
<211> LENGTH: 7282
<212> TYPE: DNA
<213> ORGANISM: Artificial Sequence
<220> FEATURE:
<223> OTHER INFORMATION: Synthetic Construct

<400> SEQUENCE: 14

```
atggaaacaa aagttctttc aagtggaatc cgtcattcta ccctccctca aaattatgtc     60
cgacccaaat ccgataggcc acgtctttca gaagtggcca attgtgaaaa cgttccagtt    120
attgacttgg gttgtgctga cagaactctc ataattcatc aaattagcga agcctgtcgt    180
ctttatggtt ttttccaggt aaacataatt aatcatttct gtttcttcat tatcaaaatc    240
tacatttatg gtaaccaatt taactttatg tttaggtaat aaaccatggt gtaccaaaaa    300
aaatagttga ggaaatgcta gagatagctg gggagttttt taggctacca gttgaagaga    360
agcttaagtt gtattcagat gtgagatgac ccttcaaaga ccatgagatt atcaactagt    420
tttaatgtaa agaaggagac ggtgcacaat tggagagatt atctcagact tcattgttat    480
```

```
cctctggaga aatatgctcc tgaatggcct tcaaatcctt catctttcag gtaaacacca    540
ttaagactct tcactaagct ttcttcttgg gttaatctgg tttcatgtgt gttggtggat    600
acatttgcta tccgagtcat atatttttatc cttatctacg tcaaccatgt ttgtttgttg    660
tactataatc actaagcact gcatggatgc aaaactaaaa taacattatt gtgcgttgca    720
cgtaataata tgttgcaata atatgttgtc atctatataa attgtttata catattaaat    780
aaataaaata ttctaaaaga agtatattct ttatgagcat atatcaggta cgtatcaggt    840
gtttgtttgt ttgtcctaca tgatatataa tcaggtgttt gtttgtttgt cctacataat    900
atataataaa tactagacga aatatatcgc atcaatatta agaaatattt agagttataa    960
attatctggg cacgtgtcag gtgtttgtct gtttgtccta catgatatgt aataaatacc   1020
agaagaaata ttcctaaaat atccatcaat attaagaaat tttagagtt ataaattatc   1080 tgggcacgtg tgagacacgt gtcaagtgtt tatctgtttg tactgaaggt atatgataaa   1140
tactcaaaaa aattaaaata ttgactcgct attaagaaaa tatttaataa tttatattac   1200
tagtacatta gtagtaattg ttttgattat ggagtatact aatacaatac tatttcactc   1260
tagcgaggtc gttttgaaaa tagagggtca atcattctaa aaattgatat gattaaaata   1320
aaccttttta ttgatctgac aaaaaccatt tagtctctct aagactctaa ccttctaagt   1380
agtaatgtaa aaagtccttg agagttttaa gagaatgcat gttccatgtg aatgtgccaa   1440
ccatttctca tttcttcacc ttttcctttt tatatttttcc atatcttatg aatatttaag   1500
aagtatcaag ttggagttgt ccaataggat tacttagtaa tcgaaaatga aatggagcaa   1560
gattatggag tcttgacctt gacactggtt ttgttgatgc tccttatgat agaattgcaa   1620
gaactaatgg ccacggaagc tattgtacac cattttttaga agttggattc tctatataga   1680
gcttgagttc ctaattcagt attattttac atgttcttct tatataggta agtttaaaaa   1740
atacaatgta ggtacactga gtaaattata gaaaaatcga gataggtaag ttgagctaca   1800
attggagaaa ggaaagtact cctccgtccc aaattagttg acgttttagc aataattatt   1860
taactcaaat tataccctta ataattaaaa taattctcaa caaaatttaa tagacaaact   1920
taaatagggg taacatagta aaatatacac cttattaatg atttcttaat ggacgtgaaa   1980
aagctgaagg cgacaattaa tttgggacgg agggagtaga aatttgagtg acaagggggt   2040
agacgttaga gataacagaa aagaagcatg tgaaaaaaag catgtgaggc cacatttgac   2100
tattctagat ttaatcctat tgattgaaat taaaacttcc atcaacttat cttgcagcca   2160
tgtgctgcca attaactagc accttcttcg gtgccaaaac ccaaatttttc tttttcttca   2220 acttacaaaa tggctatttg ttacgtcatg gctaacgaat ttgatgacat catgtttgtt   2280
gccatattag cccagtaatc gacacgtaat caatgattgt gtcaccatca agatgaagtc   2340
atttggtaga tagttggtgg cataagcaga caatggaagt aaatgttgga tagccaaact   2400
tgtgattttt gtgtcggcta gtatccatag gggatgcgat gacttccaga gtctccttta   2460
aatgaatact ttaggaaaga acttactaaa agattctcaa aaaagtactt tgattttttag   2520 ttaatatagt acatctattt gctacagaaa aagtactttt agaaaatgaa ataaagagta   2580
ctctagcgag gatctaaaaa atgtccgctt taccattaca ggccccgtga ttttcgtgct   2640
tcttgtgcct tgtataattt cttcttcgcc tgggaaagta agaaaagta ggcttaagta   2700 aagaggaatg gagaaaacaa aaaagttact gtactaatta aaaggataat taaaagagaa   2760
aatttattcg aataaagaaa aaacaaaata atccataaaa aattaatagg ggaatccctt   2820
cgagaaaatt aataacggtt tagctgagac ctaacatcca atatattttg cacaagtctt   2880
```

```
tttgtaatga aatttccttg agaatcgtcc taaacctagc tagtagaagt taacgtaggc   2940
ataatctact cgctgccaac acactgctcc aattaagccg aacaacggca aacagcataa   3000
caataaacaa agataagtgg gttattggtt ttagtatagt ctagagtacc ccgcataggc   3060
tgtatcatcc atttcgaatt tgtgtccaga aaaatacttc cgctatttca ttttatatgg   3120
caagatttaa aatgcgagag tcaaacttgt tagcttaaaa atattttaag aaaatgtaat   3180
gaaatattta ataaaaatgt ggtcgaaact gaaataaaga ctccatagac tcctaagcta   3240
gcgtttggac atagatttgg gtagaaagtt tgtgagggaa aaaaaaaaac tcccaaattc   3300
tggtttcaac cggaatgtgg gattttgaag ttttggagaa attctataaa caataagtt    3360
tttaaaataa tactccccaa attttatgtc caaacgggag gtaaataata atatggcaca   3420
taaaatggag tagtccgcca atggtaaggg attaagatct ggtcatgaat tattttttcca  3480
taccaattg tttatacgtt tattgggtag atgacttaat catattctta agaaatcaat    3540
agtagtactt aatgaaggtg ggtgagcaat caagatctct gaagcataat aagtgagaat   3600
aagcagctaa aacgcgtttt aaaggactta ggtaccaaat gaaaaagacc tggaacataa   3660
aatcaatggc ctaacgtaag ccaaggaata atggggttta tggttcaatc atggaccatt   3720
tgattaagtt tttatacatg agaatgaatg gcgtatagta gaatccgacg tatcatatct   3780
acttgtttat tcatttcttg tgttgtaggg gttcttaatt ttactaagta catcgtgaag   3840
gtcaccatca aaactgatcc gagctagtct ttacattaat taagagcagt aaattgaaat   3900
ttgtcaatgc taattgcggc tgttctcacg cgttgttaaa tgatgttagc gtgctaattg   3960
catctctgta aacttccaaa ttgttgtgct accgacgtgt tatcttttc aaattttctt    4020
tagatagaga tggactttgg attacagtag aggaaaaagt agagaggaga ctatcccatt   4080
caacctattg accatttgtc ctattgcatc acctgtttgt attggttgct ttggtcatgg   4140
tttgttattg ctaaaatttg tgttagagcg aatttctggg tagattgtca tatttagccc   4200
cagaaaagaa tattatgcaa aaagtgaatt ccttgtgatc agtaatgaca ttttttttact  4260
acagtcctga caatttgcta gaaggtgcct taaattttgg cggagaagct acaaccaact   4320
ttttttttca gaggattaaa gttaaaaaga ggcactaaaa tagtctatcc atgcaaatat   4380
ccctcttttt tcgggggaag tgcaccaaag gccacatttg ccagtggtct ttagtttgaa   4440
gccacttttt ttttattgat tttacataaa agatcacttt tgaaatatc aattcttttg    4500
gcttgaactt cacacgagtt cagcccacaa ggattaaagt tcaacttcag cccaccacaa   4560
ggattgaagt tgaacttcta tacctaaaag tttagtcctt actgattgaa gttgagactt   4620
cataatttag gcatgaagtt caatctacat ggtttgaatt tcagctcaca aagattggag   4680
ttccaaaaaa atgacctctc atataagaca aataaaaaag tgacttaaaa ctaaatacca   4740
gtaaaaaaaa gtggcatgtg ggtaaaaatt tcacttttt attgacagta taagcatcgg    4800
gatatttgta gtaatagaat atttcagtgc tactatttaa ctttttatcc catttcaaga   4860
atttaacttt tagactctgg cactagaatt tggagccact tcctaatgga ttaccaggat   4920
tcacttcata aaggtcctaa caagtcctta tggatagaca taaagagcta ataattaac    4980
ccttcttct taggagccta aaaaaattaa acacagctgc cagcgccagt ctcccacaac    5040
agtggtttaa caaaatagca tttgcatgat tttataaatg aatttcggtc gaaaatagcc   5100
ctacgaatta tataatgacg cccgcatcta actttctttc tcgtaagtac aggcagcact   5160
tgcctcctat tgcttaggca acatttgcac tgaaatctct ttcaagatcc ttatagataa   5220
```

| | | | | |
|---|---|---|---|---|
| cttgaattgt | tgcctaggca | atacttgtgg | ttgaaatctt | gcctaggcaa caattgacgt | 5280 |
| tgaaaaatgc | ttatctaggt | aacacttgtc | ttttgacctc | ttttcacgtt ctttcatata | 5340 |
| acttgaaata | ttgcctatgg | acgaagcgga | gataattttg | ctaaaatcat cttaaacgtg | 5400 |
| gacaaactct | taaaattagt | caattttgag | gatacgagtg | aaacttttta aaatatgtgt | 5460 |
| tgtaatacgc | actattagcc | gctttgtgtt | atgcatttaa | gtgcagggaa agtgcaggaa | 5520 |
| tagcttttttt | tttttttttg | cccgcattat | agtttataag | ctattttttaa aaaattattt | 5580 |
| agtttttagt | cacttttttaa | atttcaagcc | ttgggtctga | tctttaaatc ttcagagttg | 5640 |
| aagttcaact | tcagaccttc | aggtcttaac | ttaagatatt | ttatgcctaa tttcaaactt | 5700 |
| caagtttgaa | gttagatatg | gaaggtttga | agtttgatat | agtgactaaa aaccacatct | 5760 |
| tcaccaaaat | cttgtactct | attacatatt | ggggaggggga | aagaaaaaga aaaatgatag | 5820 |
| aagagctgat | gagaatcgca | ctcactctac | cagctggtta | gagtcctcta ggtaatttttg | 5880 |
| aggaaattca | agttggcttt | gaatgtgta | acctggcaac | attaaaataa catagcagtt | 5940 |
| tgtaccttat | attatatata | ctcattgtac | aaggaatgtt | tgagcaatta atatagttaa | 6000 |
| ttgaggtcta | acatgctatt | tttgatatta | taagttttag | acattgtcag tataactttt | 6060 |
| ataagttatt | gtctacacta | gtaaggaata | ataactgtag | tcagattttc aattcatgct | 6120 |
| tgtagtagag | gttcttaaaa | acttgatagc | ccaacaattg | ttcatgtcta aattgctaat | 6180 |
| gagttgattt | atttgtctcc | ctgttagcct | gtttcccctc | gtagcatgct tagccaccag | 6240 |
| taacagcttt | atgcatgctt | catttctgca | attaacaata | agttcctcca tgcttattaa | 6300 |
| caagtttctg | catttaacag | ttttcttggc | acataatatc | ttttaattga aaataaaaat | 6360 |
| aatcttatttt | gtcaatgttc | tggttgacag | ggaaatcgtg | agcagatatt gcacggaagt | 6420 |
| tcgacaactt | ggattcagat | tgcaagaagc | catagcagaa | agcttaggct tagagaaaga | 6480 |
| gtgtataaag | gatgtgttag | gtgaacaagg | tcaacatatg | gctataaact tttatcctcc | 6540 |
| atgcccagaa | ccagaactca | cttacgggct | gccagcccat | accgatccaa atgctcttac | 6600 |
| aattcttctt | caagacttgc | aagtagctgg | tctccaagtt | cttaaagatg gcaaatggtt | 6660 |
| ggctgtcaaa | cctcagcccg | atgccttttgt | tgttaatctc | ggtgatcaac tgcaggtaaa | 6720 |
| acagaattaa | cgctataatt | aaattagtta | cttatatgca | actgaatgca tacattaaat | 6780 |
| atttaacttg | tatacagttt | gaagaaatat | tacagtatca | tagtagtatt ttaacacgta | 6840 |
| gtagtaggtt | attgcctttc | atggcggatg | aaaccttttgc | tcaacgggtt gaactgaacc | 6900 |
| taaaatttgt | aaaattgcga | aattctatta | taatctcaac | aaatgttaga ttttgaaacc | 6960 |
| ataatttcag | tgtgcgatca | gttataaaag | ttaaactcat | actctaaact aatgctcgtt | 7020 |
| ggtcacggtc | attctgcagg | cagtgagtaa | cggaaggtac | aaaagcgtat ggcatcgagc | 7080 |
| tgttgtaaat | acagaaaatg | ccaggatgtc | tgtggcttcg | ttcttatgtc cctgtgatag | 7140 |
| tgcaaaaatc | agtgctccaa | aactcctcac | tgatgatgga | tctccaataa tttatcggga | 7200 |
| cttcacgtat | gcagagtatt | acaagaagtt | ctggagcagg | aatttggacc aagaacattg | 7260 |
| tttggaactt | ttcaagaatt | aa | | | 7282 |

<210> SEQ ID NO 15
<211> LENGTH: 6007
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1797, 1798, 1799, 1800, 1801, 1802, 1803, 1804, 1805,
    1806, 1807, 1808, 1809, 1810, 1811, 1812
<223> OTHER INFORMATION: n = A,T,C or G

<400> SEQUENCE: 15

| | | | | | |
|---|---|---|---|---|---|
| cttttttact | cttccatatt | gagttcacat | aatattcgtt | gacttctgta | ctaatggagg | 60 |
| actaagaaag | ggacaaaatt | agtggggata | gcatataaag | gaagcactaa | aatacattat | 120 |
| tctcccataa | tatattaacg | ttatgaatac | atgtaccaaa | aaaaacaggt | tatgaataag | 180 |
| cgtcgatgaa | atgaatacat | tgcattgtga | aaccatcaaa | actcgaaact | cgattggcta | 240 |
| attgtaaaag | tgtgtgaaaa | gccttcaagc | actgctagaa | gtgaaagaat | gttaaaaagg | 300 |
| taggtttaac | atatttgatt | agacacagat | cttaaatata | ttattataat | atttatgaac | 360 |
| tataaaagct | tatcgttaaa | agtaaataat | ctcttttcaa | atcaaaaaga | agttttttt | 420 |
| ttccttttaa | atgagctata | aaaagataa | ggtcacatca | attgaaatgg | aaatagtgta | 480 |
| tgtccacctt | tcaatattgt | ctataactcg | aaatcaaaga | cgttggtagt | ctcacgtttt | 540 |
| accttacgtt | ggtccaatta | tagtttaatc | aattaagttg | gtaaaaaca | aaaagataat | 600 |
| gcgaacaatt | aatgttaata | ttgtgatttg | gtgcatgtga | aagaatcaac | atccccata | 660 |
| tagcttgagc | tttcctgtga | acttcttgca | cacatctcta | gcattaacca | ttctcctgca | 720 |
| ctctcaacta | cagctctttc | tttatgttct | cgttatatat | aatatatatt | catgaatgga | 780 |
| atctaatgtt | atttccagcg | gaaccaaata | cacaaacctc | cctaaaagtt | atgttcgccc | 840 |
| agaatcccaa | cgacctcggt | tatctgaagt | agacgattgc | caagataata | ttccagttat | 900 |
| tgatttgtgt | tgcagagaca | ataacgttat | cattcaacaa | attgaagaag | cttgtcgtct | 960 |
| ttatggcttt | tttcaggtac | ttacacttac | acataaaatt | atgagttacc | tttcactggc | 1020 |
| ataagtacta | aaaaattgt | gccataaaaa | attggataga | tgagaagaaa | atcagctcgt | 1080 |
| atttattttt | tctggaattt | aaatcttctt | gtagctcaac | agtcaaacaa | gactcgcctt | 1140 |
| tggatgcaat | tcattaaaaa | tattaaagta | taattttttt | ttgtgacata | tcttctctcc | 1200 |
| tttttttttt | ttaaaaaaaa | attaaaaacg | aaatattata | tattaaggga | tgctcacaat | 1260 |
| tagaagcaaa | ggctacgttg | agcatcaaag | ataccaaagt | accaaagtta | gctagcatat | 1320 |
| tacagatccc | aaaagagatg | tttgcatcat | tcacaaaagt | agtagtacta | ctagtagaag | 1380 |
| gcgactgaag | aaatacacac | tctagagcta | ctataattag | tgagtccatc | attcacaaaa | 1440 |
| gtagtaataa | tactagtgac | gggccttctc | atcattttaa | tggaacttct | tgatgatcag | 1500 |
| gtaataaacc | atggtgtacc | aaagaaacta | atagaggaaa | tgctaggggt | agctcatgag | 1560 |
| tttttcaagc | taccagtgga | agagaagatg | aagttgtact | cagatgatcc | atcaaagacc | 1620 |
| atgagattat | caacaagttt | taatgtgaag | aaggaaactg | ttcataaatc | ataattggag | 1680 |
| agactatctt | agattgcact | gctatccttt | ggagaaatat | gccctgaat | ggccttctac | 1740 |
| tccctcttct | ttcaggtaag | taaacgcctt | taaagcccga | tagcttttt | ttttttnnnn | 1800 |
| nnnnnnnnnn | nnaactacaa | acaacatgcc | atattttttt | ttatgcatat | cacatattct | 1860 |
| taaaattaca | aattttagca | ctccttaaaa | aaaaaaactt | agctacaaaa | ctcaccctct | 1920 |
| cctgccattg | agccgccgac | agacaccctc | cccgcaccgc | cagtggtgac | attacttttt | 1980 |
| tatattttat | tgaatttatg | ttgatgagtc | tatataatta | ctttagataa | atttatacac | 2040 |
| acaaatttct | cctcaaaaaa | taataataac | atgaatatat | gtatataaat | acatcgcaat | 2100 |
| aagagaaata | taaaaatata | tacacaaaaa | aagtaaaaat | tcatataaac | atccttaata | 2160 |
| tacaaattta | tatattcgca | tatatatact | tatacaaatt | tatataattt | tatacacgtg | 2220 |

```
taaaaaatta tataaacttg cggcatgctg cttttctcggg aagatggtga catgtcgggt    2280
aacatccgaa aatatgagac attttttggta attttcattt ttgcttgtct tttagcgtaa    2340
ttatcccctta ttttttttat tttttctatg tactccttcc gtcataattt atgtgacacc    2400
attttctttt ttgtttatct caaaaagaat tacacatttc tttatttgac aattatttaa    2460
tataccatct ttattttaca tttgttggat tctacatact tttaaagcta ccaacaattt    2520
ttgtattact caaatattct ctttcttatt ttttcaagag taaaattgaa acttacaag     2580
gtcaatctct attttcctta aactcattag taccacataa aatgagaagg atggattata    2640
atttattctt cttttttaga aaggtggagt aaaatattct gtgaaagtac accaatcgat    2700
tttgtgactg tcaatactta tatggtggaa taacatatct aaattagtca gggtcccaaa    2760
agtatacctc actaacaatg aactagatta tgtcaaacgt tgtatcgtta gttgcactag    2820
aaaattaatc gtatcactga tactcttta gtattcttaa aattgacgaa taatacattt     2880
ctagccggta tgaagacctt cttttttccct tttctttaat aggttctcta tttggggtct   2940
ttaatttaat ctagctacta tttagttttg accttaata taattcagaa ccctcatgta     3000
acgttacaga attacatgca aaactaaaga agatgaagat ctaattaaat tgataactcg    3060
aactttgtat ttgttccctg tttgccatgt ccaaaagtcc gtccgccatg acttcacttg    3120
tatgatttgc aagttgaact gtggaatttc gattacaaat acaacttgtc aagtatagta    3180
ttttaaatta aacataaaaa atgaatttgc attgagaact tatagtaatt ttttttcaatt   3240
aagattattt agtgaaatta atcttcaaat gcaacttgaa catctataat gtttaaaggc    3300
cttttatcgt tagtgacgcc atatggatga cttgggctga tgacaccaat gtgatgatga    3360
ttgattcctt agtaacaag tacctatagt actaggaaac agcgactttt ggatatgttg     3420
ttagtaattt tttaaagtaa tattttgaaa tcagcatctt tggatcgatt tcccagtgga    3480
tgtataagag tcactttatt tttctcttat catgcccatt aattaatttt ttaaattttt    3540
ttacaactaa ttattatgtg tattatatct aattgtgtcc ttatttacta accttgctga    3600
ccaagtttaa gtacattaat cttttcttac ctctttaatc aagggtaaga ttagaaaaaa    3660
ataattaatt ttccattgat tttctaaagt gataggagta cttattttgg gacaactaaa    3720
aagagaaaat tgatatttat taaggacgga tggtgtatga tagaatacta atttttttat    3780
ggaaaataga aatgtatcat tttgtatttg aaaatagttt acctttagat tgtcgatcat    3840
tctcttaaat tcatgatttt atagctatag aaatgtaatt gttggtttaa agctcaagtt    3900
ttcaagaatt tcctcaattt tttttttgtct atactcaaat aagttcacaa taaaataaat    3960
agatggaaac tcagcatcct cgctaagcaa atatataata catcaacaaa acacgtgaga    4020
gttgtttggt atgcaaggaa gtgacattag accatagtga ttcggtttga actcttagct    4080
tgtccgccta aacacaaaat ggacaatatc agtagtagat ttgacggttt aatattttca    4140
aattgcattt tcaattttaa ctgaaaaatg aatcttataa cgttattaat attttcgttg    4200
acagggaaat cgttagcaga tattgcatag aagttcgaca acttggatat agattacaag    4260
aagcaatatc agagagctta ggcctagaga aagattgtat aaaaaatata ttgggtgaac    4320
aaggtcaaca tatggctgtt aattattacc ctccatgtcc agaaccagaa ctaacttatg    4380
gtttgccagc ccatactgat cctaatgccc ttactatact tcttcaagac ttgcaagtag    4440
caggtcttca agttctcaag gatggtaaat ggttatctgt gaaacctcgg gccaatgcct    4500
ttgtcatcaa tcttggtgat caattgcagg taaagtatat ctctttcatt caacataatt    4560
```

```
taatttctat ccacctgaca gtttaagatc aatttcatca cttatcaggt cacataaaaa    4620
gtactatagt tatgctataa gtatatatca aacctagctt gttaaacatt atgtacacat    4680
tatagaacat aaactcattt caaaatatta ctttaacaag taacataatg tataaaaggc    4740
ccgtggttat cctgcaggcg ctgagtaatg gaaaatatag aagtgtatgg cacagagcta    4800
tagtaaattc agacaaacca aggctgtcag tggcttcttt cttgtgtcct agtgattgtg    4860
cgataatcag tgctccaaaa accttaactg aagatgggtc tccaaccatt tatcgggatt    4920
tcacgtatcc agaatattac aagaaatttt ggagcagaaa tttagatcaa gaacactgta    4980
tggaactttt caagaaagga agctagctta gtgtttatgt ccagcaattt catctgctta    5040
cttaagttcg cgcaggggtg gaggtagggt tttatttggt agaaccgaat aactttctca    5100
aatcatgtgt atgtgtttta aaaaatatat taagtatgaa caaattatga acttagttaa    5160
tagcacatga acacctgtat tagaatccag aactaataaa tttcaaatcc ttaataaatc    5220
gggcgggtag ccatccgacc ctctaataag tgtcttagga gatttgtgca agcattttc    5280 tttgtaaaag tttcctttc ttgttgtatt ggaaaaactt tttctgaaac aagatccaag    5340
gcaactgtcc tgtccatata ttgtctaatt ggaaaagttc ataattcact tgaagaattc    5400
cataatccaa atgctaaaag caaaatatgc cttgcgaaat tctgtgaaac cagccatgaa    5460
taatccactg caagaacata atttatcacc atttcacgta ggttcataag catcaactaa    5520
agctaactga ttagttacaa accaattagg actataatga tgccgaagat gagacaggtt    5580
taatagtgat atgaactcta accatgttaa ctgaaaaaca aactcgggtt tcaggtaaaa    5640
atatggtcac agtgtgattc acacgaatag gctattttca tgtgttgttt aagttttta    5700 aatttgcgaa agattaatct cacttatttg agttttggca gacgcatgtt aacaatctca    5760
ttacaagttt tgattgatcc gtcaaaagta tatatgttaa caactactga atcgttaaaa    5820
cctgggtaca ctattaaaaa attacaagtt tgacatgtcc atcatacact ggtaaacaat    5880
tgaacttttg acacattcat caaacttgca aatattgcta tttcttacac aatgtcataa    5940
caaggtcaaa acttaagcag aaccatgcca aatggccacc tgatcaattt atttctgata    6000
gacaata                                                              6007
```

<210> SEQ ID NO 16
<211> LENGTH: 4231
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1022, 1023, 1024, 1025, 1026, 1027, 1028, 1029, 1030,
      1031, 1032, 1033, 1034, 1035, 1036, 1037
<223> OTHER INFORMATION: n = A,T,C or G

<400> SEQUENCE: 16

```
atggaatcta atgttatttc agcggaacc aaatacacaa acctccctaa aagttatgtt      60
cgcccagaat cccaacgacc tcggttatct gaagtagacg attgccaaga taatattcca     120
gttattgatt tgtgttgcag agacaataac gttatcattc aacaattgga agaagcttgt     180
cgtctttatg gcttttttca ggtacttaca cttacacata aaattatgag ttaccttca     240 ctggcataag tactaaaaaa attgtgccat aaaaaattgg atagatgaga agaaaatcag     300
ctcgtattta ttttttctgg aatttaaatc ttccttgtag ctcaacagtca aacaagactc    360 gccctttggat gcaattcatt aaaaatatta agtataatt tttttttgtg acatatcttc    420
```

```
tctcctttt  tttttttaaa   aaaaaattaa  aaacgaaata  ttatatatta  agggatgctc   480
acaattagaa  gcaaaggcta  cgttgagcat  caaagatacc  aaagtaccaa  agttagctag   540
catattacag  atcccaaaag  agatgtttgc  atcattcaca  aaagtagtag  tactactagt   600
agaaggcgac  tgaagaaata  cacactctag  agctactata  attagtgagt  ccatcattca   660
caaaagtagt  aataatacta  gtgacgggcc  ttctcatcat  tttaatggaa  cttcttgatg   720
atcaggtaat  aaaccatggt  gtaccaaaga  actaataga   ggaaatgcta  ggggtagctc   780
atgagttttt  caagctacca  gtggaagaga  agatgaagtt  gtactcagat  gatccatcaa   840
agaccatgag  attatcaaca  agttttaatg  tgaagaagga  aactgttcat  aaatcataat   900
tggagagact  atcttagatt  gcactgctat  cctttggaga  aatatgcccc  tgaatggcct   960
tctactccct  cttctttcag  gtaagtaaac  gcctttaaag  cccgatagct  ttttttttt   1020 tnnnnnnnnn  nnnnnnnaac  tacaaacaac  atgccatatt  ttttttatg   catatcacat  1080 attcttaaaa  ttacaaattt  tagcactcct  taaaaaaaaa  aacttagcta  caaaactcac  1140
cctctcctgc  cattgagccg  ccgacagaca  ccctccccgc  accgccagtg  gtgacattac  1200
ttttttatat  tttattgaat  ttatgttgat  gagtctatat  aattacttta  gataaattta  1260
tacacacaaa  tttctcctca  aaaataaat   aatacatgaa  tatatgtata  taaatacatc  1320
gcaataagag  aaatataaaa  atatatacac  aaaaaaagta  aaaattcata  taaacatcct  1380
taatatacaa  atttatatat  tcgcatatat  atacttatac  aaatttatat  aattttatac  1440
acgtgtaaaa  aattatataa  acttgcggca  tgctgctttc  tcgggaagat  ggtgacatgt  1500
cgggtaacat  ccgaaaatat  gagacatttt  tggtaatttt  catttttgct  tgtcttttag  1560
cgtaattatc  ccttatttt   tttatttttt  ctatgtactc  cttccgtcat  aatttatgtg  1620
acaccatttt  ctttttgtt   tatctcaaaa  agaattacac  atttctttat  ttgacaatta  1680
tttaatatac  catctttatt  ttacatttgt  tggattctac  atacttttaa  agctaccaac  1740 aattttgta   ttactcaaat  attctctttc  ttattttttc  aagagtaaaa  ttgaaacttt  1800
acaaggtcaa  tctctatttt  tcttaaactc  attagtacca  cataaaatga  gaaggatgga  1860
ttataattta  ttcttctttt  ttagaaaggt  ggagtaaaat  attctgtgaa  agtacaccaa  1920
tcgattttgt  gactgtcaat  acttatatgg  tggaataaca  tatctaaatt  agtcagggtc  1980
ccaaaagtat  acctcactaa  caatgaacta  gattatgtca  aacgttgtat  cgttagttgc  2040
actagaaaat  taatcgtatc  actgatactc  ttttagtatt  cttaaaattg  acgaataata  2100
catttctagc  cggtatgaag  accttctttt  tccctttct   ttaataggtt  ctctatttgg  2160 ggtcttaat   ttaatctagc  tactatttag  ttttgacctt  taatataatt  cagaaccctc  2220
atgtaacgtt  acagaattac  atgcaaaact  aaagaagatg  aagatctaat  taaattgata  2280
actcgaactt  tgtatttgtt  ccctgtttgc  catgtccaaa  agtccgtccg  ccatgacttc  2340
acttgtatga  tttgcaagtt  gaactgtgga  atttcgatta  caaatacaac  ttgtcaagta  2400
tagtatttta  aattaaacat  aaaaaatgaa  tttgcattga  gaacttatag  taatttttt   2460 caattaagat  tatttagtga  aattaatctt  caaatgcaac  ttgaacatct  ataatgttta  2520
aaggcctttt  atcgttagtg  acgccatatg  gatgacttgg  gctgatgaca  ccaatgtgat  2580
gatgattgat  tccttagtta  acaagtacct  atagtactag  gaaacagcga  cttttggata  2640
tgttgttagt  aattttttaa  agtaatattt  tgaaatcagc  atcttggat   cgatttccca  2700 gtggatgtat  aagagtcact  ttattttct   cttatcatgc  ccattaatta  atttttaaa   2760 tttttttaca  actaattatt  atgtgtatta  tatctaattg  tgtccttatt  tactaacctt  2820
```

```
gctgaccaag tttaagtaca ttaatctttt cttacctctt taatcaaggg taagattaga    2880
aaaaaataat taattttcca ttgattttct aaagtgatag gagtacttat tttgggacaa    2940
ctaaaaagag aaaattgata tttattaagg acggatggtg tatgatagaa tactaatttt    3000
tttatggaaa atagaaatgt atcattttgt atttgaaaat agtttacctt tagattgtcg    3060
atcattctct taaattcatg attttatagc tatagaaatg taattgttgg tttaaagctc    3120
aagttttcaa gaatttcctc aatttttttt tgtctatact caaataagtt cacaataaaa    3180
taaatagatg gaaactcagc atcctcgcta agcaaatata taatacatca acaaaacacg    3240
tgagagttgt ttggtatgca aggaagtgac attagaccat agtgattcgg tttgaactct    3300
tagcttgtcc gcctaaacac aaaatggaca atatcagtag tagatttgac ggtttaatat    3360
tttcaaattg cattttcaat tttaactgaa aaatgaatct tataacgtta ttaatatttt    3420
cgttgacagg gaaatcgtta gcagatattg catagaagtt cgacaacttg gatatagatt    3480
acaagaagca atatcagaga gcttaggcct agagaaagat tgtataaaaa atatattggg    3540
tgaacaaggt caacatatgg ctgttaatta ttaccctcca tgtccagaac cagaactaac    3600
ttatggtttg ccagcccata ctgatcctaa tgcccttact atacttcttc aagacttgca    3660
agtagcaggt cttcaagttc tcaaggatgg taaatggtta tctgtgaaac ctcgggccaa    3720
tgcctttgtc atcaatcttg gtgatcaatt gcaggtaaag tatatctctt tcattcaaca    3780
taatttaatt tctatccacc tgacagttta agatcaattt catcacttat caggtcacat    3840
aaaaagtact atagttatgc tataagtata tatcaaacct agcttgttaa acattatgta    3900
cacattatag aacataaact catttcaaaa tattacttta acaagtaaca taatgtataa    3960
aaggcccgtg gttatcctgc aggcgctgag taatggaaaa tatagaagtg tatggcacag    4020
agctatagta aattcagaca aaccaaggct gtcagtggct tctttcttgt gtcctagtga    4080
ttgtgcgata atcagtgctc caaaaacctt aactgaagat gggtctccaa ccatttatcg    4140
ggatttcacg tatccagaat attacaagaa attttggagc agaaatttag atcaagaaca    4200
ctgtatggaa cttttcaaga aaggaagcta g                                   4231
```